(12) United States Patent
Evans et al.

(10) Patent No.: US 8,435,206 B2
(45) Date of Patent: May 7, 2013

(54) INTERFACE FOR MEDICAL INFUSION PUMP

(75) Inventors: William James Evans, San Francisco, CA (US); Diana Willow Greenberg, San Francisco, CA (US); Michael L. Blomquist, Blaine, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 1380 days.

(21) Appl. No.: 11/702,925

(22) Filed: Feb. 5, 2007

(65) Prior Publication Data

US 2008/0033361 A1    Feb. 7, 2008

Related U.S. Application Data

(60) Provisional application No. 60/835,926, filed on Aug. 3, 2006.

(51) Int. Cl.
*A61F 13/20* (2006.01)

(52) U.S. Cl.
USPC .......................................................... 604/19

(58) Field of Classification Search .................... 604/29, 604/19
See application file for complete search history.

(56) References Cited

U.S. PATENT DOCUMENTS

| | | | |
|---|---|---|---|
| 2,968,804 A | 1/1961 | Buffington | |
| 3,555,286 A | 1/1971 | Cote | |
| 3,603,152 A | 9/1971 | Alibert et al. | |
| 3,777,165 A | 12/1973 | Bryant et al. | |
| 3,809,871 A | 5/1974 | Howard et al. | |
| 3,923,060 A | 12/1975 | Ellinwood, Jr. | |
| 3,942,526 A | 3/1976 | Wilder et al. | |
| 3,985,133 A | 10/1976 | Jenkins et al. | |
| 4,027,536 A | 6/1977 | Heggie | |
| T961004 I4 | 8/1977 | Horton | |
| 4,080,967 A | 3/1978 | O'Leary | |
| 4,091,550 A | 5/1978 | Schrenk et al. | |
| 4,098,267 A | 7/1978 | Stein et al. | |
| 4,137,913 A | 2/1979 | Georgi | |
| 4,141,252 A | 2/1979 | Lodge | |
| 4,146,029 A | 3/1979 | Ellinwood, Jr. | |
| 4,174,637 A | 11/1979 | Mulzet et al. | |
| 4,184,815 A | 1/1980 | Casson et al. | |

(Continued)

FOREIGN PATENT DOCUMENTS

| CA | 2060151 | 8/1992 |
|---|---|---|
| CH | 665955 | 6/1988 |

(Continued)

OTHER PUBLICATIONS

International Search Report and Written Opinion mailed Feb. 19, 2008.

(Continued)

*Primary Examiner* — Nicholas Lucchesi
*Assistant Examiner* — Diva K Chander
(74) *Attorney, Agent, or Firm* — Patterson Thuente Pedersen, P.A.

(57) ABSTRACT

Methods and apparatus for programming a medical infusion pump are disclosed. One method includes displaying a meter having two or more locations, each of the two or more locations representing a corresponding parameter value programmable into the medical infusion pump. The method further includes displaying an indicator having a selectable positional relationship to the meter, the selected position corresponding to a parameter value.

15 Claims, 41 Drawing Sheets

U.S. PATENT DOCUMENTS

| | | |
|---|---|---|
| 4,191,184 A | 3/1980 | Carlisle |
| 4,210,138 A | 7/1980 | Jess et al. |
| 4,213,454 A | 7/1980 | Shim |
| 4,217,993 A | 8/1980 | Jess et al. |
| 4,236,880 A | 12/1980 | Archibald |
| 4,270,532 A | 6/1981 | Frametzki et al. |
| 4,279,188 A | 7/1981 | Scott |
| 4,280,136 A | 7/1981 | Kasbima et al. |
| 4,282,872 A | 8/1981 | Franetzki et al. |
| 4,299,218 A | 11/1981 | Knigge et al. |
| 4,299,541 A | 11/1981 | Ohara et al. |
| 4,308,866 A | 1/1982 | Jelliffe et al. |
| 4,309,993 A | 1/1982 | Brown |
| 4,311,377 A | 1/1982 | Matteson |
| 4,314,227 A | 2/1982 | Eventoff |
| 4,314,228 A | 2/1982 | Eventoff |
| 4,315,238 A | 2/1982 | Eventoff |
| 4,320,757 A | 3/1982 | Whitney et al. |
| 4,368,645 A | 1/1983 | Glenn et al. |
| 4,369,780 A | 1/1983 | Sakai |
| 4,370,983 A | 2/1983 | Lichtenstein |
| 4,373,525 A | 2/1983 | Kobayashi |
| 4,373,527 A | 2/1983 | Fischell |
| 4,385,630 A | 5/1983 | Gilcher et al. |
| 4,385,958 A | 5/1983 | Long |
| RE31,315 E | 7/1983 | Jenkins et al. |
| 4,392,849 A | 7/1983 | Petre et al. |
| 4,394,862 A | 7/1983 | Shim |
| 4,395,259 A | 7/1983 | Prestele et al. |
| 4,396,977 A | 8/1983 | Slater et al. |
| 4,398,542 A | 8/1983 | Cunningham et al. |
| 4,410,322 A | 10/1983 | Archibald |
| 4,413,314 A | 11/1983 | Slater et al. |
| 4,425,661 A | 1/1984 | Moses et al. |
| 4,431,425 A | 2/1984 | Thompson et al. |
| 4,443,218 A | 4/1984 | DeCant, Jr. et al. |
| 4,446,344 A | 5/1984 | Fiedler |
| 4,460,355 A | 7/1984 | Layman |
| 4,484,479 A | 11/1984 | Eckhardt |
| 4,489,302 A | 12/1984 | Eventoff |
| 4,490,798 A | 12/1984 | Franks et al. |
| 4,493,704 A | 1/1985 | Beard et al. |
| 4,494,950 A | 1/1985 | Fischell |
| 4,498,843 A | 2/1985 | Schneider et al. |
| 4,512,013 A | 4/1985 | Nash et al. |
| 4,520,706 A | 6/1985 | Deforeit |
| 4,526,574 A | 7/1985 | Pekkarinen |
| 4,529,401 A | 7/1985 | Leslie et al. |
| 4,530,696 A | 7/1985 | Bisera et al. |
| 4,534,756 A | 8/1985 | Nelson |
| 4,542,532 A | 9/1985 | McQuilkin |
| 4,550,731 A | 11/1985 | Batina et al. |
| 4,550,748 A | 11/1985 | Nunez |
| 4,557,725 A | 12/1985 | Heyne et al. |
| 4,559,037 A | 12/1985 | Franetzki et al. |
| 4,559,038 A | 12/1985 | Berg et al. |
| 4,559,044 A | 12/1985 | Robinson et al. |
| 4,561,443 A | 12/1985 | Hogrefe |
| 4,562,751 A | 1/1986 | Nason et al. |
| 4,563,179 A | 1/1986 | Sakai |
| 4,565,542 A | 1/1986 | Berg |
| 4,578,573 A | 3/1986 | Flies et al. |
| 4,596,575 A | 6/1986 | Rosenberg et al. |
| 4,597,754 A | 7/1986 | Thill et al. |
| 4,601,702 A | 7/1986 | Hudson |
| 4,606,353 A | 8/1986 | Timm |
| 4,617,014 A | 10/1986 | Cannon et al. |
| 4,623,331 A | 11/1986 | Cewers et al. |
| 4,624,661 A | 11/1986 | Arimond |
| 4,627,835 A | 12/1986 | Fenton, Jr. |
| 4,627,839 A | 12/1986 | Young |
| 4,649,499 A | 3/1987 | Sutton et al. |
| 4,650,469 A | 3/1987 | Berg et al. |
| 4,652,260 A | 3/1987 | Fenton, Jr. |
| 4,656,603 A | 4/1987 | Dunn |
| 4,658,371 A | 4/1987 | Walsh et al. |
| 4,671,792 A | 6/1987 | Borsanyi |
| 4,676,776 A | 6/1987 | Hawson |
| 4,678,408 A | 7/1987 | Nason et al. |
| 4,681,563 A | 7/1987 | Deckert et al. |
| 4,685,903 A | 8/1987 | Cable et al. |
| 4,690,673 A | 9/1987 | Blomquist |
| 4,692,147 A | 9/1987 | Duggan |
| 4,696,671 A | 9/1987 | Epstein et al. |
| 4,710,163 A | 12/1987 | Butterfield |
| 4,714,462 A | 12/1987 | DiDomenico |
| 4,722,734 A | 2/1988 | Kollin |
| D294,733 S | 3/1988 | Peterson et al. |
| 4,731,051 A | 3/1988 | Fishell |
| 4,731,058 A | 3/1988 | Doan |
| 4,731,726 A | 3/1988 | Allen |
| 4,739,229 A | 4/1988 | Heiler et al. |
| 4,741,732 A | 5/1988 | Granshaw et al. |
| 4,745,301 A | 5/1988 | Michalchik |
| 4,747,828 A | 5/1988 | Tseo |
| 4,754,401 A | 6/1988 | Kaczynski et al. |
| 4,756,706 A | 7/1988 | Kerns et al. |
| 4,774,029 A | 9/1988 | Poulin |
| 4,775,368 A | 10/1988 | Iwatschenko |
| 4,778,449 A | 10/1988 | Weber et al. |
| 4,785,799 A | 11/1988 | Schoon et al. |
| 4,790,816 A | 12/1988 | Sundblom et al. |
| 4,799,381 A | 1/1989 | Tromp |
| 4,808,161 A | 2/1989 | Karmen |
| 4,808,167 A | 2/1989 | Mann et al. |
| 4,809,697 A | 3/1989 | Causey, III et al. |
| 4,810,243 A | 3/1989 | Howson |
| 4,810,992 A | 3/1989 | Eventoff |
| 4,816,019 A | 3/1989 | Karmen |
| 4,818,186 A | 4/1989 | Pastrone et al. |
| 4,826,810 A | 5/1989 | Aoki |
| 4,832,033 A | 5/1989 | Maher et al. |
| 4,836,752 A | 6/1989 | Burkett |
| 4,838,856 A | 6/1989 | Mulreany et al. |
| 4,838,857 A | 6/1989 | Strowe et al. |
| 4,842,584 A | 6/1989 | Pastrone |
| 4,846,792 A | 7/1989 | Bobo, Jr. et al. |
| 4,847,764 A | 7/1989 | Halvorson |
| 4,847,990 A | 7/1989 | Patrick |
| 4,850,807 A | 7/1989 | Frantz |
| 4,850,972 A | 7/1989 | Schulman et al. |
| 4,852,581 A | 8/1989 | Frank |
| 4,854,324 A | 8/1989 | Hirschman et al. |
| 4,856,339 A | 8/1989 | Williams |
| 4,863,425 A | 9/1989 | Slate et al. |
| 4,869,722 A | 9/1989 | Heyman |
| 4,871,351 A | 10/1989 | Feingold |
| 4,878,896 A | 11/1989 | Garrison et al. |
| 4,882,575 A | 11/1989 | Kawahara et al. |
| 4,889,132 A | 12/1989 | Hutcheson et al. |
| 4,898,578 A | 2/1990 | Rubalcaba, Jr. |
| 4,901,221 A | 2/1990 | Kodosky et al. |
| 4,908,017 A | 3/1990 | Howson et al. |
| 4,914,568 A | 4/1990 | Kodosky et al. |
| 4,918,930 A | 4/1990 | Gaudet et al. |
| 4,919,650 A | 4/1990 | Feingold et al. |
| 4,925,444 A | 5/1990 | Orkin et al. |
| 4,927,411 A | 5/1990 | Pastrone et al. |
| 4,933,873 A | 6/1990 | Kaufman et al. |
| 4,942,514 A | 7/1990 | Miyagaki et al. |
| 4,943,279 A | 7/1990 | Samiotes et al. |
| 4,950,235 A | 8/1990 | Slate et al. |
| 4,950,244 A | 8/1990 | Fellingham et al. |
| 4,954,818 A | 9/1990 | Naking et al. |
| 4,957,690 A | 9/1990 | Fennern |
| 4,961,533 A | 10/1990 | Teller et al. |
| 4,970,664 A | 11/1990 | Kaiser |
| 4,976,151 A | 12/1990 | Morishita |
| 4,978,335 A | 12/1990 | Arthur, III |
| 4,979,940 A | 12/1990 | Bobo, Jr. et al. |
| 4,994,035 A | 2/1991 | Mokros |
| 4,996,511 A | 2/1991 | Ohkawa et al. |
| 5,000,739 A | 3/1991 | Kulisz et al. |
| 5,006,997 A | 4/1991 | Reich |
| 5,009,641 A | 4/1991 | Gorton |
| 5,010,473 A | 4/1991 | Jacobs |
| 5,017,059 A | 5/1991 | Davis |

| | | | | | |
|---|---|---|---|---|---|
| 5,032,978 A | 7/1991 | Blomquist | 5,389,071 A | 2/1995 | Kawahara et al. |
| 5,034,004 A | 7/1991 | Crankshaw | 5,389,078 A | 2/1995 | Zelesky et al. |
| 5,038,800 A | 8/1991 | Oba | 5,395,321 A | 3/1995 | Kawahara et al. |
| 5,041,086 A | 8/1991 | Koenig et al. | 5,400,246 A | 3/1995 | Wilson et al. |
| 5,047,014 A | 9/1991 | Mosebach et al. | 5,412,400 A | 5/1995 | Takahara et al. |
| 5,050,612 A | 9/1991 | Matsumura | 5,429,602 A | 7/1995 | Hauser |
| 5,053,585 A | 10/1991 | Yaniger | 5,431,627 A | 7/1995 | Pastrone et al. |
| 5,053,990 A | 10/1991 | Kreifels | 5,432,709 A | 7/1995 | Vollweiler et al. |
| 5,062,774 A | 11/1991 | Kramer et al. | 5,440,585 A | 8/1995 | Patridge, III |
| 5,069,668 A | 12/1991 | Boydman | 5,456,691 A | 10/1995 | Snell |
| 5,074,756 A | 12/1991 | Davis | 5,478,211 A | 12/1995 | Dominiak et al. |
| 5,078,682 A | 1/1992 | Miki et al. | 5,479,643 A | 12/1995 | Bhaskar et al. |
| 5,078,683 A | 1/1992 | Sancoff et al. | 5,481,250 A | 1/1996 | Hano |
| 5,082,014 A | 1/1992 | Olichney | 5,482,446 A | 1/1996 | Williamson et al. |
| 5,084,828 A | 1/1992 | Kaufman et al. | 5,485,408 A | 1/1996 | Blomquist |
| 5,087,245 A | 2/1992 | Doan | 5,531,697 A | 7/1996 | Olsen et al. |
| 5,088,983 A | 2/1992 | Burke | 5,531,698 A | 7/1996 | Olsen |
| 5,096,385 A | 3/1992 | Georgi et al. | 5,537,436 A | 7/1996 | Bottoms et al. |
| 5,098,262 A | 3/1992 | Wecker et al. | 5,558,640 A | 9/1996 | Pfeiler et al. |
| 5,098,409 A | 3/1992 | Stock | 5,569,187 A | 10/1996 | Kaiser |
| 5,100,380 A | 3/1992 | Epstein et al. | 5,573,506 A | 11/1996 | Vasko |
| 5,103,211 A | 4/1992 | Daoud et al. | 5,582,593 A | 12/1996 | Hultman |
| 5,104,374 A | 4/1992 | Bishko et al. | 5,594,786 A | 1/1997 | Chaco et al. |
| 5,111,234 A | 5/1992 | Taniguchi et al. | 5,598,420 A | 1/1997 | Kaufman |
| 5,115,223 A | 5/1992 | Moody | 5,616,121 A | 4/1997 | McKay |
| 5,116,312 A | 5/1992 | Blankenship et al. | 5,626,144 A | 5/1997 | Tacklind et al. |
| 5,122,820 A | 6/1992 | Pagano et al. | 5,630,710 A | 5/1997 | Tune et al. |
| 5,124,744 A | 6/1992 | Ogura et al. | 5,643,212 A | 7/1997 | Coutre et al. |
| 5,124,802 A | 6/1992 | Ito et al. | 5,647,854 A | 7/1997 | Olsen et al. |
| 5,131,816 A | 7/1992 | Brown et al. | 5,658,250 A | 8/1997 | Blomquist et al. |
| 5,140,862 A | 8/1992 | Pappalardo | 5,658,252 A | 8/1997 | Johnson |
| 5,153,827 A | 10/1992 | Coutre et al. | 5,660,176 A | 8/1997 | Iliff |
| 5,154,700 A | 10/1992 | Danby | 5,665,065 A | 9/1997 | Colman et al. |
| 5,155,693 A | 10/1992 | Altmayer et al. | 5,669,877 A | 9/1997 | Blomquist |
| 5,157,928 A | 10/1992 | Gaudlet et al. | 5,681,285 A | 10/1997 | Ford et al. |
| 5,168,441 A | 12/1992 | Onarheim et al. | 5,685,844 A | 11/1997 | Marttila |
| 5,172,698 A | 12/1992 | Stanko | 5,687,734 A | 11/1997 | Dempsey et al. |
| 5,174,472 A | 12/1992 | Raque et al. | 5,695,473 A | 12/1997 | Olsen |
| 5,176,004 A | 1/1993 | Gaudet | 5,704,366 A | 1/1998 | Tacklind et al. |
| 5,181,910 A | 1/1993 | Scanlon | 5,706,458 A | 1/1998 | Koppolu |
| 5,190,442 A | 3/1993 | Jorritsma | 5,717,603 A | 2/1998 | McClendon et al. |
| 5,190,522 A | 3/1993 | Wojiciki et al. | 5,718,562 A | 2/1998 | Lawless et al. |
| 5,207,642 A | 5/1993 | Orkin et al. | 5,719,761 A | 2/1998 | Gatti et al. |
| 5,211,626 A | 5/1993 | Frank et al. | 5,764,159 A | 6/1998 | Neftel |
| 5,213,573 A | 5/1993 | Sorich et al. | 5,772,635 A | 6/1998 | Dastur et al. |
| 5,217,355 A | 6/1993 | Hyman et al. | 5,781,442 A | 7/1998 | Engleson et al. |
| 5,219,327 A | 6/1993 | Okada | 5,782,805 A | 7/1998 | Meinzer et al. |
| 5,221,268 A | 6/1993 | Barton et al. | 5,788,669 A | 8/1998 | Peterson |
| 5,224,051 A | 6/1993 | Johnson | 5,807,336 A | 9/1998 | Russo et al. |
| 5,230,623 A | 7/1993 | Guthrie et al. | 5,810,771 A | 9/1998 | Blomquist |
| 5,238,001 A | 8/1993 | Gallant et al. | 5,814,015 A | 9/1998 | Gargano et al. |
| 5,241,461 A | 8/1993 | Georges | 5,822,715 A | 10/1998 | Worthington et al. |
| 5,244,461 A | 9/1993 | Derlien | 5,857,967 A | 1/1999 | Frid et al. |
| 5,244,463 A | 9/1993 | Cordner, Jr. et al. | 5,861,018 A | 1/1999 | Feierbach |
| 5,247,434 A | 9/1993 | Peterson et al. | 5,868,669 A | 2/1999 | Iliff |
| 5,256,157 A | 10/1993 | Samiotes et al. | 5,871,465 A | 2/1999 | Vasko |
| 5,265,431 A | 11/1993 | Gaudet et al. | 5,876,370 A | 3/1999 | Blomquist |
| 5,267,218 A | 11/1993 | Elbert | 5,879,163 A | 3/1999 | Brown et al. |
| 5,291,190 A | 3/1994 | Scarola et al. | 5,885,245 A | 3/1999 | Lynch et al. |
| 5,295,062 A | 3/1994 | Fukshima | 5,895,371 A | 4/1999 | Levitas et al. |
| 5,301,301 A | 4/1994 | Kodusky et al. | 5,897,493 A | 4/1999 | Brown |
| 5,307,263 A | 4/1994 | Brown | 5,899,855 A | 5/1999 | Brown |
| 5,315,530 A | 5/1994 | Gerhardt et al. | 5,913,310 A | 6/1999 | Brown |
| 5,317,506 A | 5/1994 | Coutre et al. | 5,918,603 A | 7/1999 | Brown |
| 5,321,601 A | 6/1994 | Riedel et al. | 5,925,021 A | 7/1999 | Castellano et al. |
| 5,338,157 A | 8/1994 | Blomquist | 5,933,136 A | 8/1999 | Brown |
| 5,339,821 A | 8/1994 | Fujimoto | 5,935,099 A | 8/1999 | Peterson et al. |
| 5,350,411 A | 9/1994 | Ryan et al. | 5,935,106 A | 8/1999 | Olsen |
| 5,353,316 A | 10/1994 | Scarola et al. | 5,940,801 A | 8/1999 | Brown |
| 5,354,273 A | 10/1994 | Hagen | 5,956,501 A | 9/1999 | Brown |
| 5,356,378 A | 10/1994 | Doan | 5,960,403 A | 9/1999 | Brown |
| 5,357,427 A | 10/1994 | Langen et al. | 5,966,691 A | 10/1999 | Kibre et al. |
| 5,363,482 A | 11/1994 | Victor et al. | 5,997,476 A | 12/1999 | Brown |
| 5,364,346 A | 11/1994 | Schrezenmeir | 6,012,034 A | 1/2000 | Hamparian et al. |
| 5,368,562 A | 11/1994 | Blomquist et al. | 6,024,539 A | 2/2000 | Blomquist |
| 5,376,070 A | 12/1994 | Purvis et al. | 6,032,119 A | 2/2000 | Brown et al. |
| 5,383,855 A | 1/1995 | Nicholson et al. | 6,077,055 A | 6/2000 | Vilks |
| 5,386,360 A | 1/1995 | Wilson et al. | 6,101,478 A | 8/2000 | Brown |
| 5,388,202 A | 2/1995 | Squires et al. | RE36,871 E | 9/2000 | Epstein et al. |

| Patent No. | Date | Inventor |
|---|---|---|
| 6,241,704 B1 | 6/2001 | Peterson et al. |
| 6,246,992 B1 | 6/2001 | Brown |
| 6,248,067 B1 | 6/2001 | Mavity et al. |
| 6,269,340 B1 | 7/2001 | Ford et al. |
| 6,406,426 B1 | 6/2002 | Reuss et al. |
| 6,422,057 B1 | 7/2002 | Anderson |
| 6,475,180 B2 | 11/2002 | Peterson et al. |
| 6,551,276 B1 | 4/2003 | Mann et al. |
| 6,554,798 B1 | 4/2003 | Mann et al. |
| 6,558,320 B1 | 5/2003 | Causey, III et al. |
| 6,641,533 B2 | 11/2003 | Causey, III et al. |
| 6,671,563 B1 | 12/2003 | Engelson et al. |
| 6,689,091 B2 | 2/2004 | Bui et al. |
| 6,744,350 B2 | 6/2004 | Blomquist |
| 6,749,586 B2 | 6/2004 | Vasko |
| 6,765,877 B1 | 7/2004 | Foschiano et al. |
| 6,790,198 B1 | 9/2004 | White et al. |
| 6,809,653 B1 | 10/2004 | Mann et al. |
| 6,852,104 B2 | 2/2005 | Blomquist |
| 6,872,200 B2 | 3/2005 | Mann et al. |
| 6,903,743 B2 | 6/2005 | Ng |
| 6,904,434 B1 | 6/2005 | Wallach et al. |
| 6,936,029 B2 | 8/2005 | Mann et al. |
| 6,956,572 B2 | 10/2005 | Zaleski |
| 6,979,326 B2 | 12/2005 | Mann et al. |
| 6,997,920 B2 | 2/2006 | Mann et al. |
| 6,999,854 B2 | 2/2006 | Roth |
| 7,025,743 B2 | 4/2006 | Mann et al. |
| 7,033,338 B2 | 4/2006 | Vilks et al. |
| 7,036,089 B2 | 4/2006 | Bauer |
| 7,041,082 B2 | 5/2006 | Blomquist et al. |
| 7,042,643 B2 | 5/2006 | Miles |
| 7,098,803 B2 | 8/2006 | Mann et al. |
| 7,103,578 B2 | 9/2006 | Beck et al. |
| 7,109,878 B2 | 9/2006 | Mann et al. |
| 7,300,418 B2 | 11/2007 | Zaleski |
| 7,324,012 B2 | 1/2008 | Mann et al. |
| 7,347,836 B2 | 3/2008 | Peterson |
| D570,363 S | 6/2008 | Ulm et al. |
| D576,175 S | 9/2008 | Onodera |
| D580,948 S | 11/2008 | Tomizawa et al. |
| D586,351 S | 2/2009 | Gelman et al. |
| D586,357 S | 2/2009 | Janinski |
| D604,741 S | 11/2009 | DeBleser et al. |
| 7,647,237 B2 | 1/2010 | Malave et al. |
| 7,654,976 B2 | 2/2010 | Peterson et al. |
| 7,689,939 B1 | 3/2010 | Becker |
| 7,708,717 B2 | 5/2010 | Estes et al. |
| 7,789,859 B2 | 9/2010 | Estes et al. |
| 7,794,427 B2 | 9/2010 | Estes et al. |
| 2001/0031944 A1 | 10/2001 | Peterson et al. |
| 2002/0107476 A1 | 8/2002 | Mann et al. |
| 2002/0151804 A1 | 10/2002 | O'Mahony et al. |
| 2002/0183693 A1 | 12/2002 | Peterson et al. |
| 2002/0193679 A1 | 12/2002 | Malave et al. |
| 2003/0011646 A1 | 1/2003 | Levine et al. |
| 2003/0060765 A1 | 3/2003 | Campbell et al. |
| 2003/0069650 A1 | 4/2003 | Karmiy et al. |
| 2003/0114836 A1 | 6/2003 | Estes et al. |
| 2003/0139701 A1 | 7/2003 | White et al. |
| 2003/0144880 A1 | 7/2003 | Kaivan et al. |
| 2003/0145053 A1 | 7/2003 | Bodin |
| 2003/0163088 A1 | 8/2003 | Blomquist |
| 2003/0163223 A1 | 8/2003 | Blomquist |
| 2003/0163789 A1 | 8/2003 | Blomquist |
| 2003/0173408 A1 | 9/2003 | Mosher et al. |
| 2003/0204413 A1 | 10/2003 | Riff |
| 2003/0204415 A1 | 10/2003 | Knowlton |
| 2003/0204416 A1 | 10/2003 | Sayeh et al. |
| 2003/0212364 A1 | 11/2003 | Mann |
| 2003/0212379 A1 | 11/2003 | Bylund et al. |
| 2004/0010425 A1 | 1/2004 | Wilkes et al. |
| 2004/0065321 A1 | 4/2004 | Stenzler |
| 2004/0073095 A1 | 4/2004 | Causey, III et al. |
| 2004/0167465 A1 | 8/2004 | Mihai et al. |
| 2004/0172302 A1 | 9/2004 | Martucci et al. |
| 2004/0176984 A1 | 9/2004 | White et al. |
| 2004/0249673 A1 | 12/2004 | Smith |
| 2005/0001797 A1 | 1/2005 | Miller |
| 2005/0030164 A1 | 2/2005 | Blomquist |
| 2005/0055242 A1 | 3/2005 | Bello et al. |
| 2005/0137530 A1 | 6/2005 | Campbell et al. |
| 2005/0144182 A1 | 6/2005 | Boris et al. |
| 2005/0171513 A1 | 8/2005 | Mann et al. |
| 2005/0177395 A1 | 8/2005 | Blomquist |
| 2005/0246416 A1 | 11/2005 | Blomquist |
| 2006/0001550 A1 | 1/2006 | Mann et al. |
| 2006/0026205 A1 | 2/2006 | Butterfield |
| 2006/0041222 A1* | 2/2006 | Dewing et al. ............ 604/93.01 |
| 2006/0079768 A1 | 4/2006 | Small et al. |
| 2006/0132292 A1 | 6/2006 | Blomquist |
| 2006/0202859 A1 | 9/2006 | Mastrototaro et al. |
| 2006/0229557 A1* | 10/2006 | Fathallah et al. ............ 604/131 |
| 2007/0156033 A1 | 7/2007 | Causey, III et al. |
| 2007/0213657 A1 | 9/2007 | Jennewine et al. |
| 2007/0255322 A1 | 11/2007 | Gerber et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033402 A1 | 2/2008 | Blomquist |
| 2008/0033749 A1 | 2/2008 | Blomquist |
| 2008/0034323 A1 | 2/2008 | Blomquist |
| 2008/0065007 A1 | 3/2008 | Peterson et al. |
| 2008/0065016 A1 | 3/2008 | Peterson et al. |
| 2008/0126969 A1 | 5/2008 | Blomquist |
| 2008/0132844 A1 | 6/2008 | Peterson et al. |
| 2008/0300534 A1 | 12/2008 | Blomquist |
| 2009/0177180 A1 | 7/2009 | Rubalcaba et al. |
| 2009/0275886 A1 | 11/2009 | Blomquist et al. |
| 2010/0020064 A1 | 1/2010 | Roosendaal et al. |
| 2012/0013625 A1 | 1/2012 | Blomquist et al. |
| 2012/0013802 A1 | 1/2012 | Blomquist et al. |

FOREIGN PATENT DOCUMENTS

| | | |
|---|---|---|
| EP | 0069350 | 1/1983 |
| EP | 0078645 | 5/1983 |
| EP | 0183351 | 6/1986 |
| EP | 0188288 | 7/1986 |
| EP | 0221005 | 5/1987 |
| EP | 0233115 | 8/1987 |
| EP | 319272 | 6/1989 |
| EP | 0328162 | 8/1989 |
| EP | 0384155 | 8/1990 |
| EP | 408483 | 1/1991 |
| EP | 0497041 | 8/1992 |
| EP | 503670 | 9/1992 |
| EP | 0371507 | 3/1993 |
| EP | 551088 | 7/1993 |
| EP | 0806738 | 12/1997 |
| EP | 0952541 | 10/1999 |
| EP | 1587017 | 10/2005 |
| EP | 1647291 | 4/2006 |
| FR | 2603488 | 3/1988 |
| FR | 2675288 | 10/1992 |
| GB | 2039083 | 7/1980 |
| GB | 2262452 | 6/1993 |
| GB | 2 312 055 A | 10/1997 |
| JP | 409192218 | 7/1997 |
| JP | 2002291706 | 10/2002 |
| WO | WO8703814 | 7/1987 |
| WO | WO8707161 | 12/1987 |
| WO | WO91/16609 | 10/1991 |
| WO | WO92/08647 | 5/1992 |
| WO | WO92/15439 | 9/1992 |
| WO | WO94/05355 | 3/1994 |
| WO | WO94/08647 | 4/1994 |
| WO | WO 8403218 | 8/1994 |
| WO | WO95/02426 | 1/1995 |
| WO | WO95/25893 | 9/1995 |
| WO | WO95/28190 | 10/1995 |
| WO | WO96/03168 | 2/1996 |
| WO | WO96/20745 | 7/1996 |
| WO | WO96/36389 | 11/1996 |
| WO | WO97/15227 | 5/1997 |
| WO | WO97/25083 | 7/1997 |
| WO | WO98/20439 | 5/1998 |
| WO | WO98/24358 | 6/1998 |
| WO | WO98/42407 | 10/1998 |

| | | |
|---|---|---|
| WO | WO98/59487 | 12/1998 |
| WO | WO99/08183 | 2/1999 |
| WO | WO99/10801 | 3/1999 |
| WO | WO99/18532 | 4/1999 |
| WO | WO99/22236 | 5/1999 |
| WO | WO 00/48112 | 8/2000 |
| WO | WO0045696 | 8/2000 |
| WO | WO 0152727 | 7/2001 |
| WO | WO02/11049 | 2/2002 |
| WO | WO03/053503 | 7/2003 |
| WO | WO03/094075 | 11/2003 |
| WO | WO 2005/056083 | 6/2005 |
| WO | WO 2005/083619 | 9/2005 |
| WO | WO 2006/023636 A1 | 3/2006 |
| WO | WO 2006/073400 A1 | 7/2006 |
| WO | WO2008/019013 | 2/2008 |
| WO | WO2008/019014 | 2/2008 |
| WO | WO2008/019015 | 2/2008 |
| WO | WO2008016621 | 2/2008 |
| WO | WO2008/048587 | 4/2008 |
| WO | WO2008/019016 | 11/2008 |
| WO | WO2009/0135108 | 11/2009 |

OTHER PUBLICATIONS

Australian Office Action dated May 10, 2012 for Australian Application No. 2007282068.
Application and File History for U.S. Appl. No. 13/242,116, filed Sep. 23, 2011, inventors Blomquist et al.
Application and File History for U.S. Appl. No. 13/242,045, filed Sep. 23, 2011, inventors Blomquist et al.
Invitation to Pay Additional Fees with Partial International Search for International Application No. PCT/US2007/017133 mailed Feb. 27, 2008.
International Search Report for International Application No. PCT/US94/07582 dated Oct. 28, 1994.
Notification of Reasons for Refusal for Japanese Patent Application No. 2006-542752 dated Jun. 23, 2010.
Steinfeld,Internet-Appliance Technology Automates Test Equipment. pp. 157-169. Oct. 12, 2000.
Merritt, "Wireless Hospital Health Care Products on the Upswing". Jan. 7, 2004.
Steinfeld, Is Embedded Going Net-Crazy?? A Response. Internet Article Mar. 29, 2001.
International Search Report for International Application No. PCT/US2005/005829 dated Nov. 10, 2005.
Written Opinion for International Application No. PCT/US2005/005829 dated Nov. 10, 2005.
International Search Report for International Application No. PCT/US2004/040397 dated Feb. 7, 2006.
Written Opinion for International Application No. PCT/US2004/040397 dated Feb. 7, 2006.
International Search Report for International Application No. PCT/US2007/017138 dated Nov. 20, 2007.
Written Opinion for International Application No. PCT/US2007/017138 dated Nov. 20, 2007.
International Search Report for International Application No. PCT/US2007/017123 dated Jan. 25, 2008.
Written Opinion for International Application No. PCT/US2007/017123 dated Jan. 25, 2008.
International Search Report for International Application No. PCT/US2007/017120 dated Jan. 25, 2008.
Written Opinion for International Application No. PCT/US2007/017120 dated Jan. 25, 2008.
European Office Action for European Application No. 05713999 dated Oct. 30, 2009.
International Search Report for International Application No. PCT/US2007/017133 dated May 8, 2008.
Written Opinion for International Application No. PCT/US2007/017133 dated May 8, 2008.
International Search Report for International Application No. PCT/US2007/022051 dated Mar. 7, 2008.
Written Opinion for International Application No. PCT/US2007/022051 dated Mar. 7, 2008.
European Office Action for European Application No. 07797060 dated Jul. 3, 2009.
European Office Action for European Application No. 07797060 dated Feb. 9, 2010.
European Office Action for European Application No. 07797060 dated Dec. 8, 2010.
Australian Office Action for Application No. 2004296794 dated Dec. 3, 2009.
Notification of Reasons for Refusal for Japanese Patent Application No. 2006-554321 dispatch date Apr. 19, 2010.
Decision of Refusal for Japanese Application No. 2006-554321 dispatch date Apr. 18, 2011.
Examiner's report No. 3 on patent application No. 2005216321 by Smiths Medical ASD Inc. dated Apr. 20, 2011, Australian Government IP.
Examiner's first report on patent application No. 2005216321 by Smiths Medical ASD, INC dated Nov. 26, 2009. Australian Government IP.
Notification of Reasons for Refusal for Japanese Application No. 2006-542752 dispatch date Jun. 28, 2010.
Examiner's first report on patent application No. 2004296794 by Smiths Medical ASD, Inc. dated Dec. 3, 2009. Australian Government IP.
Examiner's report No. 2 on patent application No. 2005216321 by Smiths Medical ASD, Inc. dated Jan. 7, 2011. Australian Government IP.
Decision of Refusal for Japanese Application No. 2006-542752 dated Jul. 4, 2011.
Application and File History for U.S. Appl. No. 29/306,071, filed Apr. 1, 2008, inventor DeBleser et al.
Application and File History for U.S. Appl. No. 10/087,449, filed Feb. 28, 2002, inventor Blomquist.
Application and File History for U.S. Appl. No. 11/066,425, filed Feb. 22, 2005, inventor Blomquist.
Application and File History for U.S. Appl. No. 11/003,147, filed Dec. 3, 2004, inventor Blomquist.
Application and File History for U.S. Appl. No. 11/499,255, filed Aug. 3, 2006, inventor Blomquist.
Application and File History for U.S. Appl. No. 11/702,922, filed Feb. 5, 2007, inventors Evan et al.
Application and File History for U.S. Appl. No. 11/499,893, filed Aug. 3, 2006, inventor Blomquist.
Application and File History for U.S. Appl. No. 11/499,248, filed Aug. 3, 2006, inventor Blomquist.
Application and File History for U.S. Appl. No. 11/499,240, filed Aug. 3, 2006, inventor Blomquist.
Application and File History for U.S. Appl. No. 11/981,788, filed Oct. 31, 2007, inventor Peterson et al.
Application and File History for U.S. Appl. No. 11/981,248, filed Oct. 31, 2007, inventor Peterson et al.
Application and File History for U.S. Appl. No. 10/087,205, filed Feb. 28, 2002, inventor Blomquist.
Application and File History for U.S. Appl. No. 12/114,033, filed May 2, 2008, inventors Blomquist et al.
Application and File History for U.S. Appl. No. 07/942,288, filed Sep. 9, 1992, inventor Blomquist.
Application and File History for U.S. Appl. No. 08/090,738, filed Jul. 13, 1993, inventor Blomquist See Application and File History for U.S. Appl. No. 08/555,304, filed Nov. 8, 1995, inventor Blomquist.
Application and File History for U.S. Appl. No. 08/206,737, filed Mar. 7, 1994, inventor Blomquist.
Application and File History for U.S. Appl. No. 08/276,025, filed Jul. 15, 1994, inventor Blomquist.
Application and File History for U.S. Appl. No. 08/540,960, filed Oct. 11, 1995, inventor Blomquist See Application and File History for U.S. Appl. No. 08/782,486, filed Jan. 10, 1997, inventor Peterson.
Application and File History for U.S. Appl. No. 08/555,304, filed Nov. 8, 1995, inventor Blomquist.
Application and File History for U.S. Appl. No. 08/561,809, filed Nov. 22, 1995, inventor Peterson.
Application and File History for U.S. Appl. No. 08/586,952, filed Jan. 16, 1996, inventor Blomquist See Application and File History for U.S. Appl. No. 08/782,486, filed Jan. 10, 1997, inventor Peterson.

Application and File History for U.S. Appl. No. 08/782,486, filed Jan. 10, 1997, inventor Peterson.
Application and File History for U.S. Appl. No. 08/800,477, filed Feb. 14, 1997 inventor Blomquist.
Application and File History for U.S. Appl. No. 08/868,913, filed Jun. 4, 1997, inventor Blomquist.
Application and File History for U.S. Appl. No. 08/934,875, filed Sep. 22, 1997, inventor Blomquist.
Application and File History for U.S. Appl. No. 08/978,779, filed Nov. 26, 1997, inventor Blomquist.
Application and File History for U.S. Appl. No. 09/324,305, filed Jun. 2, 1999, inventor Peterson.
Application and File History for U.S. Appl. No. 09/421,751, filed Oct. 20, 1999, inventorBlomquist.
Application and File History for U.S. Appl. No. 09/795,266, filed Feb. 27, 2001, inventor Peterson.
Application and File History for U.S. Appl. No. 10/068,291, filed Feb. 5, 2002, inventor Peterson.
Application and File History for U.S. Appl. No. 11/981,229, filed Oct. 31, 2007, inventor Peterson.
Devices for Insulin Administration, Jean-Louis Selam, MD and M. Arthur Charles, MD, PhD., Diabetes Care, vol. 13, No. 9, Sep. 1990. pp. 955-979.
A Semi-closed loop computer-assisted insulin infusion system, Donald J. Chisholm, Edward W. Kraegen, David J. Bell and David R. Chipps, The Medical Journal of Australia, Dec. 8-22, 1984. pp. 13-17.
Hypertensive Crisis Managed by Computer-Controlled Infusion of Sodium Nitroprusside; A Model for the Closed-Loop Administration of Short-Acting Vasoactive Agents. Jeremy J. Hammond, Walter M. Kirkdendall, Richard V. Calfee, Comupters and Biomedical Research, vol. 12, pp. 97-108, 1979.
Computerized Continuous Infusion of Intravenous Anesthetic Drugs During Pediatric Cardiac Surgery; Kern FH, Ungerleider RM, Jacobs JR, Boyd JL 3rd, Reyes JG, Goodman D. Greeley WJ; Department of Anesthesiology, Duke Heart Center, Duke University Medical Center, Durham, North Carolina, Anesth Analg. Apr. 1991; 72(4): 487-92.
Use of a Microprocessor in the Control of Malignant Hypertension with Sodium Nitroprusside, Jackson RV, Love JB, Parkin WG, Wahlquist ML, Williams NS, Aust N Z J Med. Aug. 1977; 7(4):414-7.
Effective Control of Blood Pressure by Computerized Infusion of Sodium Nitroprusside, R.V. Calfee, J.J. Hammond, W.M. Kirkendall, Clinical Research, vol. 25, 1977.
Automated Patient Care Following Cardiac Surgery. Nicholas T. Kouchoukos; Louis B. Sheppard; John W. Kirklin, Cardiovascular Clinics, Bol. 3, pp. 110-120, 1971.
A Simulation Study on a Self-Tuning Portable Controller of Blood Glucose. Brunetti P, Cobelli C, Cruciani P, Fabietti PG, Filippucci F, Santeusanio F, Sarti E. Medical Pathology Institute, Bioengineering Laboratory. University of Perugia, Italy. Int. J. ArtifOrgans. Jan. 1993; 16(1):51-7.
A Semi-Closed Loop Computer-Assisted Insulin Infusion System. Hospital use for Control of Diabetes in Patients, Chisholm DJ, Kraegan EW, Bell DJ, Chipps DR, Med J. Aust. Dec. 8-22, 1984;141(12-13):784-9.
Patient-controlled Portable Insulin Infusion Pump in Diabetes, Jergen Bojsen, Thorsten Decked, Klaus Kelendorf, and Birthe Lerup, Diabetes vol. 28 Nov. 1979. Cover page and pp. 974-979.
Block Medical: Growing a with Home Infusion Therapy, In Vivio, The Business and Medicine Report, Apr. 1991, 3 pages.
Abbot Literature, 37 pages, as submitted Jun. 29, 1988 in U.S. Appl. No. 08/868,913.
Baxter Literature for MultiPlex™ Series 100 Fluid Management System, 4 pages, as submitted Jun. 29, 1988 in U.S. Appl. No. 08/868,913.
Baxter Literature for Flo-Guard® 6201 Volumetric Infusion Pump, Copyright 1992, 2 pages.
Greg Sancoff. San Diego Executive, "A Better Mousetrap," Sep. 1989, 4 pages.
Blade-Citizen, "Entrepeneur takes Aim at Home Health Care Market," Dec. 31, 1989, 2 pages.

"Product Overview, Verifuse Ambulatory Infusion Pump." Block Medical Inc, dated Sep. 1990, 4 pages.
Peter Lord et al., "MinMed Technologies Programmable Implantable Infusion System," pp. 66-91, from Annals of the New York Academy of Sciences, Neurilogical Applications of Implanted Drug Pumps, Copyright 1988.
Dertouzos, M., "Communications, Computers & Net-works," Scietific American Sep. 1991, pp. 62-69.
Dehne, T., "PC-Based Data Acquisition and Intrumentation," Analytical Chemistry, vol. 62, No. 9, May 1, 1990. pp. 565A, 566A, 568A, 570A, 571A, 572A.
"ally™ Ambulatory Frug Infusion System", Q-Life Systems Inc., 3 pages, as submitted Jun. 29, 1988 in U.S. Appl. No. 08/868,913.
Fundamentals of Interactive Computer Graphics, Foley et al., Mar. 1993, pp. 10, 11, 29-35.
IMED Status Infusion Management System literature, 6 pages, as submitted Jun. 29, 1988 in U.S. Appl. No. 08/868,913.
Linkens et al., Computer Control Systems and Pharmacological Drug Administration: A Survey, Journal of Medical Engineering & Technology, vol. 14, No. 2, Mar./Apr. 1990, pp. 41-54.
McCarthy, LH, Software Simulates Instrumentation Systems, Design News, May 21, 1990, pp. 72-73.
National Instruments Document entitled "Scientific Data Analysis," 16 pages, as submitted Jun. 29, 1988 in U.S. Appl. No. 08/868,913.
National Instruments Instrumentation Newsletter, Aug. 1990, 20 pages. vol. 2, No. 3.
National Instruments Instrumentation Newsletter, Feb. 1991, 20 pages. vol. 3, No. 1.
National Instruments Instrumentation Newsletter, May 1990, 18 pages. vol. 2, No. 2.
National Instruments Instrumentation Newsletter, Nov. 1990, 16 pages. vol. 2, No. 4.
National Instruments Lab Windows 2.0 materials, 6 pages, as submitted Jun. 29, 1988 in U.S. Appl. No. 08/868,913.
National Instruments Lab Windows 1.2 materials dated Oct. 1989, 5 pages.
Bedder, M. et al., "Cost Analysis of Two Implantable Narcotic Delivery Systems," Journal of Pain and Symptom Management. vol. 6, No. 6, Aug. 1991. pp. 368-373.
Principles and Guidelines in Software User Interface Design, Deborah J. Mayhew, Chapter 9 Dialog Sryles: Direct Manipulation, copyright 1992, 17 pages.
Advertisement from HERCO, Are Control Rooms Obsolete? Dated Mar. 1971, 1 page and Mar. 1972, 1 page.
Electronics Feb. 1990 article entitled "Who Will Dominate the Desktop in the '90's?", 3 pages.
The Orange County Register No. 21, 1991 article entitled "Portable TV frees patients," 1 page.
Article by McMorris et al., "Are Process Control Rooms Obsolete?", Control Engineering dated Jul. 1971, pp. 42-47.
LabView® User Manual, Jan. 1990 Edition, cover page and pp. 2-1 through 2-36.
National Instruments' 1991 catalog entitled "IEEE-488 and VXIbus Control, Data Acquisition, and Analysis," cover page and pp. 1-1 through 1-13, 1-38, 4-68 and 4-69.
Abbot Laboratories Blue Line System Life Care® Model 4 Series System brochure, copyright 1990, 16 pages.
Operator's Manual for a CADD-Micro™ Ambulatroy Infusion Pump Model 5400, front cover and pp. ii-vi, pp. 1-55 and two back cover pages, copyright 1990.
Instruction Manual entitled "Quick Start for Speakerphone XT SVD", copyright 1996.
Bio Tek Instruments, Inc. Products Catalog. 32 pages. Apr. 1992.
Intel® document entitled, 28F001BX-T/28F001BX-B 1M(128K×8) CMOS Flash Memory, dated Mar. 1991, 28 pages.
Intel® document entitled, 28F008SA8MBIT (1MBITx) Flashtile™ Memory dated Mar. 1992, 28 pages.
Lahti W. et al., "Byte", pp. 311-318, Nov. 1990. "Store Data in a Flash".
"A Programable Infusion Pump Controller," 30th Annual Conference on Engineering in Medicine and Biology, Nov. 5-9, 1977 in Los Angeles, California, 11 pages.

"IV700 Service Manual." Valleylab, Inc. Boulder Colorado; Sep. 1988.

Designing the User Interface, Ben Shneiderman, Chapter 5 Direct Manipulation, Oct. 1993, 56 pages.

Operator's Manual for a CADD-Micro® Ambulatory Infusion Pump Model 5900, front cover and pp. ii-vi and 1-84, copyright 1993.

Provider® One Instruction Manual, Pancretec, Inc. (undated).

Sheppard, L.C., Computerbased Clinical Systems: Automation and Intergration, 39th Annual Conference on Engineering in Medicine and Biology, Baltimore, Maryland, Sep. 13-16, 1986, pp. 73-75.

Wilson R., "Integrated Circuits" of Computer Design, pp. 26-27, Jun. 1, 1989.

Zales, S et al., Microprocessors and Microsystems vol. 14, No. 8, pp. 543-549, Oct. 1990.

Intravenous propofol anaesthesia using a computerized infustion system, M. White and G.N.C. Kenny, Anaesthesia, 1990, vol. 45, pp. 204-209.

Health Devices, ECRI A Nonprofit Agency, vol. 17 No. 12, Dec. 1988.

Health Devices, ECRI A Nonprofit Agency, vol. 19 Nos. 3-4, Mar.-Apr. 1989.

Operator's Manual, Gemini® PC-1 Volumetric Infusion Pump/Controller imed® Aug. 16, 1990.

Model 929 Computer Controlled Volumetric Infusion Pump Operating Instructions imed® as submitted Feb. 28, 2008 in U.S. Appl. No. 11/981,788.

Pain Control Devices Gaining Acceptance, Will Expand-Analgesic Delivery Devices-Industry Overview, http://www.findarticles.com/articles/mi_m3498/is_n5_v55/ai_12257770, Sep. 29, 2004.

A Standard Microcomputer Linked to a Volume-Controlled Infusion Pump for Patient-Controlled Analgesia Research, Journal of Medical Engineering and Technology, G.W.A. Gillies, G.N.C. Kenny and C.S. McArdle, vol. 10, No. 2, Mar./Apr. 1986. pp. 55-57.

The P1073 Medical Information Bus, David F. Franklin and David V. Ostler (Oct. 1989).

IMED 980 Volumetric Infusion Pump Operator's Manual. 1992.

Improving Acute Care Use of Medical Device Data, Robert J. Kennelly, Chair, IEEE 1073 "Standard for Medical Device Communications" Committee, Eden Shores Consulting. 1992.

Health Devices, ECRI A Nonprofit Agency, Sep. 1991, vol. 20, No. 9.

Medtronic MiniMed Paradigm Link Owner's Guide, BD Logic, 2003.

M68HC11 E Series, HCMOS Microcontroller Unit, Motorola, Inc. 1993, 1996.

Health Devices, ECRI A Nonprofit Agency, Dec. 1989, vol. 18 No. 12.

Health Devices, ECRI A Nonprofit Agency, Dec. 1991, vol. 20 No. 12.

510 (k) Registration Documents for Registration of K87022 and K871728 (1987).

510 (k) Registration Documents for Registration of K863997 (1986).

Complaint for Patent Infringement (Exhibits 1-3); C.A. No. 03-776, *Medtronic Minimed, Inc.* v. *Deltec Inc.*, and *Smiths Medical Ltd.* Aug. 5, 2003.

First Amended Complaint for Patent Infringement (Exhibits 1-3); C.A. No. 03-776, *Medtronic Minimed, Inc.* v. *Deltec Inc. Smiths Group North America Inc. and Smiths Medical Ltd.* Nov. 3, 2003.

Answer and Counterclaims of Smiths Medical Md. Inc. (Exhibits 1-5); C.A. 03-776, *Medtronic Minimed, Inc.* v. *Deltec Inc., Smiths Group North America, Inc. and Smiths Group Pic.* Nov. 17, 2003.

Joint Claim Construction Statement (Exhibits 1-2); C.A. No. 03-776, *Medtronic Minimed, Inc.* v. *Smiths Medical Md, Inc.* Certificate of service Feb. 4, 2005.

Expert Response of Anthony Storace on behalf of Defendant Counterclaimant Smiths Medical Md., Inc. to The Expert Report Submitted by jack Goldberg on behlaf of Plaintiff Medtronic Minimed (Exhibits B-J); C.A. No. 03-776, *Medtronic Minimed Inc.* v. *Smiths Medical Md, Inc.* Jan. 14, 2005.

Medtronic Minimed's Reply Brief in Support of it's Motion for Summary Judgment of Non-Infringement of Claims 6 and 11 of Smiths '704 Patent (Exhibits A-B), *Medtronic Minimed Inc.* v. *Smith Medical Md, Inc.* Mar. 4, 2005.

Medtronic Minimed's Reply Brief in Support of its Motion for Summary Judgment of Invalidilty of Claims 6 and 11 of Smiths '704 Patent (Exhibits A-B); C.A. No. 03-776, *Medtronic Minimed Inc.* v. *Smiths Medical MD, Inc.* Mar. 4, 2005.

Defendant Smiths Medical Md. Inc. S. Answering Brief Responding to Medtronic Minimed Inc.'s Claim Construction Brief for U.S. Patent No. 6,241,704, C.A. No. 03-776, *Medtronic Minimed Inc.* V. *Smiths Medical Md. Inc.* Feb. 25, 2005.

Declaration of Anthony C. Roth in Support of Defendant-Counterclaim Plantiff Smiths Medical Md, Inc. 's Response Brief to Medtronic Minimed, Inc.'S Claim Construction Brief of U.S. Patent No. 6,241,704 (Exhibits A-H); C.A. No. 03776, *Medtronic Minimed Inc.* v. *Smith Medical Md, Inc.* Feb. 25, 2005.

Defendant Smiths Medical Md, Inc. 's Brief in Opposition to Medtronic Minimed, Inc 'S Motion for Summary Judgment of Invalidity of Claims 6 and 11 of Smiths Medical Inc. 's U.S. Patent No. 6,241,704; C.A. No. 03-776, *Medtronic Minimed, Inc.* v. *Smiths Medical Md. Inc.* Feb. 28, 2005.

Declaration of Anthony C. Roth in Support of Defendant-Counterclaim Plaintiff Smiths Medical Md, Inc. 's Brief in Opposition of Medtronic Minimed Inc. 'S Motion for Summary Judgment of invalidity of claims 6 and 11 of Smiths Medical Inc. 'S U.S. Patent 6,241,704 (Exhibits 1-7); C,A, No. 03-7769, *Medtronic Minimed Inc.* v. *Smiths Medical Md. Inc.* Feb. 28, 2005.

Expert Report of Jack Goldberg on behalf of Plaintiff Medtronic Minimed Pursuant to Fed R. Civ. P. 26(A)(2) (Exhibits A-F); C.A. No. 03-776, *Medtronic Minimed Inc.* v. *Smiths Medical Md. Inc.* Executed Dec. 15, 2004.

Opening Brief in Support of Defendant Smiths Medical, Inc.'s Propsed Claim Constructions for U.S. Patent Nos. 6,241,704; 6,554,065 and 6,554,798 (Exhibits 1-20); C.A. No. 03-776, *Medtronic Minimed, Inc.* v. *Smiths Medical Md, Inc.* Feb. 4, 2005.

Memorandum Opinion: C.A. No. 03-776, *Medtronic Minimed, Inc.* v. *Smiths Medical Md. Inc.* Jun. 1, 2005.

Order: C.A. No. 03-776; *Medtronic Minimed Inc.* v. *Smiths Medical Md. Inc.* Jun. 1, 2005.

Memorandum Opinion (Summary Judgment of Infringement of U.S. Patent Nos. 5,665,065 and 6,554,798), C.A. No. 03-776, *Medtronic Minimed Inc.* v. *Smiths Medical Md. Inc.* Jun. 16, 2005.

Examiner's first report No. 4 on Australian patent application No. 2005216321 dated Aug. 25, 2011. Australian Government IP.

Examiner's first report on Australian patent application No. 2007282069 dated Jul. 11, 2011. Australian Government IP.

Examiner's first report on Australian patent application No. 2007281512 dated Jul. 4, 2011. Australian Government IP.

Examiner's first report on Australian patent application No. 2007282071 dated Jul. 11, 2011. Australian Government IP.

European Office Action for European Application No. 07836379 dated Dec. 18, 2012.

Australian Office Action for Australian Application No. 2007282068 dated Dec. 17, 2012.

European Office Action for European Application No. 07836389 dated Dec. 18, 2012.

* cited by examiner

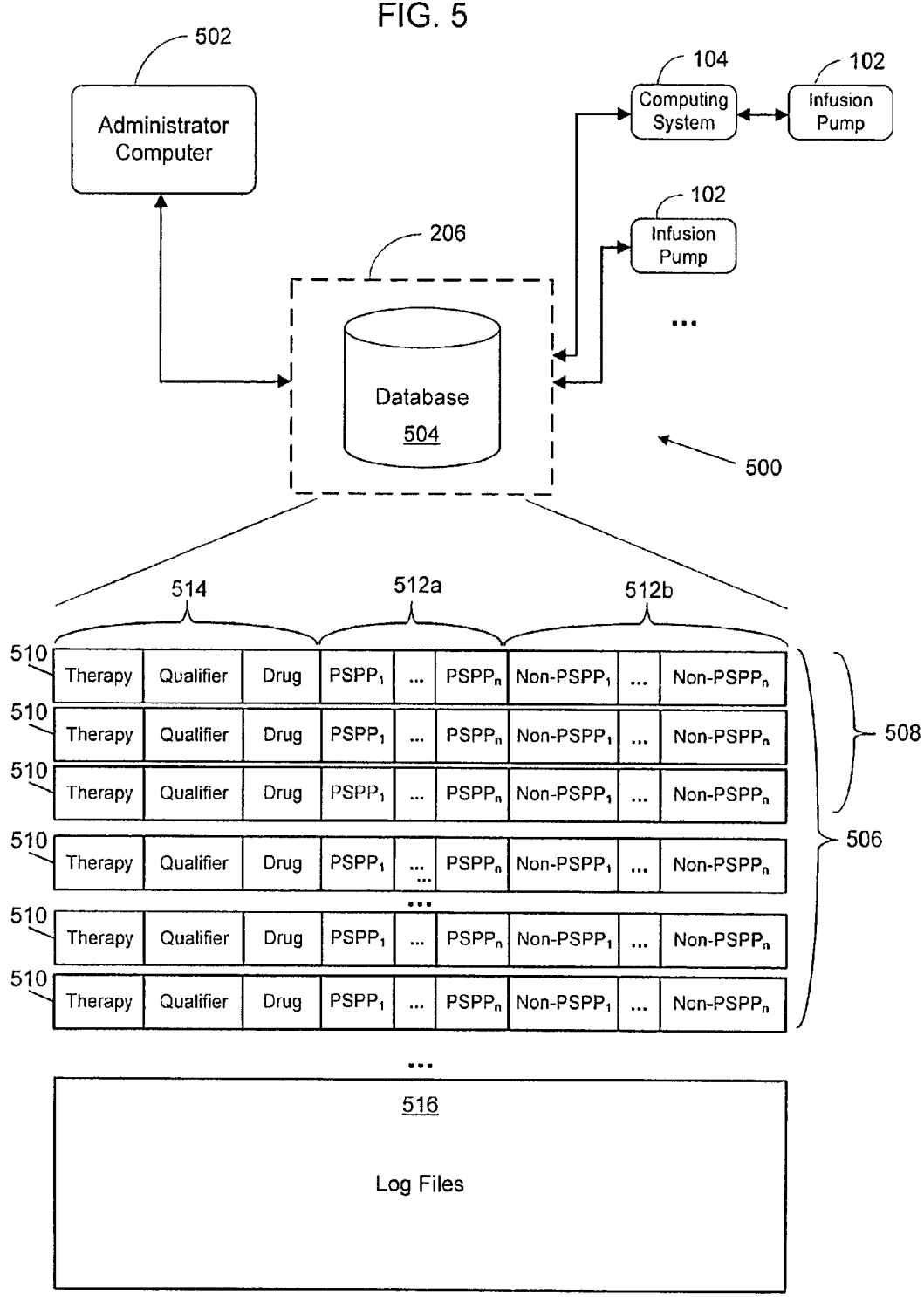

INTERFACE FOR MEDICAL INFUSION PUMP

REFERENCE TO CO-PENDING APPLICATION(S)

The present application claims priority to U.S. Provisional Patent Application Ser. No. 60/835,926, filed Aug. 3, 2006, the entire disclosure of which is hereby incorporated by reference.

BACKGROUND

Patients at hospitals and other care centers regularly require controlled drug intake as a part of the patient's prescribed therapy. One form of controlled drug intake is accomplished by infusing fluidic drugs with a medical infusion pump.

Medical infusion pumps, in general, provide regulated drug delivery to a patient. These pumps are used to deliver a selected drug or other therapeutic agent to a patient at a predetermined rate that is programmed into the pump. However, programming and managing such pumps can be difficult and cumbersome. Programming typically includes preloading a pump program into a pump and then entering pump parameters or data into the pump through a keypad that is directly in the pump. Each time the pump is programmed, the data must be reentered by hand.

Managing the status and locations of pumps also can be difficult. A single pump can be programmed for delivering different fluids in different therapies and in different locations within a hospital. Similarly, the status of a pump and alarms can be difficult to monitor because the pumps are often in locations other than where the caregiver is located and have small displays on which information can be difficult to see.

SUMMARY

According to a first aspect, a method of programming a medical infusion pump is disclosed. The method includes displaying a meter having two or more locations, each of the two or more locations representing a corresponding parameter value programmable into the medical infusion pump. The method further includes displaying an indicator having a selectable positional relationship to the meter, the selected position corresponding to a parameter value.

According to a second aspect, an apparatus for programming a medical infusion pump is disclosed. The apparatus includes a memory configured to store at least two parameter values programmable into the medical infusion pump. The apparatus also includes a monitor. The apparatus further includes a programmable circuit in electrical communication with the memory and the monitor. The programmable circuit is programmed to display on the monitor a meter having two or more locations, each of the two or more locations representing a corresponding parameter value programmable into the medical infusion pump. The programmable circuit is also programmed to display an indicator having a selectable positional relationship to the meter, the selected position corresponding to a parameter value.

According to a third aspect, a method of programming a medical infusion pump is disclosed. The method includes displaying a slider bar having a plurality of locations, each of the plurality of locations representing a corresponding parameter value programmable into the medical infusion pump, the slider bar including a warning region located along a portion of the slider bar. The method also includes displaying an indicator movable along the slider bar to a selected position, the selected position corresponding to a parameter value. The method further includes downloading the parameter value to the medical infusion pump. The method also includes, upon detection of movement of the indicator to a position within the warning region, issuing an alert.

According to yet another aspect, an apparatus for programming a medical infusion pump is disclosed. The apparatus includes a memory configured to store at least two parameter values programmable into the medical infusion pump and one or more hard limits. The apparatus also includes a monitor. The apparatus further includes a programmable circuit in electrical communication with the memory and the monitor. The programmable circuit is programmed to set one or more hard limits to define a range of permissible parameter values for programming a medical infusion pump. The programmable circuit is also programmed to display on the monitor a meter having two or more locations, each of the two or more locations representing a corresponding parameter value within the range. The programmable circuit is further programmed to display on the monitor an indicator having a positional relationship to the meter, the position corresponding to a parameter value within the range.

BRIEF DESCRIPTION OF THE DRAWINGS

FIG. 5 is an exemplary infusion pump network according to a possible embodiment of the present disclosure;

FIG. 14 is one example of a computer user interface prescription order form display screen in accordance with the present disclosure;

FIG. 16 is one example of a computer user interface qualifier selection screen in accordance with the present disclosure;

FIG. 17 is one example of a computer user interface drug selection screen in accordance with the present disclosure;

FIG. 18 is one example of a computer user interface drug delivery tab in accordance with the present disclosure;

DETAILED DESCRIPTION

Figure 1:
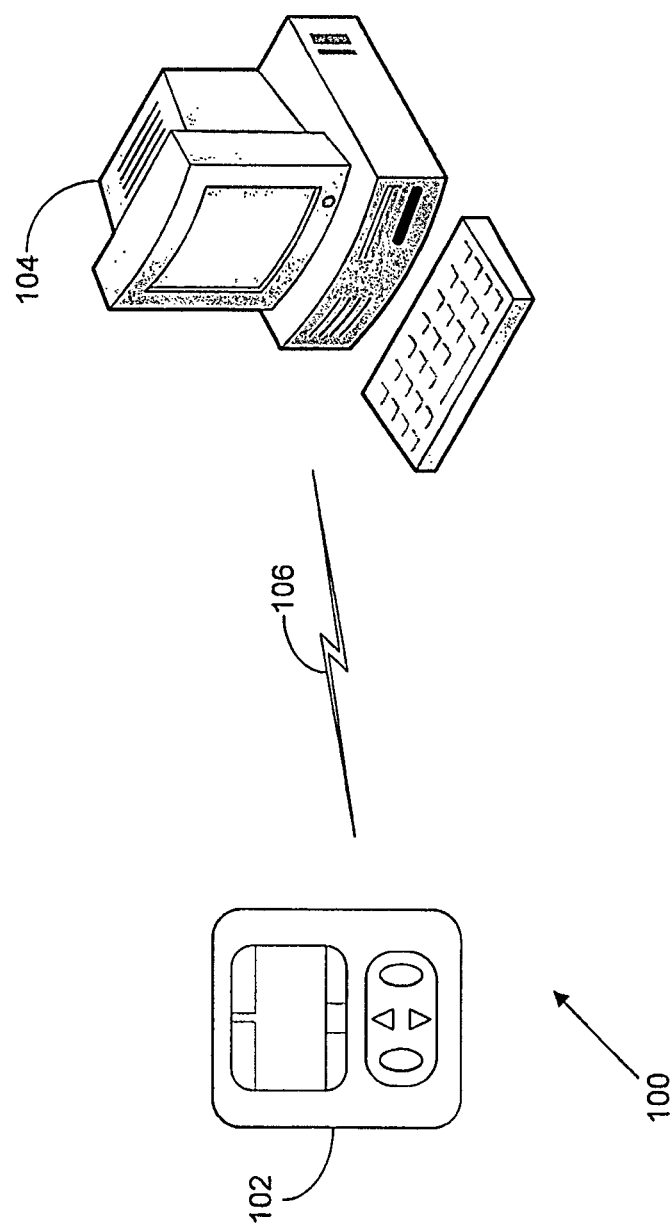
FIG. 1 illustrates a pump-computer communication system according to a possible embodiment of the present disclosure.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The following discussion is intended to provide a brief, general description of a suitable computing environment in which the invention may be implemented. Although not required, the invention will be described in the general context of computer-executable instructions being executed by a computer, for example, a hand held computer, a personal computing system, or a medical infusion pump. The structure, creation, and use of a message store hierarchical folder structure are described after the discussion of an exemplary operating environment.

Additionally, the logical operations of the various embodiments of the invention described herein are implemented as: (1) a sequence of computer implemented operations running on a computing system; and/or (2) interconnected machine modules within the computing system. Modules represent functions executed by program code such as commonly available programming languages or as the code found in a dynamic-link library (DLL). The implementation used is a matter of choice dependent on the performance requirements of the pump and the computing systems with which it interfaces. Accordingly, the logical operations making up the embodiments of the invention described herein can be referred to alternatively as operations, modules, and the like.

FIG. 1 illustrates an exemplary embodiment of an infusion pump network 100 having a medical infusion pump 102, a computing system 104, and a communications link 106. The medical infusion pump 102 is configured to deliver therapeutic fluids, such as drugs, saline, or nutrition to a patient. Examples, of medical infusion pumps 102 include ambulatory pumps, stationary pumps, and pole mounted pumps.

The computing system 104 is configured to execute computer-readable instructions, such as computer software. The computing system 104 can be located in a variety of locations such as the point of care (POC) where a patient is being treated, in a healthcare facility at a location remote from the POC, or even at an off-site location remote from the healthcare facility itself. In further embodiments, the medical infusion pump 102 acts as the computing system 104.

In the exemplary embodiment, the computing system 104 is programmed to generate and store pump protocols for execution in the context of a pump application program. Each pump protocol includes a series of pump parameters. Pump parameters refer to settings that define an operational aspect of a medical infusion pump. The pump parameters dictate the control of the pump.

Pump protocols are collections of these pump parameters defining the variable operational characteristics of a medical infusion pump during application of a specific therapy, qualifier, and drug. The pump protocol includes a listing of operational parameters to be included in the pump, and correlates to an index for referring to a specific protocol containing a specific set of pump parameters. The index can be associated with a therapy, qualifier, and drug, and is either contained within the protocol or associated with a specific protocol. The pump protocol includes patient specific pump parameters and non-patient specific pump parameters. Patient specific pump parameters refer to those parameters which are set on a patient-by-patient basis, and for example include the basal delivery rate or bolus amount. Non-patient specific pump parameters refer to those parameters which are set for the pump to perform specific tasks, and do not account for the specific patient to which they are applied. These parameters are generally related to the pump, the infusion pump network, or the medical care to be provided by the pump and/or pump network. Non-patient specific pump parameters can include, for example, a range of permissible values for basal delivery, a range of values and patterns for basal delivery, a range of permissible values for boluses, a range of values and patterns for extended boluses, a starting value within a particular range of values, alarm values, protocols for data communication, and various flag settings.

A pump application program is a program having instructions (e.g., executable code, rules, and/or data) that control operation of the pump for a specific therapy or type of delivery (e.g., continuous delivery, intermittent delivery, pain control, chemotherapy, total parenteral nutrition, etc.). For example, a pump application program might contain instructions that define operation of a pump to accomplish various of the pump parameters. Pump application programs include, for example, pump protocols including both patient specific and non-patient specific pump parameters, and instructions for allocating memory, user interfaces, or algorithms for monitoring various sensors and driving a motor for the pump mechanism.

The communications link 106 connects the pump 102 and computing system 104. In various embodiments, the communications link 106 can include serial or parallel connections, wired or wireless connections, and a direct or networked connection to a computer. Additionally, the pump 102 and the computing system 104 can communicate using any protocol appropriate for data communication. Examples of network connections to a computer include Intranet, Internet, and LAN (e.g., Ethernet). Examples of wired connections to a computer include USB, RS-232, Firewire, and power-line modem connection. Examples of wireless connections include bluetooth, 802.11a/b/g, infrared (IR), and radio frequency (RF).

Figure 2:
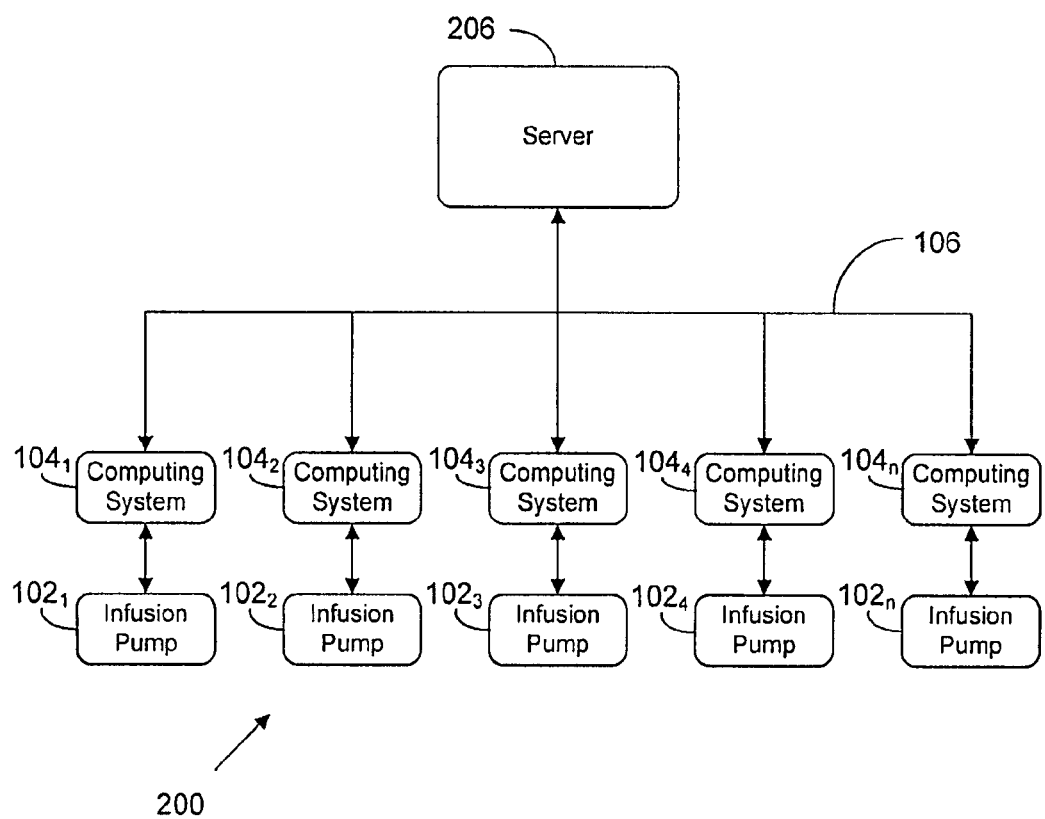
FIG. 2 illustrates an infusion pump network according to a possible embodiment of the present disclosure.

FIG. 2 illustrates an exemplary embodiment of an infusion pump network 200 having a server 206 networked with a plurality of computing systems $104_1$-$104_n$. The network 200 can be any wired or wireless network that enables data communication between the server, computing systems, and medical infusion pumps. Examples of networks include the Internet, Intranets, and LANs. Each computing system 104 can communicate with a medical infusion pump $102_1$-$102_n$ through a communication link 106.

In the exemplary embodiment, the individual computing systems $104_n$ execute software for generating and managing pump application programs and sets of pump operating parameters. The pump application programs and sets of pump operating parameters are stored on the server 206 so they can be accessed by other individual computing systems $104_n$. The individual computing systems $104_n$ are also programmed to retrieve previously created pump application programs and sets of pump operating parameters that are stored on the server 206 for viewing, editing, and downloading to medical infusion pumps $102_n$.

In alternative embodiments, the medical infusion pumps $102_n$ can directly access the server to retrieve pump application programs and sets of pump operating parameters. For example, the medical infusion pumps $102_n$ can be loaded with client software such as a web browser and communicate directly with the network 200, either through a wired or wireless connection as described herein.

In other alternative embodiments, one or more of the computing systems is not configured to communicate directly with a medical infusion pump $102_n$, but rather provides administrative access to the server 206 for generating, viewing, and editing pump application programs and sets of pump operating parameters. Additionally, servers, workstations, and other computing systems unaffiliated with the medical infusion pumps $102_n$ can be included in the network 200.

In yet other alternative embodiments, the software is executed in the server 206. For example, the server functions as an application service provider that communicates user interface and other data entries in mark-up language such as HTML or some other language or protocol that allows a user to execute software from a remote location. In these embodiments, the server 206 can function as an application service provider in which the server provides access to the software for generating and storing pump application programs and pump protocols that a user can create and download to a medical infusion pump. For example, the server 206 could be located at a pump manufacture, pharmaceutical manufacture, pharmacist, or some other third party separate from the user. The server 206 in such an embodiment can be accessed either from an individual computing system 104 or by a medical infusion pump 102 that has networking capabilities and client software.

Example embodiments of a server 206 and a medical infusion pump 102 having a web browser are disclosed in U.S. patent application Ser. No. 11/066,425, which was filed on Feb. 22, 2005 and is entitled Server for Medical Device, the entire disclosure of which is hereby incorporated by reference.

Figure 3:
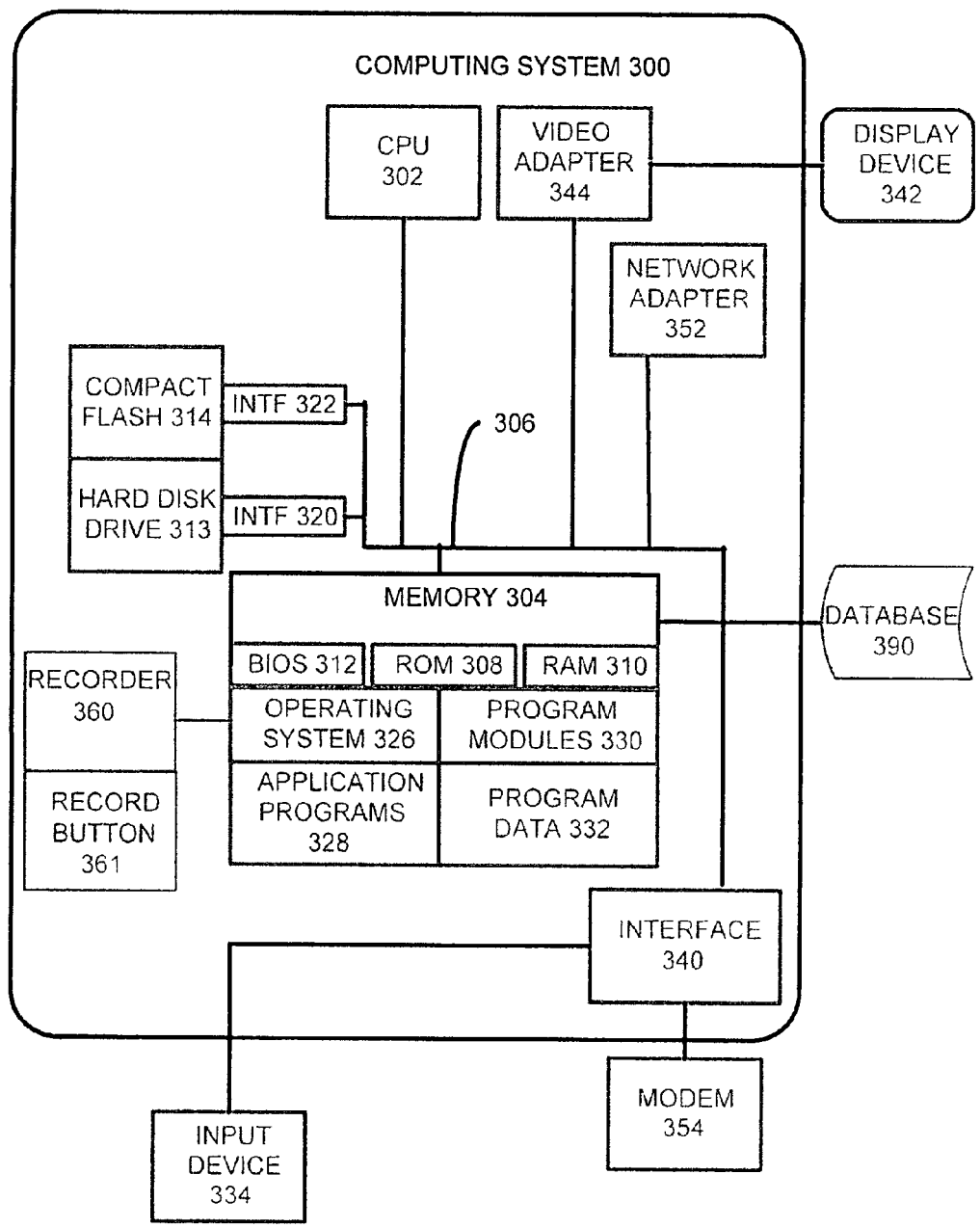
FIG. 3 illustrates the architecture of a computing system that can be used to implement aspects of the present disclosure.

FIG. 3 illustrates an exemplary architecture that can be used to implement aspects of the present disclosure, including the computing systems 104 and the server 206. The computing system architecture includes a general purpose computing device in the form of a computing system 300. The computing system 300 can be used, for example, as the computing system or server of FIG. 2, and can execute program modules included in the administrative software or user software disclosed below.

The computing system 300 including at least one processing system 302. A variety of processing units are available from a variety of manufacturers, for example, Intel or Advanced Micro Devices. The computing system 300 also includes a system memory 304, and a system bus 306 that couples various system components including the system memory 304 to the processing unit 302. The system bus 306 may be any of a number of types of bus structures including a memory bus, or memory controller; a peripheral bus; and a local bus using any of a variety of bus architectures.

The system memory 304 can include read only memory (ROM) 308 and random access memory (RAM) 310. A basic input/output system 312 (BIOS), containing the basic routines that help transfer information between elements within the computing system 300, such as during start up, is typically stored in the ROM 308.

The computing system 300 can also include a secondary storage device 313, such as a hard disk drive, for reading from and writing to a hard disk (not shown), and/or a compact flash card 314.

The hard disk drive 313 and compact flash card 314 are connected to the system bus 306 by a hard disk drive interface 320 and a compact flash card interface 322, respectively. The drives and cards and their associated computer readable media provide nonvolatile storage of computer readable instructions, data structures, program modules and other data for the computing system 300.

Although the exemplary environment described herein employs a hard disk drive 313 and a compact flash card 314, other types of computer-readable media, capable of storing data, can be used in the exemplary system. Examples of these other types of computer-readable mediums include magnetic cassettes, flash memory cards, digital video disks, Bernoulli cartridges, CD ROMS, DVD ROMS, random access memories (RAMs), or read only memories (ROMs).

A number of program modules may be stored on the hard disk 313, compact flash card 314, ROM 308, or RAM 310, including an operating system 326, one or more application programs 328, other program modules 330, and program data 332. A user may enter commands and information into the computing system 300 through an input device 334. Examples of input devices might include a keyboard, mouse, microphone, joystick, game pad, satellite dish, scanner, digital camera, touch screen, and a telephone. These and other input devices are often connected to the processing unit 302 through an interface 340 that is coupled to the system bus 306. These input devices also might be connected by any number of interfaces, such as a parallel port, serial port, game port, or a universal serial bus (USB). Wireless communication between input devices and interfaces 340 is possible as well, and can include infrared, bluetooth, 802.11a/b/g, cellular, or other radio frequency communication systems. A display device 342, such as a monitor or touch screen LCD panel, is also connected to the system bus 306 via an interface, such as a video adapter 344. The display device 342 might be internal or external. In addition to the display device 342, computing systems, in general, typically include other peripheral devices (not shown), such as speakers, printers, and palm devices.

When used in a LAN networking environment, the computing system 300 is connected to the local network through a network interface or adapter 352. When used in a WAN networking environment, such as the Internet, the computing system 300 typically includes a modem 354 or other communications type, such as a direct connection, for establishing communications over the wide area network. The modem 354, which can be internal or external, is connected to the system bus 306 via the interface 340. In a networked environment, program modules depicted relative to the computing system 300, or portions thereof, may be stored in a remote memory storage device. It will be appreciated that the network connections shown are exemplary and other methods of establishing a communications link between the computing systems may be used.

The computing system 300 might also include a recorder 360 connected to the memory 304. The recorder 360 includes a microphone for receiving sound input and is in communication with the memory 304 for buffering and storing the sound input. The recorder 360 also can include a record button 361 for activating the microphone and communicating the sound input to the memory 304.

A computing device, such as computing system 300, typically includes at least some form of computer-readable media. Computer readable media can be any available media that can be accessed by the computing system 300. By way of example, and not limitation, computer-readable media might comprise computer storage media and communication media.

Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by the computing system 300.

Communication media typically embodies computer-readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media. Computer-readable media may also be referred to as computer program product.

Figure 4:
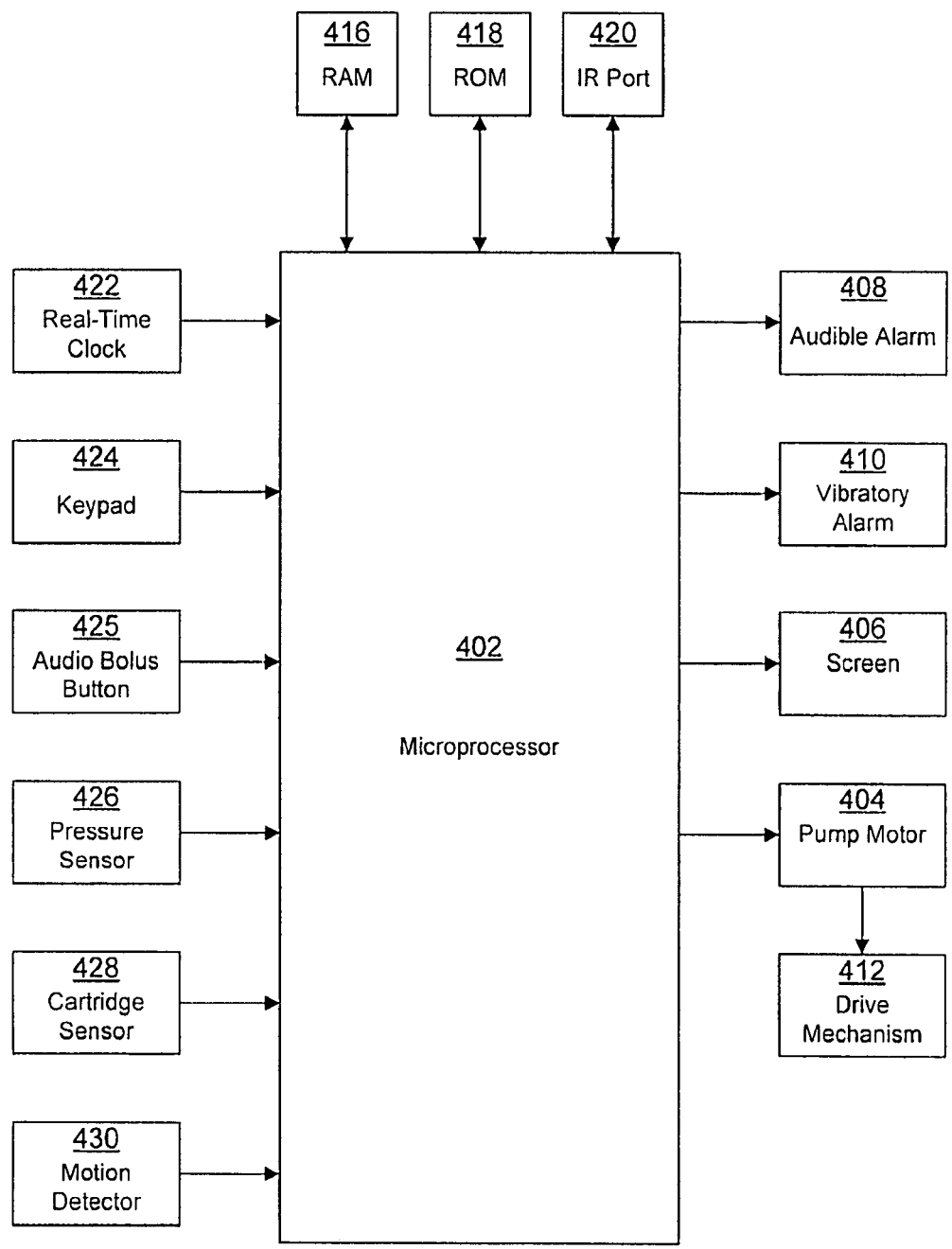
FIG. 4 illustrates the architecture of a pump that can be used to implement aspects of the present disclosure.

FIG. 4 illustrates the architecture of a medical infusion pump 400 that can be used to implement aspects of the present disclosure. A microprocessor 402 is in electrical communication with and controls a pump motor 404, a screen 406, an audible alarm 408, and a vibratory alarm 410. Other embodiments can use a microcomputer, or any other type of programmable circuit, in place of the microprocessor.

The pump motor 404 drives a drive mechanism 412. The drive mechanism 412 delivers the therapeutic fluid to a patient. The drive mechanism can be connected to a plunger system, a peristaltic drive mechanism, or another type of fluid delivery system.

The screen 406 can have many different configurations such as an LCD screen. The screen 406 displays a user interface that presents various items of information useful to a patient or caregiver. The audible alarm 408 is a beeper, and an alarm provides actual alarms, warnings, and reminders. Similar to other portable electronic devices such as a cellular telephone, the vibratory alarm 410 provides an alarm to either supplement the audio alarms or replace the audio alarm when an audible beep would be disruptive or not heard. A user can selectively enable or disable the audible 408 and vibratory 410 alarms. In one possible embodiment, however, both the audible 408 and vibratory 410 alarms cannot be disabled at the same time.

The microprocessor 402 is in electrical communication with both a random access memory (RAM) 416 and a read only memory (ROM) 418, which are onboard the pump 400 but external to the microprocessor 402 itself. In one possible embodiment, the microprocessor 402 includes internal memory as well. The RAM 416 is a static RAM stores that data that can change over time such as pump settings and a historical log of events experienced by the medical infusion pump 400. The ROM 418 stores code for the operating system and the application programs. The ROM 418 can be any type of programmable ROM such as an EPROM. In one possible embodiment, the RAM 416 has 500 kilobytes of memory capacity and the ROM 418 has 2 megabytes of memory capacity.

An infrared (IR) port 420 is in electrical communication with the microprocessor. As explained in more detail below, the IR port 420 provides data communication with an external device such as a computer for programming an application program, programming pump settings, and downloading historical data logs. The medical infusion pump 400 can include other types of communication ports in place of or in addition to the IR port 420. Examples of other possible communication ports include a radio frequency (RF) port or a port that provides a hard-wired data communication link such as an RS-232 port, a USB port, or the like.

A real-time clock 422 provides a clock signal to the microprocessor 402. An advantage of having a real-time clock 422 is that it provides the program with the actual time in real-time so that the programs executed by the medical infusion pump can track and control the actual time of day that drug delivery and other events occur. Various durations described here are used for alerts, alarms, reminders, and other functions. In one possible embodiment, the timers are formed by the real-time clock 422 and software executed by the microprocessor 402.

A keypad 424 also provides input to the microprocessor 402. Although other possible types of keypads are possible, one type of keypad has four buttons and is a membrane-type of keypad, which provides resistance to water and other environmental conditions. The keypad 424 contains soft keys for which the function of the keys can change as a user executes different menu selections and commands.

An audio bolus button 425 optionally provides input to the microprocessor 402. The audio bolus button 425 can program the pump 400 to audibly administer a bolus of drugs or other therapeutic fluids without requiring visual confirmation using the pump. In an example embodiment, the audio bolus button 425 can be pressed a series of times to trigger bolus delivery of a selected volume, based on a preprogrammed trigger granularity. A single button press can represent a bolus of 5 grams, as selected by a user, and subsequent presses of the audio bolus button can represent multiples thereof.

Other inputs into the microprocessor 402 can include an occlusion sensor 426, which is sensitive to occlusions in the therapeutic fluid delivery line; a cartridge sensor 428, which is sensitive to the presence of a therapeutic fluid cartridge; and a motion detector 430, which detects motion of a gear (not shown) in the drive mechanism 412. In an exemplary embodiment, the cartridge sensor 428 includes one or more sensors configured to detect insertion of a therapeutic fluid cartridge. The pump 400 can detect the type of cartridge present via a mechanical interface, and can include in the pump software instructions regarding operation in conjunction with the cartridge. Examples of cassette sensing features are described, for example, in U.S. Pat. No. 5,531,697, filed on Apr. 15, 1994, issued on Jul. 2, 1996, and entitled Systems and Methods for Cassette Identification for Drug Pumps.

FIG. 5 illustrates a schematic architecture of a medical infusion pump network 500 according to an exemplary embodiment. The medical infusion pump network 500 includes an administrator computer 502 communicatively connected to the server 206 of FIG. 2, which includes a database 504. The medical infusion pump network 500 also includes one or more medical infusion pumps 102 and computing systems 104.

The administrator computer 502 and computing systems 104 are systems such as those described above in conjunction with FIG. 3. The administrator computer 502 includes administrative software installed on or accessible to the computer for generating one or more libraries 508 of pump protocols 510. An exemplary embodiment of the administrative software is described below in FIGS. 7-25.

In the present disclosure, libraries refer to collections of pump protocols generated using the administrative software described herein. Libraries can be stored in files, databases, or other data structures. Libraries contain pump protocols as well as indices pointing to the protocols, and are loaded in user software to select a specific pump protocol for operation of a medical infusion pump.

The computing systems 104 include user software for accessing one or more libraries 508 of protocols 510 and programming a medical infusion pump 102 with a protocol 510 or a library 508. In one possible embodiment, the computing systems 104 are optional in that the user software resides directly on the medical infusion pumps 102. An exemplary embodiment of the user software is described below in FIGS. 26-41.

The medical infusion pumps 102 connect either to a computing system 104 or directly to the server 206, and are described above in conjunction with FIG. 4. In a first embodiment, the medical infusion pumps 102 are configured to accept a pump protocol from the server 206 or the computing system 104. In a second embodiment, the medical infusion pumps 102 are configured to accept a library 508 of pump protocols 510 directly from the server 206 or from the computing system 104.

The database 504 contains pump protocol data 506 and log files 516. The pump protocol data 506 forms a plurality of libraries 508 which in turn each include a number of protocols 510. Each protocol 510 is stored as a data record, and includes a set of parameters, including patient specific pump parameters 512a and non-patient specific pump parameters 512b, as described above. Each library 508 can contain one or more pump protocols 510.

The log files 516 include log data regarding access and usage of the libraries 508, and can include information related to the administrator computer 502, the medical infusion pumps 102, or the computing systems 104 authorized to connect to the server 206. In one possible embodiment, the log files include access records, which record instances in which medical infusion pumps access a library 508 on the server 206.

Figure 6A:
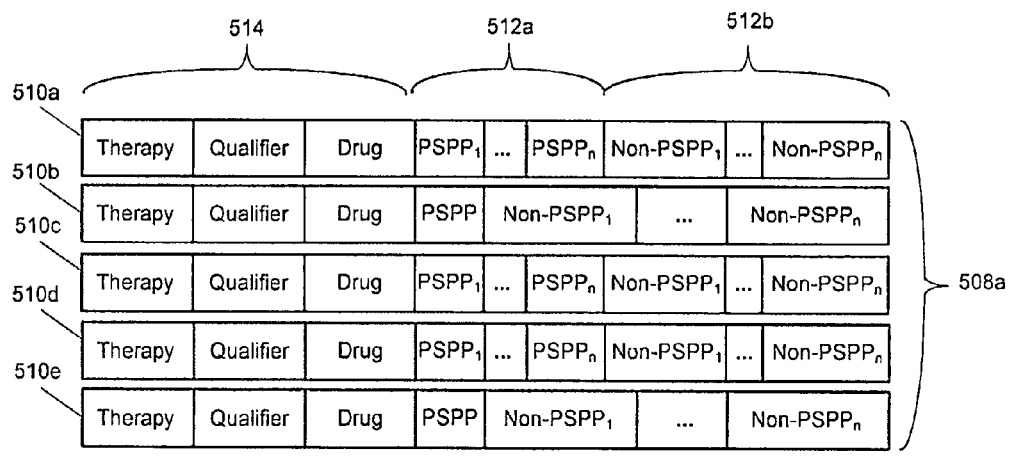
FIG. 6A is an exemplary data structure for a pump protocol library according to a possible embodiment of the present disclosure.
Figure 6B:
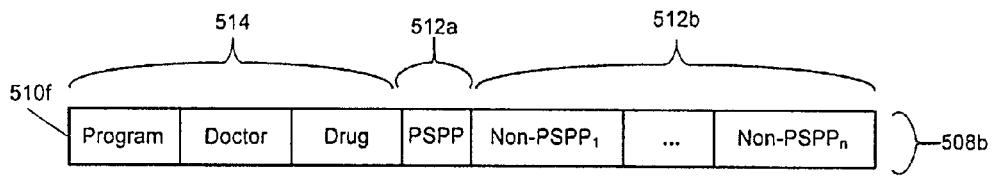
FIG. 6B is an exemplary data structure for a pump protocol library according to a possible embodiment of the present disclosure.
Figure 6C:
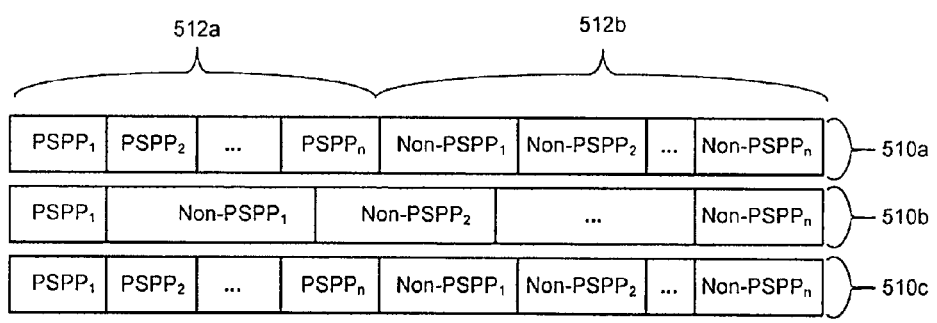
FIG. 6C is an exemplary data structure for pump protocols according to a possible embodiment of the present disclosure.

FIGS. 6A-6C illustrate exemplary data sets accepted by medical infusion pumps 102. The specific data set accepted by a medical infusion pump 102 is dependent upon that pump, but in various embodiments, the pumps accept data sets representing pump libraries, pump protocols, or pump programs. FIG. 6A shows a library 508 in greater detail. The library 508 can be loaded into the memory of a medical infusion pump 102, allowing a user of the pump to select a protocol for operation. The library 508 includes a number of protocols 510, which include patient specific pump parameters 512a, non-patient specific pump parameters 512b, and an index 514. The number of protocols 510 within a given library can vary, and depends upon the number defined using the administrative software.

The total number of pump parameters 512a-512b remains constant for each particular model of pump, but can vary between types of pumps. Additionally, the pump parameters 512a-512b can be configured in a number of formats within each protocol 510 for the same type of pump. For example, the number of patient specific pump parameters 512a can vary between protocols due to the specific type of drug and therapy applied. For example, a protocol defining a continuous drug delivery may only require a single patient specific protocol, namely, the drug delivery rate. In another example, a protocol defining intermittent drug delivery may require additional patient specific pump parameters, such as the time between drug delivery phases, a bolus amount, patient bolus amounts, and other parameters. The number of non-patient specific pump parameters 512b represents the difference between the total number of parameters programmable into a pump and the number of patient specific pump parameters 512a as dictated by the therapy and drug applied.

The index 514 can be any generic index referencing a specific location within the library. Each index is unique within the library, although another library may contain the same index and relate that index to a different set of pump parameters contained within that library. In the exemplary embodiment shown, the index 514 includes therapy, qualifier, and drug regions. By selecting a combination of a therapy, a qualifier, and a drug, a user of the system can select one of the protocols 510 from the library 508. Therapies, as referred to herein, are the methods of patient treatment for diseases or generalized rehabilitation. For example, a therapy can be an epidural treatment or patient-controlled analgesia. Qualifiers include factors affecting the administration of a therapy, such as weight, age, or sensitivity of a patient to a specific therapy. Drugs refer to any therapeutic fluids deliverable by a medical infusion pump.

Each of the protocol entries on the server can be assigned an identification code in order to ensure that the medical infusion pumps access a correct library and/or protocol, and that the protocols on the medical infusion pumps and computing systems associated with the server 206 of FIG. 5 are up to date. These identification codes are generated by the server and stored in conjunction with the protocol in the server 206, as well as in the medical infusion pump 102 and/or its associated computing system 104. The identification codes can be generated using globally unique identifiers (GUID), and are used to track the specific protocol and/or library accessed by each pump 102 or computing system 104 in the database 504. A GUID is a 128-bit pseudo random number used to provide a statistically unique identifier for corresponding the protocol on the pump 102 to the protocol as stored in the server 206. The GUID can be generated by the server 206 and transmitted alongside the protocol and/or library when transmitted to the computing system 104 or infusion pump 102. The server copy of the GUID can be stored alongside the protocol in the database 504, and the pump copy can be stored in RAM in the medical infusion pump 102 or computing system 104. Each time the medical infusion pump 102 or computing system 104 accesses the protocol on the server 206, the GUID assigned to that protocol as stored in the pump 102 or computing system 104 can be matched to the protocol as stored in the database 504 to ensure that the correct protocol is accessed. Different protocols in different libraries can use the same index of therapy, qualifier, and drug, and can be stored in the same database, but have a unique GUID and are therefore uniquely identifiable. In a possible embodiment, the GUID system can be used in conjunction with user access control systems, such as are disclosed in conjunction with both the user software and administrative software, below. In a further embodiment, a new GUID can be generated and associated with each protocol when first created, or optionally each time the protocol is edited using administrative software, such as is described below.

FIG. 6B illustrates a second possible embodiment of a library 508. The library 508 contains a number of protocols 510, which, as in FIG. 6A, include patient specific pump parameters 512a, non-patient specific pump parameters 512b, and an index 514. The number of protocols 510 included in each library 508 may vary, so the number of protocols 510 in the library 508 of FIG. 6B may be different from the number of protocols in the library shown in 6A. In the embodiment shown, the library 508 contains one protocol 510. Additionally, one or more of the therapy, qualifier, and drug regions in the index 514 can be replaced by other index criteria, such as locations, pump programs, doctor identification, or other indexable criteria capable of referring to a unique pump protocol within the library. In the example shown, the "therapy" region is used to select a pump program, such as a continuous delivery program, an intermittent delivery program, or a specific type of program such as a pain management program. The "qualifier" region is used to select a doctor, and may be the name of a doctor using the infusion pump network of FIG. 5.

FIG. 6C illustrates a series of possible pump protocols 510a-510c. The pump protocols 510a-510c incorporate patient specific pump parameters 512a and non-patient specific pump parameters 512b. Protocols 510 are specific to a pump 102, in that the pump has a specific number and type of parameters that are programmable. Therefore, the total number of pump parameters remains constant. However, the number of patient specific pump parameters 512a can vary depending upon the protocol selected for programming into the pump, which in turn dictates that the number of non-patient specific pump parameters 512b varies as well. In a possible embodiment, one of the protocols 510 is selected using a computing system 104 or infusion pump 102. If selected using the computing system, the protocol is then programmed into the medical infusion pump 102.

In another possible embodiment, the pump protocol 510 is selected using the infusion pump 102 or the computing system 104. The pump protocol 510 is then incorporated into a pump program to provide a set of instructions dictating the operation of a medical infusion pump 102 according to the protocol 510. The complete pump program is then downloaded into the pump 102. In yet another possible embodiment, the pump program is downloaded to the pump 102 at a different time from the pump protocol 510. In still a further embodiment, multiple pump programs reside within the pump 102, and the pump protocol 510 contains a parameter which dictates which pump program is to be used. In a further embodiment, the pump program within the pump is altered based on one or more of the pump parameters included in the pump protocol 510.

Figure 7:
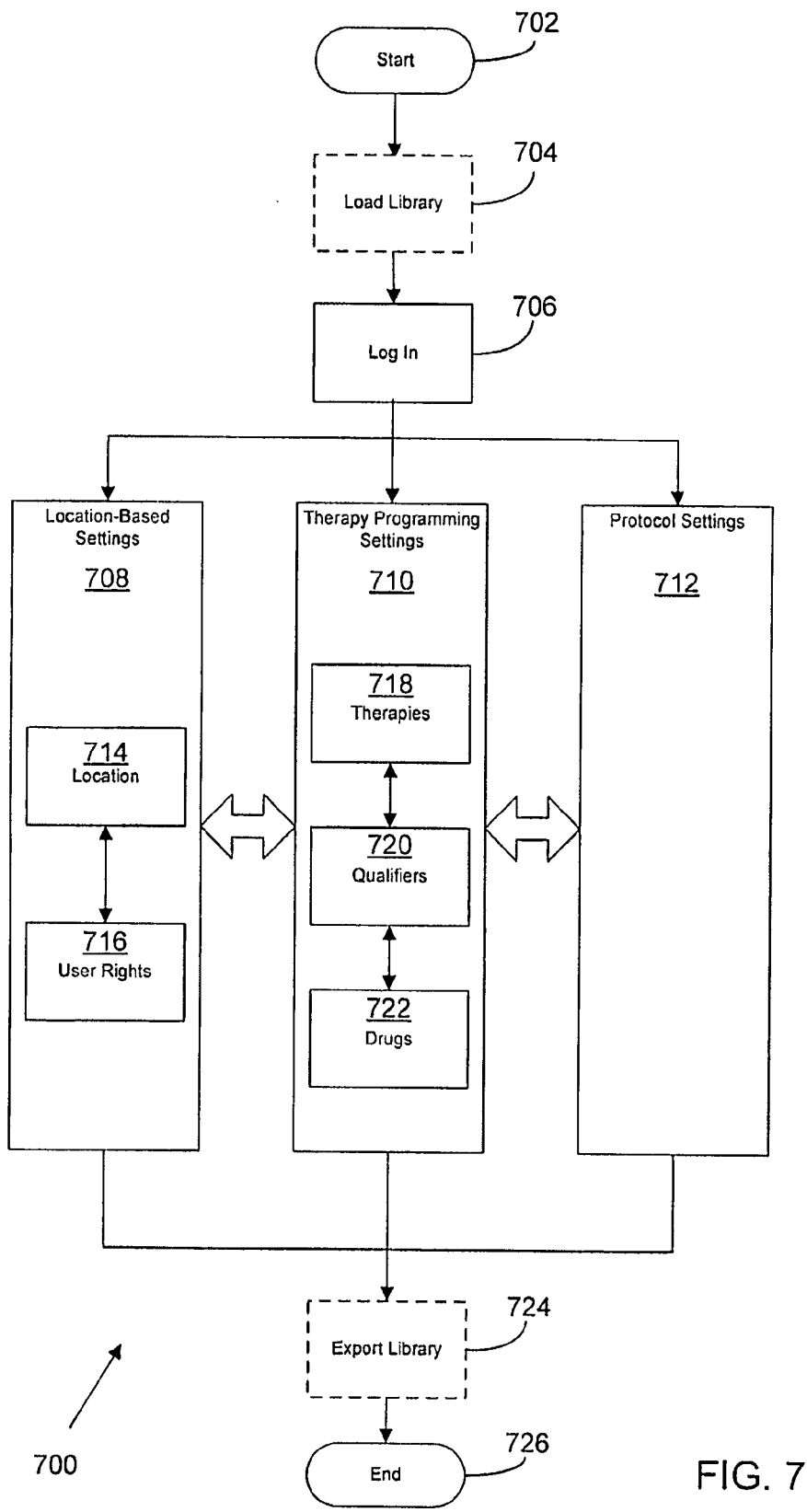
FIG. 7 is an exemplary architecture of administrative software for setting global pump protocols according to a possible embodiment of the present disclosure.

FIG. 7 illustrates exemplary architecture of administrative software 700 for generating one or more libraries of pump protocols. The software 700 can operate within the server 206, pump 102, computing system 104, or a combination thereof.

The administrative software 700 allows a user, for example a doctor, nurse, pharmacist, or other caregiver, to create, define, and edit pump application programs and protocols for execution in and control of medical infusion pumps 102. For example, the administrative software 700 can generate protocols and programs that can be loaded using the user software described in FIGS. 26-41, below.

The administrative software 700 provides protocol-based programming of medical infusion pumps in which the user creates a pump application program by designating a particular therapy and other criteria such as a location and qualifiers (e.g., patient age, weight, skin surface area). Once criteria are selected, the administrative software 700 applies rules and other logic that assembles sets of pump parameters into a pump protocol. For example, the administrative software 700 might be used to select one delivery pattern and enable bolus delivery if the selected therapy is for delivering pain medication and another delivery pattern and not enable bolus delivery if the selected therapy is for parenteral nutrition. In another example, the administrative software 700 might be used to select one range of permissible delivery rates if one of the criteria indicates the patient is an adolescent and different range of permissible delivery rates if the patient is an adult.

Other embodiments permit programming a medical infusion pump 102 without using therapy-based programming. Additional embodiments of protocol- or therapy-based programming is discussed in more detail in U.S. patent application Ser. No. 11/003,147, filed on Dec. 3, 2004 and entitled Programming Medical Pumps with Electronic Standing Order Template, the entire disclosure of which is hereby incorporated by reference.

Operation of the software 700 begins at a start module 702. The start module 702 corresponds to initial execution of the administrative software by clicking on an icon on the computer or by some other mechanism for executing software. Upon startup, the software 700 connects to a library loaded in the database 504 of FIG. 5.

Following the start module, operational flow optionally proceeds to a load library module 704, which allows a user to access a listing of library files available to the administrative software 700. The library files contain one or more libraries, which in turn contain a collection of pump protocols as described above. The collection of library files can be stored in the server 206 or in one or more individual computing systems 102. The load library module 704 allows the user to select a library file containing one or more libraries for viewing, editing, and downloading to a medical infusion pump 102. If a user does not want to download or otherwise access an existing library, it can selectively bypass the load library module 704. An example of when a user bypasses the load library module 704 is if the user plans to only create a new library or edit one or more protocols within the currently loaded library. In an alternative embodiment, the software always executes the load library module 704 and the user then selectively chooses whether to load any previously created libraries via a stored library file.

Following the start module 702 and optional load library module 704, operational flow proceeds to a login module 706. The login module 706 regulates user rights in the software 700. User rights define access levels to the currently connected library in user software, and are configurable for users such as doctors, nurses, or other caregivers. Based on the user rights assigned to a caregiver, that user will have a set access level allowing the user to view, add, or edit pump libraries within the user software, described in detail below. Access levels can be set according to a variety of criteria. Examples include the type of caregiver (e.g., physician, nurse, pharmacist), location (e.g., hospital, clinic, pharmacy, manufacturer), or a particular department within a location.

In possible embodiments, different access levels also provide different rights with respect to a particular pump protocol or pump operational parameters. For example, one access level might give a user a right to edit, create, and download pump protocols and/or pump application programs. One access level might permit a user the right to edit, create, and download only specified pump parameters, such as the patient specific pump parameters described in conjunction with FIGS. 5-6. One access level might permit a user the right to only edit or download pump parameters. One access level might permit a user the right to only view and download pump parameters. Different embodiments can include the ability to provide an access level for a user any combination of rights to create, edit, view, and/or download pump application programs and/or pump operational parameters. An example of lock levels are disclosed in U.S. Pat. No. 6,475,180, issued on Nov. 5, 2002 and entitled Drug Pump Systems and Methods, the entire disclosure of which is hereby incorporated by reference.

Once the user is logged in and the library is optionally loaded, the user selectively executes three different modules, a library module 708, a therapy module 710, and a protocol module 712.

The library module 708 assigns a label that identifies an entity and user attributes for the selected entity. Entity attributes can be properties specific to the library, such as a name of a doctor, a name of a healthcare regimen, or a location of the medical infusion pump or pump network, for example the hospital or department at which the pump is located. User attributes define the users allowed to access and modify pump parameters for protocols associated with a particular library by using the medical infusion pump, and can also define users allowed to modify pump protocols using user software, as described below. The library module 708 contains a library definition module 714 and a user rights module 716, which are configured to perform these tasks, respectively.

The therapy module 710 adds and modifies therapies, qualifiers associated with the therapies, and drugs. The therapy module includes a therapy definition module 718, a qualifier definition module 720, and a drug definition module 722. The therapy definition module 718 controls addition and editing of therapies, which are the methods of patient treatment for diseases or generalized rehabilitation as previously described. The qualifier module 720 defines qualifiers and associates the qualifiers with one or more therapies. The drug definition module 722 defines one or more drugs that can be used in the medical infusion pump.

The protocol module 712 adds, edits, and defines protocols by associating therapies, qualifiers, and drugs with pump parameters to form libraries of pump protocols for a medical infusion pump. The protocol module 712 allows a user to select a therapy defined in the therapy definition module 718. The protocol module further allows the user to associate a qualifier defined in the qualifier definition module 720 with the selected therapy. For example, one or both of "adults" and "children 5-10 years" qualifiers can be associated with an epidural therapy. The protocol module 712 also associates one or more drugs with each therapy and qualifier combination, indicating that use of the drug is appropriate for that therapy and qualifier. The protocol module 712 guides the user in defining a protocol by assigning default pump parameters to be associated with the selected therapy, qualifier, and drug.

The protocol module 712 allows a user to associate more than one qualifier to each therapy, and also allows a user to associate more than one drug to each therapy and qualifier combination. For example, a protocol used in an epidural therapy for an adult can include a higher basal delivery rate parameter than a protocol used with a child for the same therapy. Likewise, usage of one drug can require a higher or lower dosage than another drug for the same therapy and qualifier because of concentration, reaction, or other factors.

Operational flow proceeds from the modules 708, 710, 712 to an optional export library module 724. The export library module 724 saves the defined or edited pump application programs and parameters in a file or other data structure that can be loaded by the administrative software 700 at another time or location, or can be loaded by user software such as described below in FIGS. 26-41. If the export library module 724 does not execute, the library remains within the normally connected database 504 of FIG. 5, but is not extracted into a file for portability to a pump not connected to the network or to another medical infusion pump network. One or more libraries can be exported into a single library file.

Operation of the software 700 terminates at an end module 726. The end module 726 corresponds to termination of the administrative software 700 by clicking on a close window button on the computer or by some other mechanism for terminating execution of software.

In one embodiment of the administrative software 700, a user of the software 700 defines each protocol included in a library. In defining each protocol, the user assigns the index to the protocol, such as the therapy, qualifier, and drug defined in the modules 708, 710, 712 above. In a second possible embodiment, the administrative software includes a number of default settings or pump parameter modifications used when specific therapies, qualifiers, or drugs are selected. The user selects a therapy, qualifier, and drug to associate with a pump protocol. The administrative software 700 can include instructions dictating that selection of one or more of the therapies, qualifiers, and drugs sets or modifies one or more of the patient specific pump parameters or non-patient specific pump parameters. In one example of this second embodiment, a user setting a drug having a maximum safe consumption rate will trigger the administrative software 700 to preset an acceptable range of programmable delivery rates and a default delivery rate in the protocol, as well as alarms or other non-patient specific pump parameters. In another possible example of this second embodiment, a user setting a qualifier indicating a low age, such as "Children 5-10 years old", will set or adjust the protocol to result in a low delivery rate and demand dose being incorporated into the protocol, and will set one or more parameters related to alarms for use in a medical infusion pump.

Figure 8:
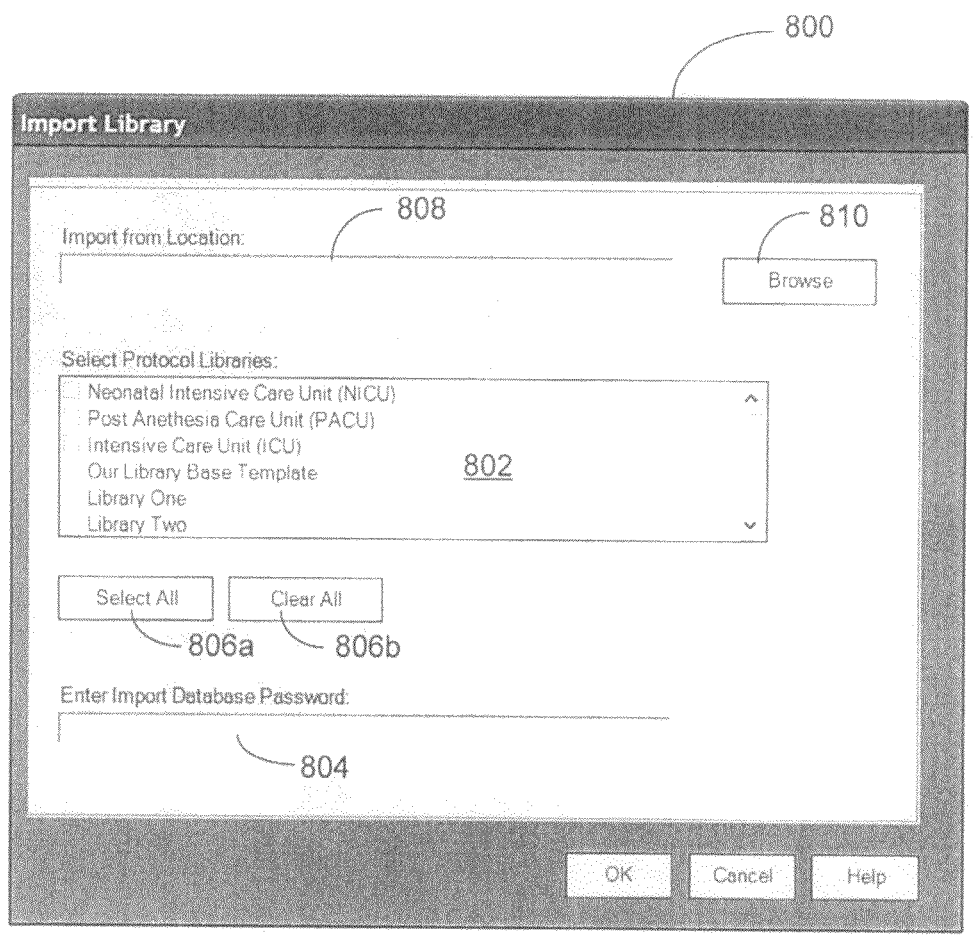
FIG. 8 is one example of a computer user interface library import screen in accordance with the present disclosure.

Referring now to FIG. 8, a library import screen 800 is shown. The library import screen corresponds to the load library module 704, and is optionally used to load a library file containing one or more libraries of pump programs in the administrative software 700 of FIG. 7, above. The library import screen 800 includes a file selection field 802 and a password field 804. The term field as used herein can include the window, or screen, generally, and can also include menus, selectable lists, or buttons within the window.

The file selection field 802 displays one or more library files that are available to be selected. The file selection field 802 allows a user to select one or more of the protocol library files, in conjunction with selection control buttons 806a, 806b. The password field 804 controls access to the selected library file by requiring a user to input a correct password associated with the selected file, or library within the file.

A location field 808 presents the directory path of the selected library file and a browse button 810 provides browsing capabilities to allow a user to find a library file other than those displayed in the library selection field 802.

In use, the library import screen 800 initially presents a listing of library files in the file selection field 802 available to the administrative software. The user selects one of the displayed library files, or presses the browse button 810 to search for additional library files. The user selects a library file by clicking on the displayed library file, or by other selection method. The directory path of the selected library file appears in the location field 808, and the user then enters a password in the password field 804 corresponding to the selected library file. The user confirms the choice using the selection control buttons 806a, 806b. The administrative software confirms that the user-entered password is correct, and accesses the library file.

Figure 9:
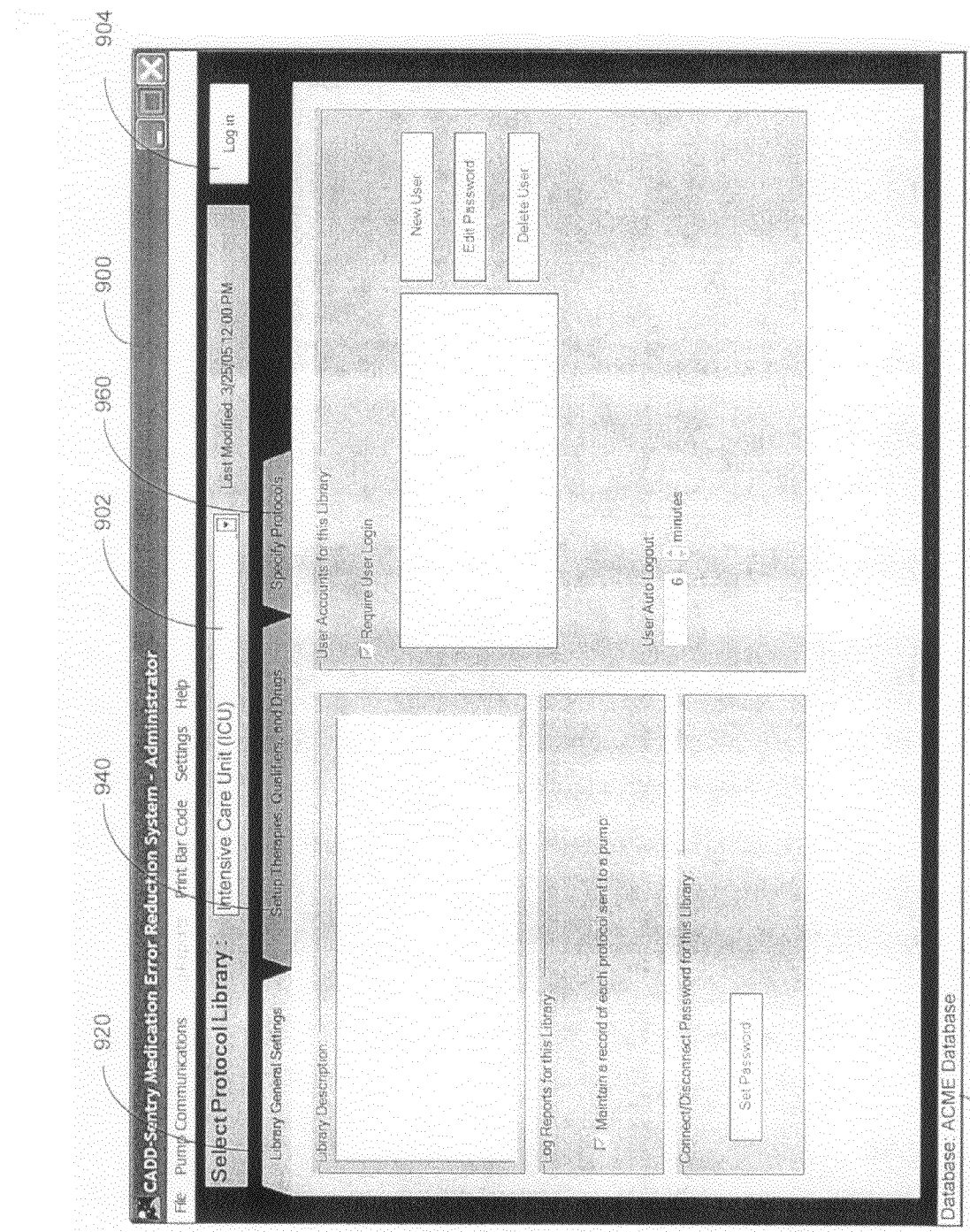
FIG. 9 is one example of a computer user interface for administrative software in accordance with the present disclosure.

Referring now to FIG. 9, a user interface 900 for the administrative software 700 of FIG. 7 is shown. The user interface 900 includes features associated with the modules incorporated in the administrative software 700, and corresponds to the screen displayed following the start operation 702 of FIG. 7. The user interface 900 includes a number of features providing global control and status information to a user.

Global control features included in the user interface 900 relate to library and pump access settings. A library field 902 provides a listing of libraries currently loaded by the software. The library field 902 contains the libraries which have been loaded using the load library module 704 of FIG. 7. A login button 904 generates a login screen that checks whether a user has the right to modify pump parameters and protocols.

The user interface 900 can display information related to the status of the network of medical infusion pumps. A database identification field 906 identifies the database 504 currently connected to the administrator computer 502, as shown in FIG. 5. In additional exemplary embodiments, additional information can be displayed, such as the location of the server and/or medical infusion pumps connected to the infusion pump network or a serial number or other identification number of the pumps or libraries.

The user interface 900 also includes a location tab 920, a therapy tab 940, and a protocol tab 960. Referring back to FIG. 5, the location tab 920 corresponds to the location module 708, the therapy tab 940 corresponds to the therapy module 710, and the protocol tab 960 corresponds to the protocol module 712. By clicking on or otherwise selecting a tab, a user transfers operation to the module corresponding to that tab.

Figure 10:
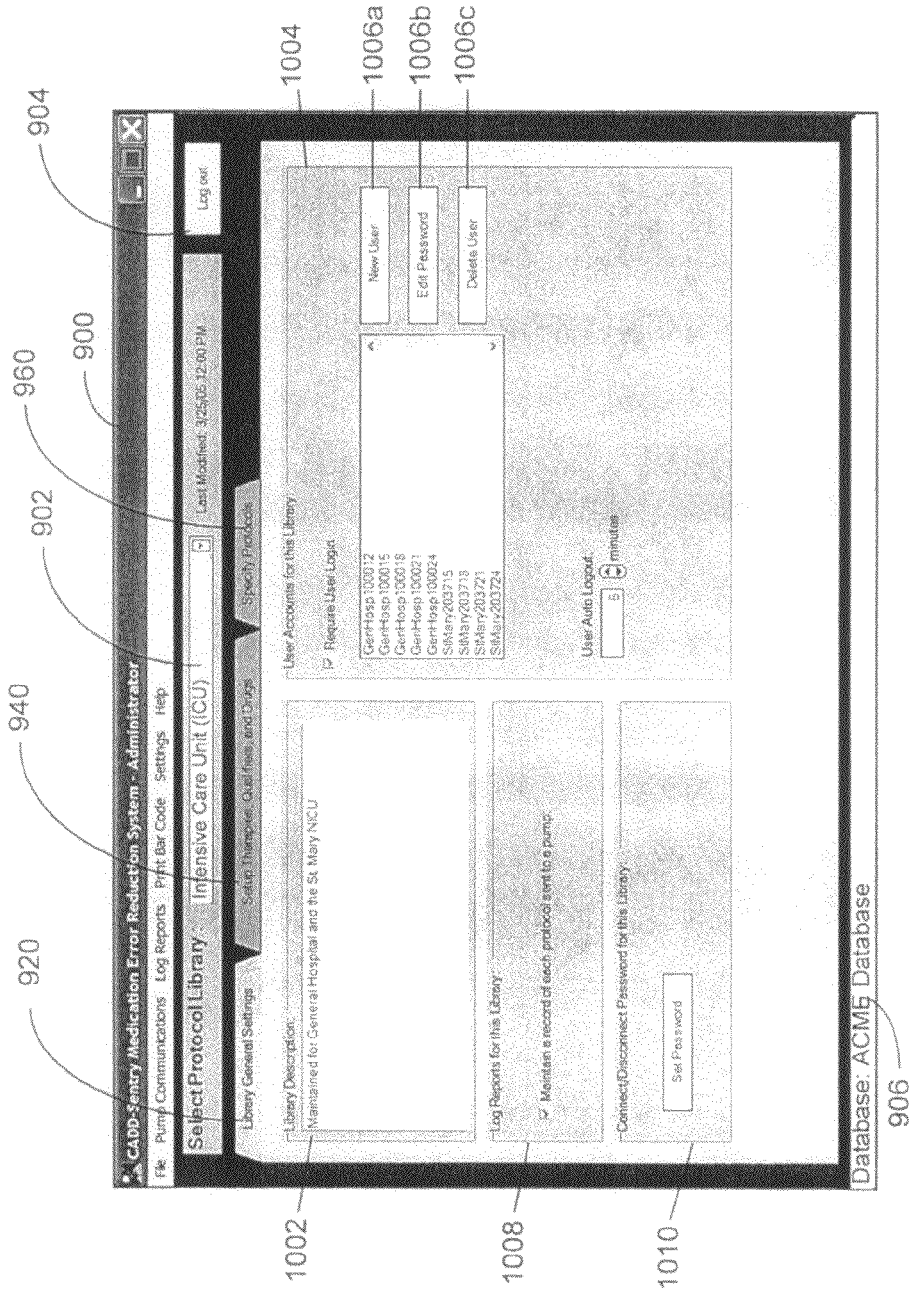
FIG. 10 is one example of a computer user interface location tab in accordance with the present disclosure.
Figure 11:
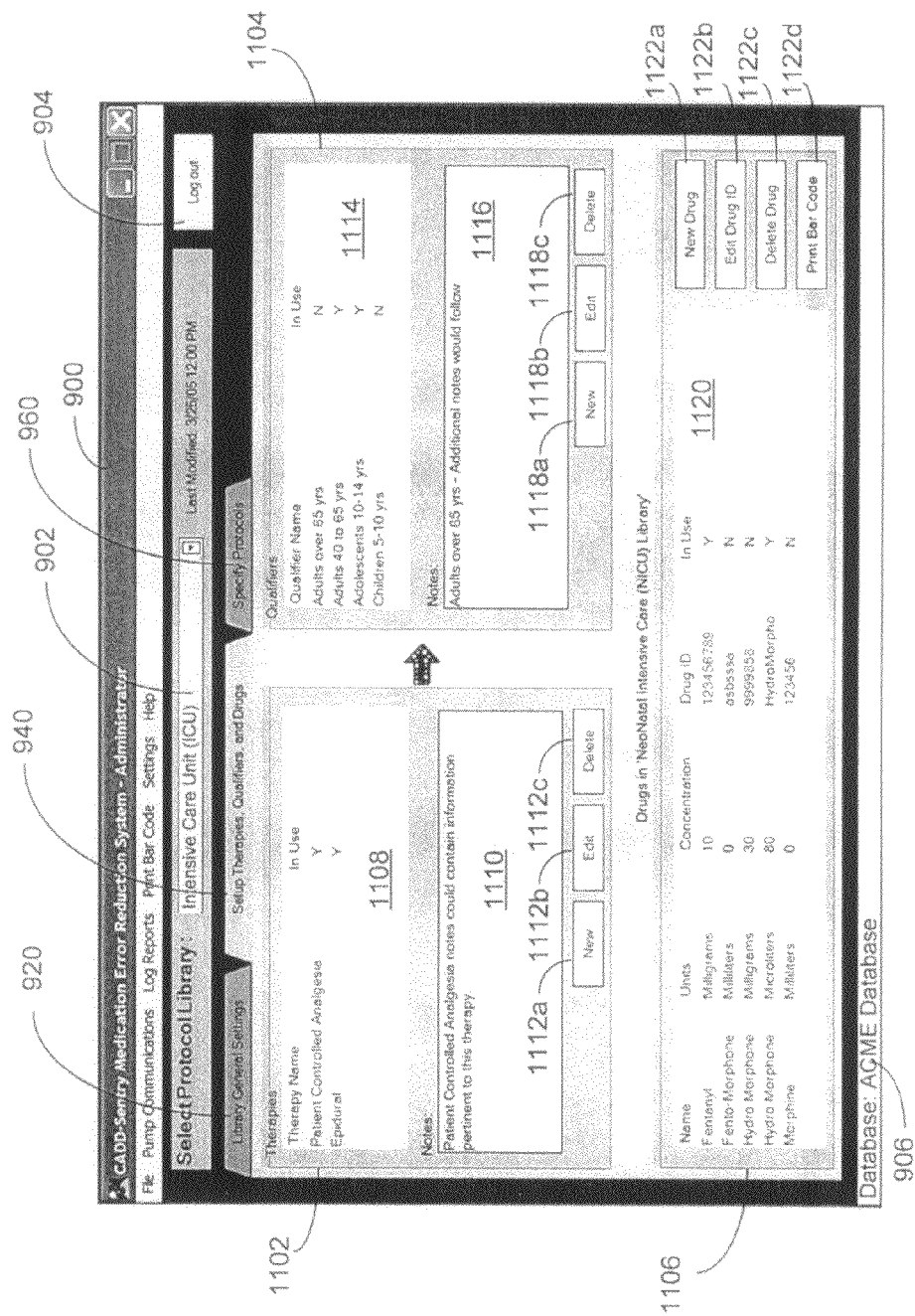
FIG. 11 is one example of a computer user interface therapy tab in accordance with the present disclosure.
Figure 12:
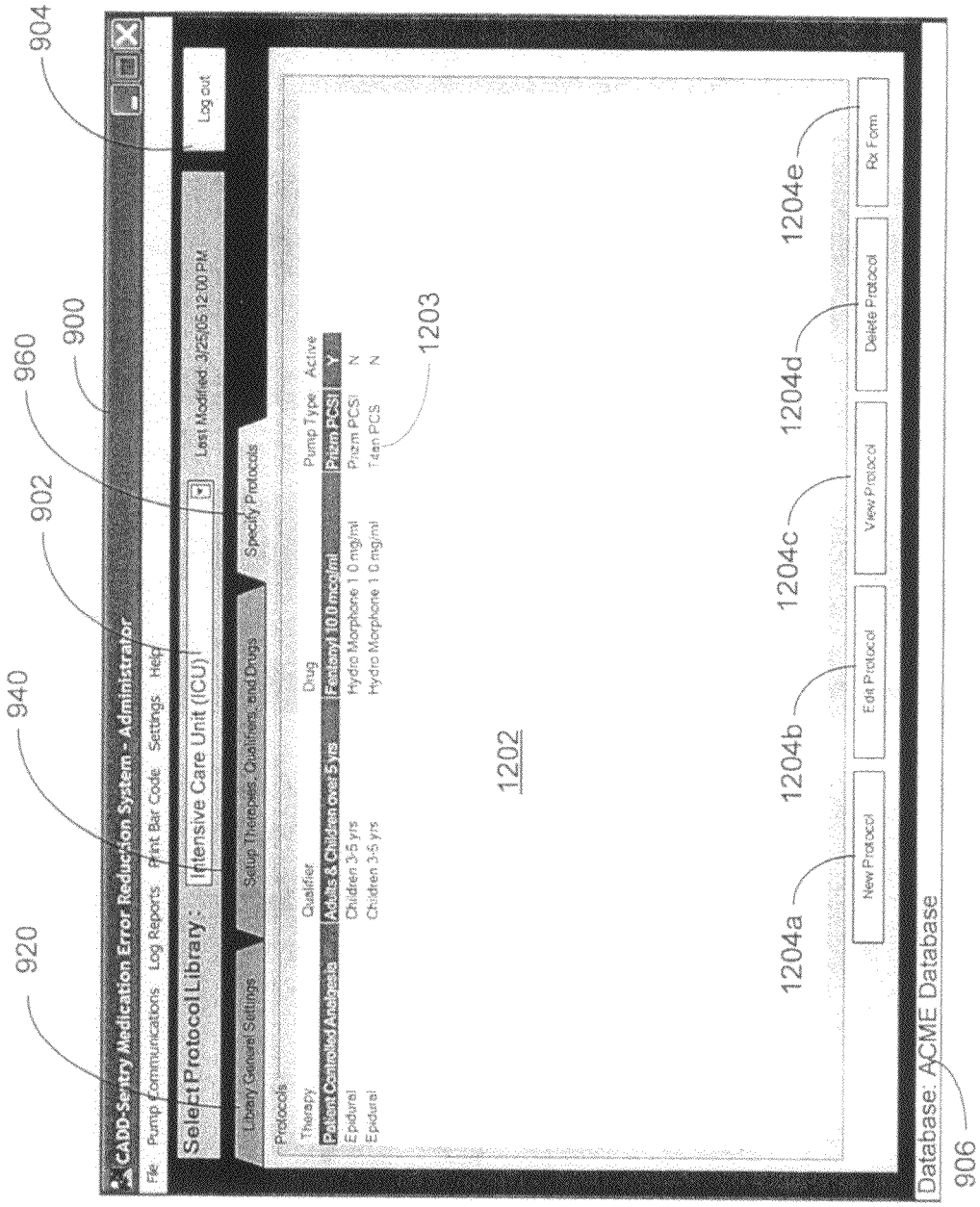
FIG. 12 is one example of a computer user interface protocol tab in accordance with the present disclosure.

Referring now to FIGS. 10-12, the user interface 900 is shown, and location tab 920, therapy tab 940, and protocol tab 960 are described in greater detail. FIG. 10 shows the user interface 900 after selection of the location tab 920, or after initial execution of the login module 706 and optional load library module 704.

A region of the location tab 920 supersedes the therapy tab 940 and protocol tab 960. Within the region exposed by the location tab 920, a library selected in the library field 902 populates a library description field 1002 and a user accounts field 1004. The library description field 1002 describes the library that is currently loaded, and includes attributes of the location in which the library is used, or other information about the library. The location attributes can include the name of the hospital or the department in the hospital associated with the library. The additional information can include information related to the users of the library, the contents of the library, or other information. The library description field 1002 corresponds to the location attributes module 714 of FIG. 7. The user accounts field 1004 displays a listing of user accounts associated with the library. Each of the user accounts generally correspond to a user, but can also correspond to a location of a computing system 104 or medical infusion pump 102. The user accounts define the persons allowed to access and modify pump protocols, and/or parameters associated with the library at the point of care, such as a medical infusion pump 102 or computing system 104 executing user software. The user accounts field 1004 enables a user to add, edit, or delete users from the listing using the buttons 1006a-1006c provided. The user accounts field corresponds to the user rights module 716 of FIG. 7.

In a possible embodiment, a log report field 1008 can optionally direct the server 206 to generate a record for various events occurring in the database 504. For example, a log report can be created each time a protocol is sent to a medical infusion pump 102. Alternately, a log report is created each time a library is sent to a medical infusion pump 102. In further embodiments, a log report is created each time a library is edited or accessed. In still further embodiments, globally unique identifiers are entered into the log report related to instances where computing systems 104 and/or infusion pumps 102 access a library in the database 504. In the embodiment shown, the log report field 1008 is a selectable check box, but can be implemented as any other type of selectable field.

A password field 1010 sets a password for the currently selected library file. The password protects access to the library from the perspective of user software residing on either a computing system 104 or an infusion pump 102 such that only users with knowledge of the password associated with the library file can load the library using the load library module 704 of FIG. 7 and user interface 800.

Referring now to FIG. 11, the user interface 900 is shown with the therapy tab 940 selected. A region of the therapy tab 940 supersedes the location tab 920 and the protocol tab 960. The therapy tab 940 corresponds to the therapies module 710, which defines therapies, qualifiers, and drugs used by medical infusion pumps associated with the administrative software 700 of FIG. 7. The therapy tab 940 includes a therapy definition field 1102, a qualifier definition field 1104, and a drug definition field 1106.

The therapy definition field 1102 corresponds to the therapy definition module 718 of FIG. 7, and includes a therapy listing 1108, a therapy notes field 1110, and control buttons 1112a-1112c. The therapy listing 1108 displays the therapies currently defined in the library displayed in the library listing 802. Two example therapies, "Patient Controlled Analgesia" and "Epidural", are shown in the therapy listing 1108, and are associated with a library named "Neo-Natal Intensive Care Unit". The therapy notes field 1110 contains administrative user-defined notes related to the therapy selected in the therapy listing 1108. The notes relate to a therapy, and include information related to administration of the therapy, such as messages related to dosage, bolus amount, or administration. The therapy notes field 1110 presents administrative user-created notes to convey therapy-specific information to caregivers using or programming the pump. Control buttons 1112a-1112c allow a user to add, edit, and delete therapies from the therapy listing 1108 and therapy notes field 1110.

The qualifier definition field 1104 corresponds to the qualifier definition module 720 of FIG. 7, and includes a qualifier listing 1114, a qualifier notes field 1116, and control buttons 1118a-1118c. The qualifier definition field 1104 lists the qualifiers associated with the therapy selected from the list shown in the therapy listing 1108. For example, an administrative user might add a "Children 5-10 yrs" entry to the qualifier listing 1114. Each therapy relates to one or more qualifiers, such as a general qualifier, a weight based qualifier, or an age based qualifier. The qualifier notes field 1116 contains notes describing the difference in application of the therapy based on the qualifier selected. In the case of the "Children 5-10 years" qualifier, the qualifier notes field 1116 can indicate a lower than normal dosage to be administered. Notes associated with the qualifier display in the qualifier notes field 1116 only when the qualifier is selected.

The drug definition field 1106 corresponds to the drug definition module 722 of FIG. 7, and includes a drug listing 1120 and control buttons 1122a-1122d. The drug listing 1120 includes information related to the therapeutic fluid used in the medical infusion pump. This information can include the drug name, identification code, units, concentration, and usage. The control buttons 1122a-1122c allow a user to add, edit, or delete drugs in the drug listing 1120. A bar code control button 1122d generates a bar code screen including information related to a drug.

Referring now to FIG. 12, the user interface 900 is shown with protocol tab 960 selected. The protocol tab 960 supersedes the location tab 920 and the therapy tab 940. The protocol tab 960 corresponds to the protocol module 712 of FIG. 7, and associates therapies, qualifiers, and drugs to allow a user to define protocols by setting pump parameters for inclusion within pump programs. The protocol tab 960 includes a protocol field 1202 and control buttons 1204a-1204e. The protocol field 1202 lists the combinations of therapies, qualifiers, and drugs for which a protocol is defined. The protocol field 1202 also lists a pump type 1203 for which each protocol is defined. By specifying a pump type for which each protocol is defined, it is possible to enable pump-specific protocol programming, while still using the administrative software 700 and user software, described below, for all pump types configurable using the protocol-based programming scheme described herein.

The control buttons 1204a-1204e operate to add, edit, view, and/or delete the protocol for the combinations of therapies, qualifiers, and drugs. The control buttons 1204a-1204d allow a user to set pump parameters so as to define the protocol. Control button 1204e generates a prescription form screen representing the protocol for the selected therapy, qualifier, and drug.

Figure 13:
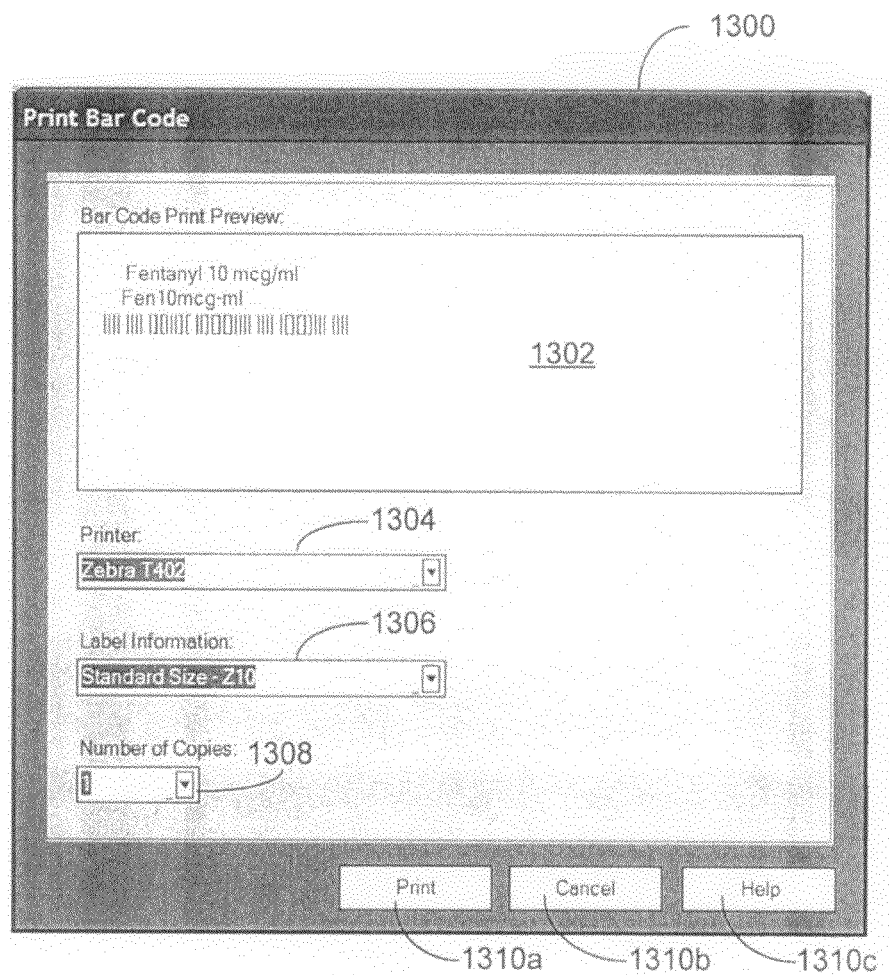
FIG. 13 is one example of a computer user interface drug bar code display screen in accordance with the present disclosure.

FIG. 13 shows a bar code screen 1300 displaying a bar code for a drug defined in the administrative software 700 of FIG. 7. A drug identification code is associated with each drug in the drug listing 1120 of FIG. 11. A drug is selected from among those in the drug listing 1120 of FIG. 11, and the bar code screen 1300 displays upon clicking on the control button 1122d.

The bar code screen 1300 includes a print preview field 1302, a printer drop down menu 1304, a label information menu 1306, a copies drop down menu 1308, and control buttons 1310a-1310c. The print preview field 1302 displays a bar code associated with the selected drug. The printer drop down menu 1304 lists available printers configured to print the bar code. The label information drop down menu 1306 defines the label configuration to which the bar code is directed. The label configuration includes, for example, the size and layout of the label paper. The copies drop down menu 1308 dictates the number of copies of the bar code that are printed. Control buttons 1310a-1310c provide printing, cancellation, and help procedures to a user.

In use, the bar code corresponds to a drug identification code associated with the drug. In a possible embodiment, a pharmacist can print the barcode associated with the drug using the administrative software 700 via the bar code screen 1300 and affix the printed bar code label to the drug container. The labels indicate the drug and dosage being delivered by the pump. This provides an easily accessible and visually prominent indication of the drug being delivered by a medical infusion pump.

A caregiver connecting a drug to a medical infusion pump 102 will scan the bar code on the drug container, which will correspond to the drug identification code associated with the drug in the administrative software 700. This ensures that the caregiver affixes the drug to the pump which corresponds to the protocol selected using administrative software 700.

Figure 14:
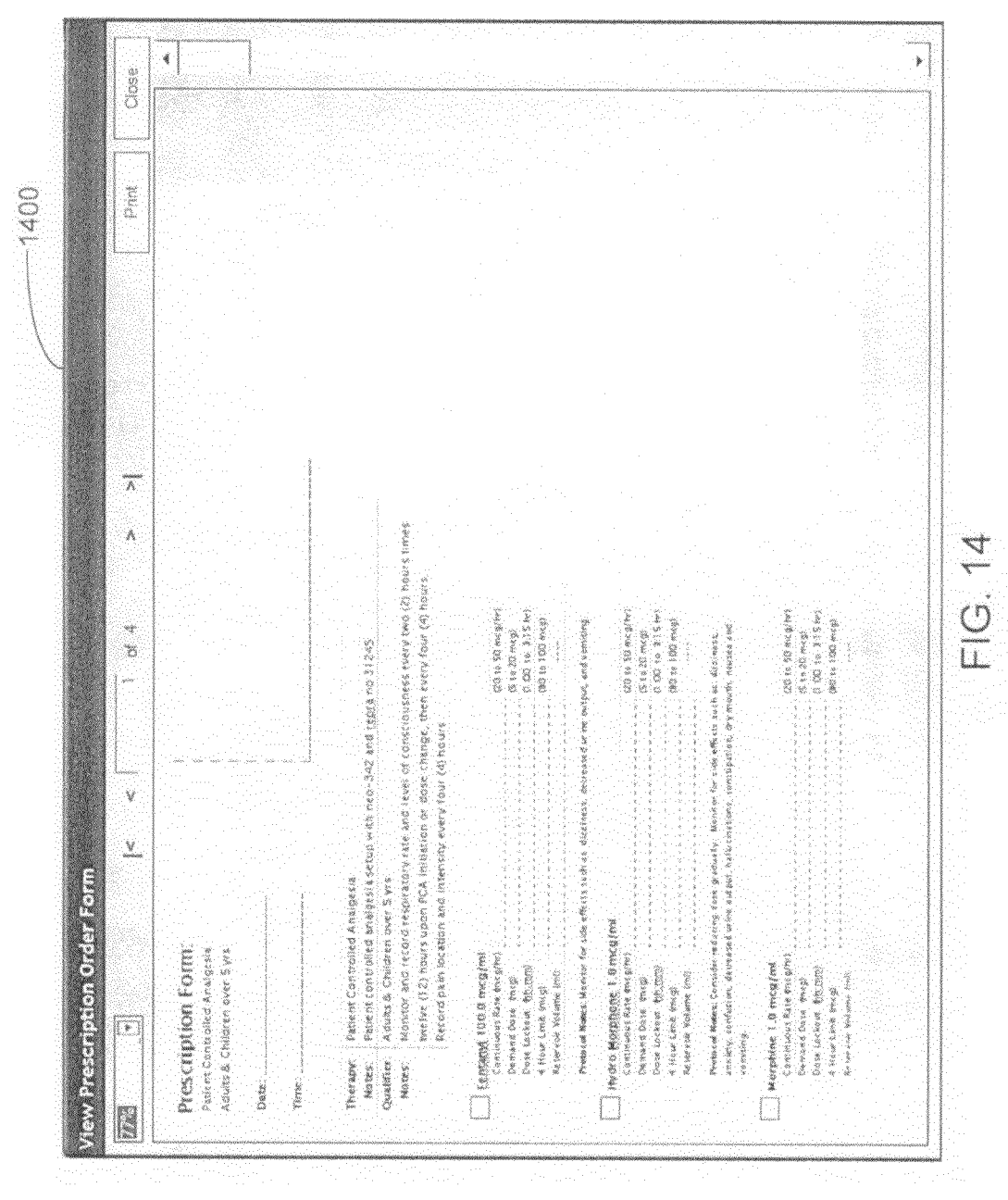

FIG. 14 shows a prescription form screen 1400 displaying prescription information related to a specific therapy, qualifier, and drug. The prescription form screen displays upon selection of control button 1204e on protocol tab 960. The prescription form screen 1400 corresponds to the currently selected protocol, and therefore incorporates information specific to the selected protocol. Prescription information includes, for example, directions for application of the drug according to the defined protocol, and parameters such as drug delivery rates or bolus amounts. The prescription form also includes usage notes describing operation or application of the selected therapy, qualifier, and drug.

A doctor using the prescription form dictates the protocol used in the pump by using a prescription form analogous to the prescription form screen. The prescription form 1400 generated by the administrative software will correspond to the prescription form completed by the doctor. In the embodiment shown, the prescription form screen 1400 that is generated includes information specific to the drug and therapy administered, which may be notes related to administration of the drug and therapy as dictated by the doctor. For example, the prescription form will include drug information, such as the name, type, concentration, and notes regarding the drug, and will also include information related to patient specific pump parameters associated with a selected therapy, qualifier, and drug selected from a library.

Figure 15:
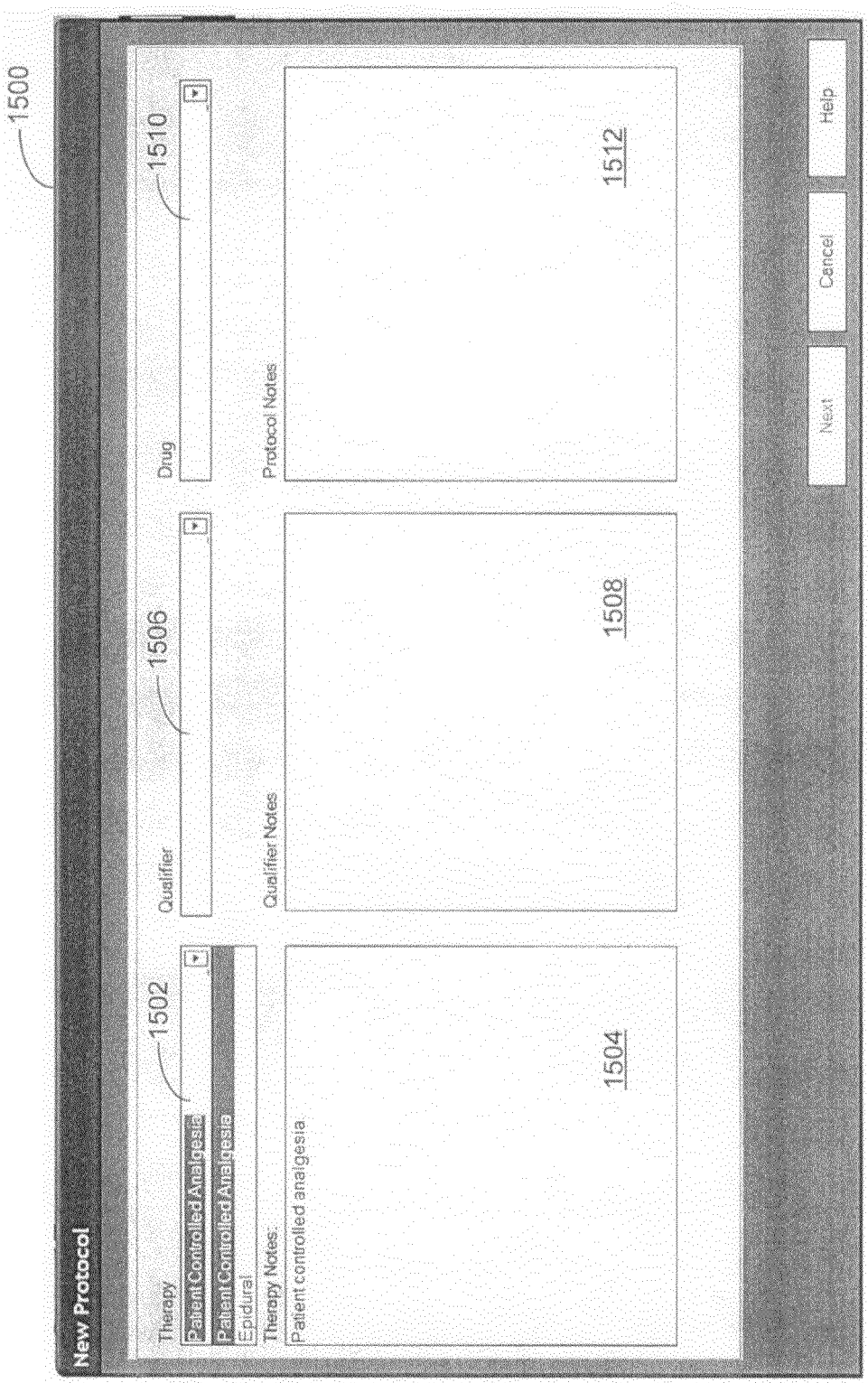
FIG. 15 is one example of a computer user interface therapy selection screen in accordance with the present disclosure.
Figure 16:
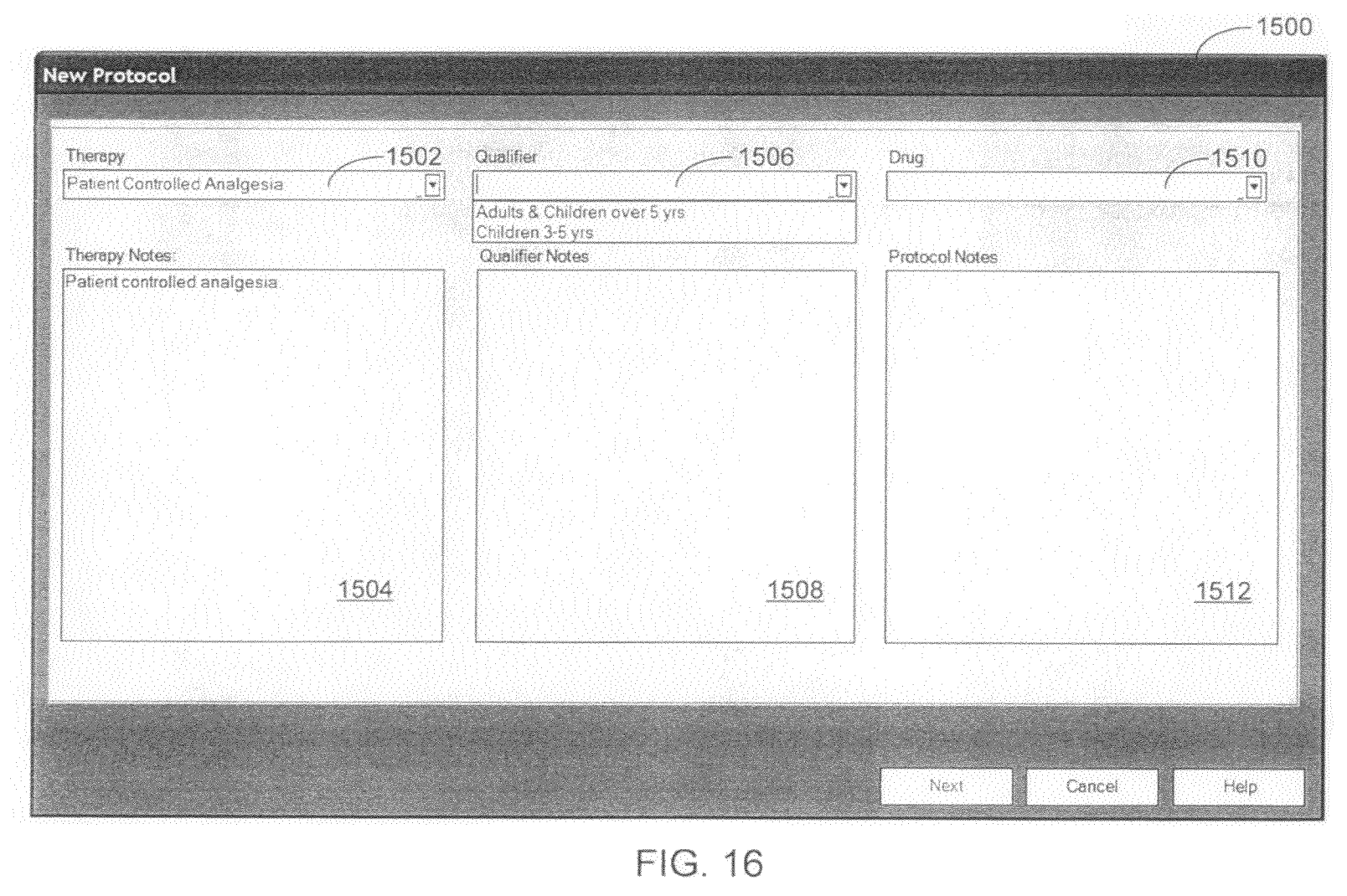
Figure 17:
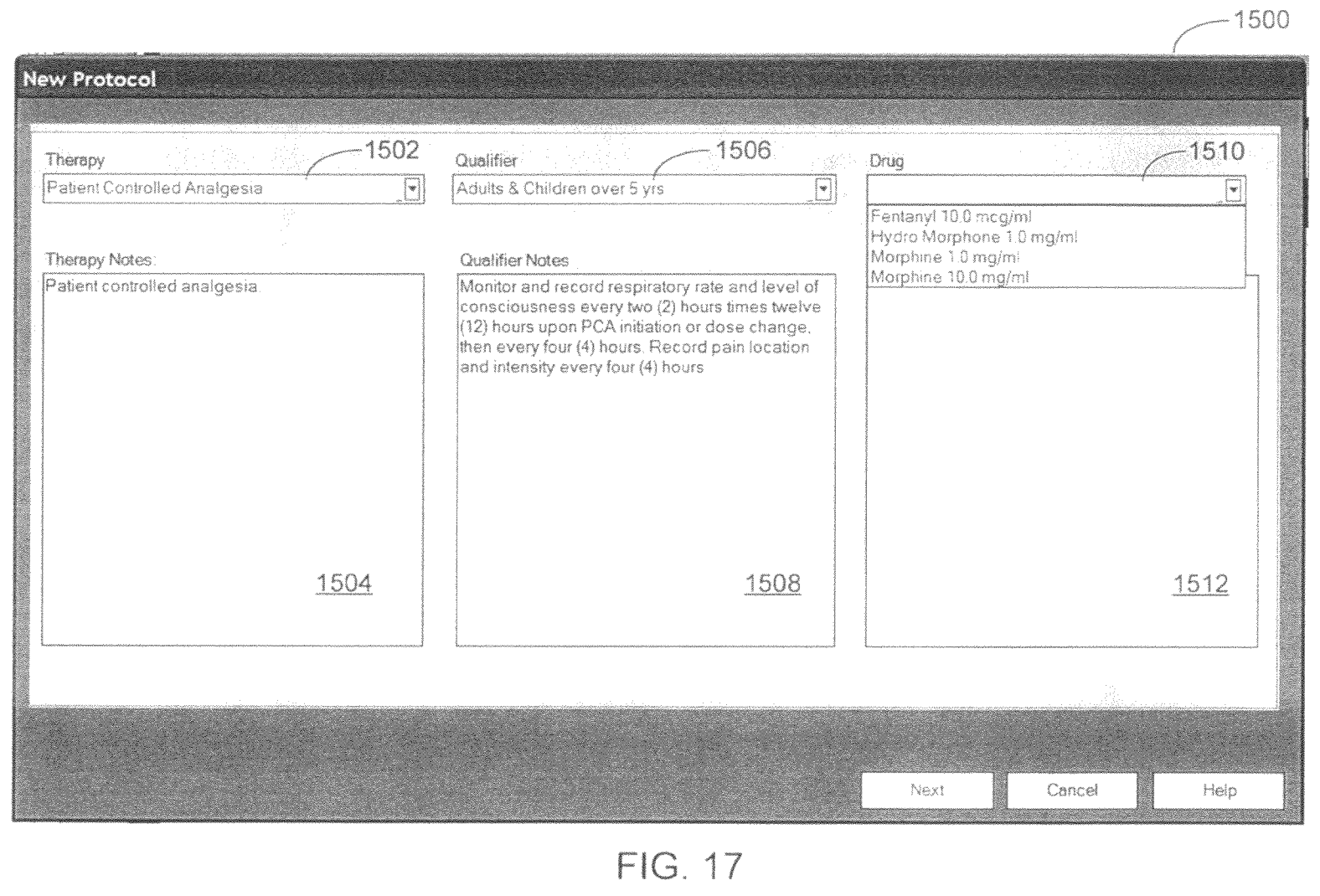

Referring now to FIG. 15-17, a protocol definition user interface 1500 defines the relationships between the therapies, qualifiers, and drugs added to the library by the therapy module 710 and using the therapy tab 960. A user defines a protocol by setting an index by sequentially selecting a therapy, a qualifier, and a drug, and then by associating pump parameters with that index. In setting the index using the user interface 1500, a therapy drop down menu 1502 connects to a therapy notes field 1504, a qualifier drop down menu 1506 connects to a qualifier notes field 1508, and a drug drop down menu 1510 connects to a drug notes field 1512.

FIG. 15 shows the initial state of the protocol definition user interface 1500. A list of therapies appears in the therapy drop down menu 1502, while the remaining menus 1506, 1510 and fields 1504, 1508, 1512 remain blank.

FIG. 16 shows the state of the protocol definition user interface 1500 after a therapy is selected in the therapy drop down menu 1502. Notes related to the selected therapy appear in the therapy notes field 1504, and a list of qualifiers associated with the selected therapy appears in the qualifier drop down menu 1506. The notes correspond to the therapy notes entered in the therapy notes field 1110. The list of qualifiers corresponds to the qualifiers associated to the therapy by listing in the qualifier listing 1114. For example, two qualifiers, "Adults & Children over 5 yrs" and "Children 3-5 yrs" can be associated with the "Patient Controlled Analgesia" therapy. When that therapy is selected in the therapy drop down menu 1502, the two associated qualifiers populate the qualifier drop down menu 1506.

FIG. 17 shows the state of the protocol definition interface 1500 after a qualifier is selected in the qualifier drop down menu 1506. Notes related to the qualifier appear in the qualifier notes field 1508, and a list of drugs available within the library or database appears in the drug drop down menu 1510. The notes correspond to changes in the therapy due to the qualifier selected. Continuing the example from FIG. 14, the "Adults & Children over 5 yrs" qualifier is selected. Notes related to customization of the "Patient Controlled Analgesia" therapy based on the selected qualifier are displayed in the qualifier notes field 1508. Furthermore, a list of four drugs/drug concentrations appear in the drug drop down menu 1510, which are the drugs defined and available within the library or database.

Analogously, upon selection of a drug from the drug drop down menu 1510, drug notes (not shown) appear in the drug notes field 1512.

Referring now to FIGS. 18-24, a parameter user interface 1800 provides additional tabbed screens allowing a user to define pump parameters. The pump parameters complete the protocol definition associated with the therapy, qualifier, and drug combination selected in FIGS. 15-17. As described in conjunction with FIG. 7, selection of the index defined by a therapy, qualifier, and drug using the protocol definition interface 1500 may trigger the administrative software 700 to set or modify one or more of the pump parameters. Alternately, none of the pump parameters are set during the definition and selection of the index formed by the therapy, qualifier, and drug using the protocol definition interface 1500. In such an embodiment, the parameter user interface 1800 is used to define the pump parameters that are programmable into a medical infusion pump.

The parameter user interface 1800 includes a status region 1802, a protocol activation field 1804, and control buttons 1806a-1806c. The status region 1802 displays the therapy, qualifier, and drug associated with the assignable pump parameters. The protocol activation field 1804 publishes the protocol within the library such that the protocol is visible to user software accessing the library when it resides within the database 504 of FIG. 5. The protocol activation field 1804 allows a user of the administrative software 700 to control when protocols become available for use by user software. In some circumstances, it can be advantageous to prevent user software from accessing data, particularly while that data is being edited in the administrative software 700. One example of user software used to access pump protocols is illustrated below in conjunction with FIGS. 26-41. The control buttons 1806a-1806c provide save, cancel, and help options to a user of the administrative software.

The parameter user interface 1800 further includes a number of tabs, including a drug delivery tab 1810, a secondary drug delivery tab 1820, an alarm tab 1830, a security tab 1840, a display/sound tab 1850, and a report tab 1860. Parameters set within each of the tabs are discussed in FIGS. 18-24.

Figure 18:
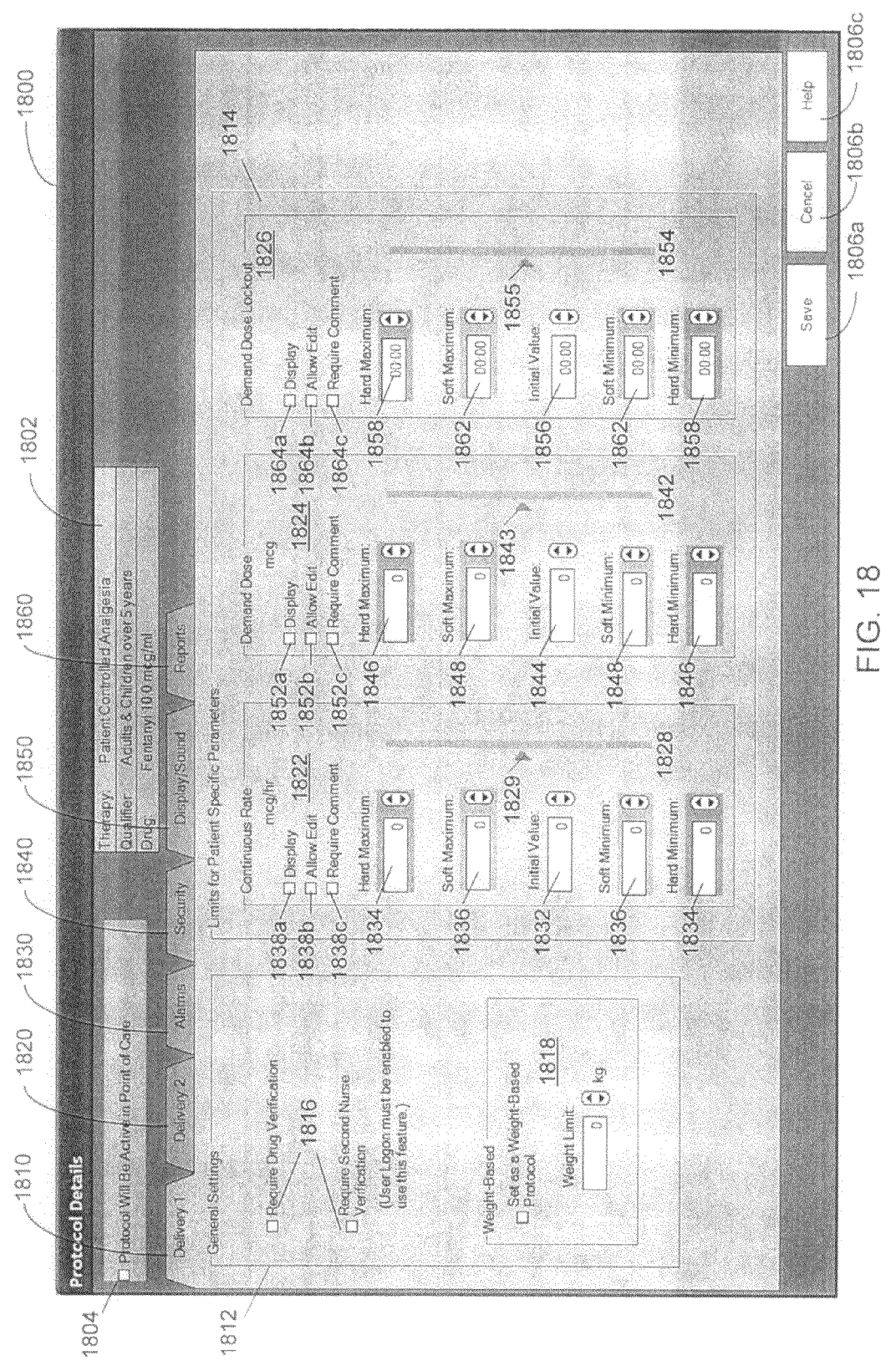

FIG. 18 shows the parameter user interface 1800 with the drug delivery tab 1810 selected. The drug delivery tab 1810 allows a user to set drug delivery rate parameters, and includes a general settings region 1812 and a patient specific parameters region 1814.

The general settings region 1812 includes verification settings 1816 and weight based settings 1818. The verification settings 1816 includes drug verification and caregiver verification settings. Specifically, the verification settings require that a caregiver verifies that the correct drug is provided to the medical infusion pump. The verification settings also require a second caregiver to verify the settings of the medical infusion pump. The weight based settings 1818 set a weight based protocol at a programmable, variable weight limit. By weight based protocol, it is intended that dosage delivery rates, boluses, thresholds, and other delivery parameters change from a "dosage per hour" basis to a "dosage per weight factor" rate, where the weight factor can be on a per unit measure weight basis for the user of the medical infusion pump 102 (i.e. "per kilogram" or other), or based on the user's body surface area, a weight based therapy, or other options.

The patient specific parameters region 1814 includes a continuous rate region 1822, a demand dose region 1824, and a demand dose lockout region 1826. Continuous rate refers to the constant drug delivery rate of the medical infusion pump, also referred to as the basal rate. Demand dose refers to an added drug delivery bolus amount delivered by the pump upon a demand by a patient. Demand dose lockout refers to the time interval after a demand dose is delivered, during which another demand dose will not be delivered by the pump.

The continuous rate region 1822 includes a meter, shown as a slider bar 1828 and an indicator 1829. The meter generally has two or more locations, each corresponding to a parameter value that can be programmed in the medical infusion pump. Generally, the positional relationship of the meter indicates the setting of the meter. In a possible embodiment of the slider bar 1828 shown, the indicator 1829 is movable relative to the slider bar 1828 to set a default value, or "initial value" continuous drug delivery rate parameter. In a second possible embodiment, the default value is set using an initial value gauge 1832.

The continuous rate region also includes hard limit gauges 1834, soft limit gauges 1836, and user interface options 1838a-1838c. The initial value gauge 1832, hard limit gauges 1834, and soft limit gauges 1836 include values, which may include numerical ranges. The hard limit gauges 1834 set a hard maximum and hard minimum which form an acceptable pump programming range. The range of acceptable pump activity represents the absolute maximum and minimum values programmable into the pump by user software, as described below. This configuration allows for control of the range of values visible to a user of the medical infusion pump or associated computing system.

The limits set by the soft limit gauges 1836 represent a manually exceedable threshold value. The soft limit can be overridden by a user of a medical infusion pump on a pump-by-pump basis. Pump activity outside the range defined by soft limits can trigger an alarm or otherwise alert a caregiver that a pump is functioning outside of the usual operational range of the pump. A variety of alarm levels or alerts can be set by the soft limit gauges 1836. For example, the alert can be a flag set in the software. The alert could additionally be an audible alarm, or a visual indicator displayed on at least a portion of the medical infusion pump. The visual indicator could be a flashing indicator or changed/changing color on the display of the medical infusion pump.

In a second possible embodiment, the hard limit gauges set a non-limiting range, and the user software described below can be programmed within its full operational range. In such an embodiment, pump activity outside the range set by the hard limit gauges 1834 can trigger an alarm or otherwise alert a caregiver that a pump is functioning outside of the usual operational range of the pump. In this embodiment, the soft limit gauges 1836 set a narrower range, operation outside of which can trigger a warning or second alarm indicating pump activity outside of an expected range of pump operation. This warning or second alarm indicates a pump condition less serious than the alarm triggered by the hard limits.

The user interface options 1838a-1838c enable the user software to display and edit the delivery rate, editing of the delivery rate, and requiring comments by users of a pump who wish to exceed the soft limits when setting the drug delivery rate. Selection of the display option 1838a publishes the pump parameter so that the value is visible to a user of the pump or computing system.

The demand dose region 1824 includes a slider bar 1842 and an indicator 1843. The slider bar and indicator operate in a similar manner to the slider bar 1828 and indicator 1829 in the continuous rate region 1822, but control demand dose settings. Likewise, the demand dose region 1824 includes an initial value gauge 1844, as well as hard limit gauges 1846 and soft limit gauges 1848 setting visible thresholds and triggering alarms as in the continuous rate region 1822. Demand dose options 1852a-1852c provide analogous display, editing, and comment options to the user interface options 1838a-1838c.

The demand dose lockout region 1826 includes a slider bar 1854 and an indicator 1855, and also includes an initial value gauge 1856, hard limit gauges 1858, and soft limit gauges 1862. Each of these features functions analogously to those discussed above in conjunction with the continuous rate region 1822. The demand dose lockout region also includes lockout options 1864a-1864c analogous to the user interface options 1838a-1838c.

Figure 19:
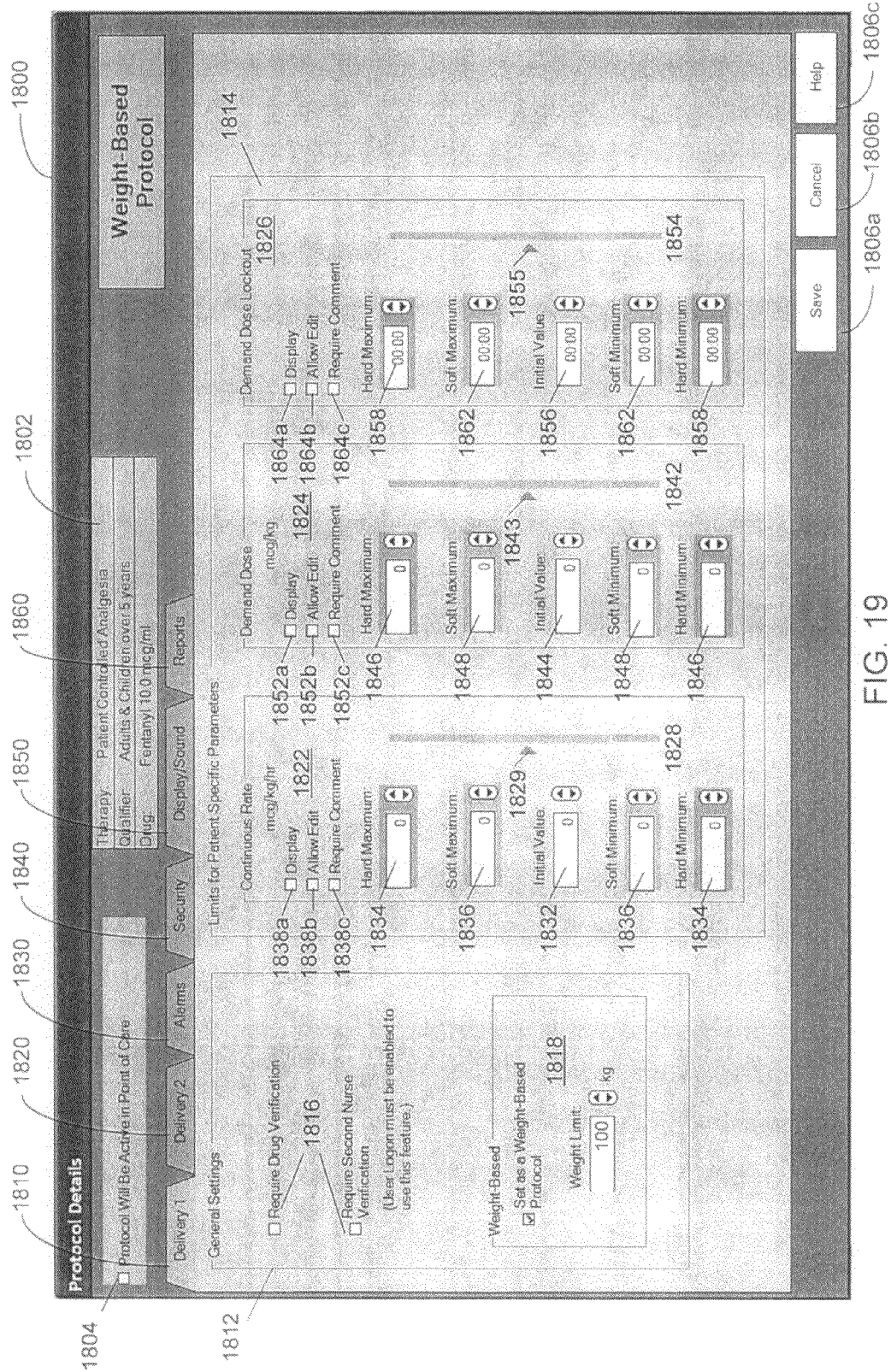
FIG. 19 is one example of a computer user interface weight-based drug delivery tab in accordance with the present disclosure.

FIG. 19 shows the parameter user interface 1800 with the drug delivery tab 1810 modified to provide a weight based drug delivery protocol. The modification of the user interface 1800 occurs in the drug delivery tab 1810 upon user selection of the weight based settings 1818 discussed in FIG. 18. The continuous rate region 1822 and demand dose region 1824 are modified to reflect dosage rates on a "per kilogram" or other weight measure basis.

Figure 20:
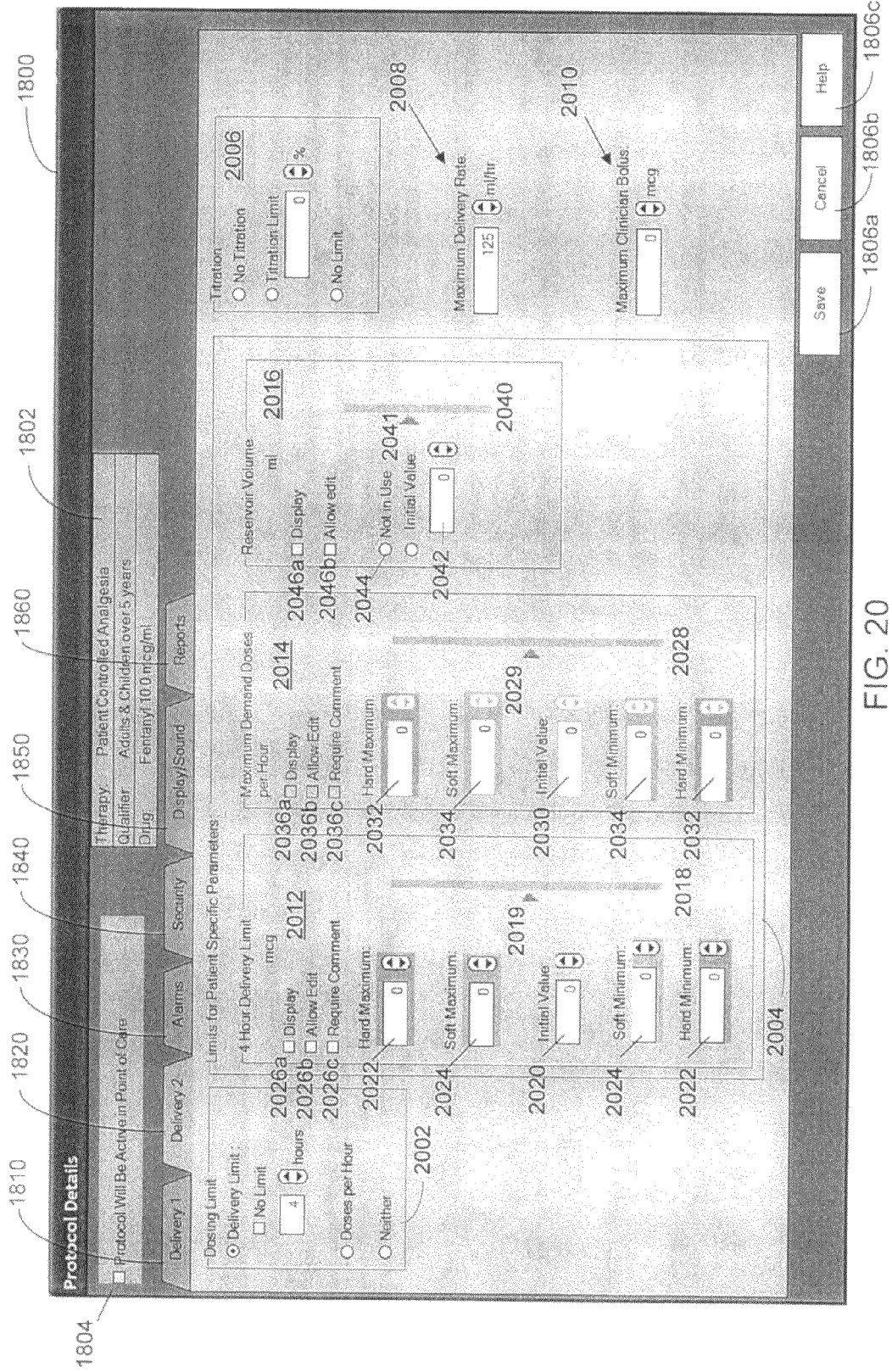
FIG. 20 is one example of a computer user interface secondary drug delivery tab in accordance with the present disclosure.

FIG. 20 shows the parameter user interface 1800 with the secondary drug delivery tab 1820 selected. The secondary drug delivery tab 1820 provides additional medical infusion pump programming options for assigning pump parameters in a specific protocol. The secondary drug delivery tab 1820 includes a dosing limit region 2002, a patient specific parameter region 2004, a titration region 2006, a maximum delivery rate gauge 2008, and a maximum clinician bolus gauge 2010.

The dosing limit region 2002 displays limits for total drug delivery within a specified amount of time. The dosing limit region 2002 includes options for setting a limit on doses per hour, a timed medication delivery limit, or other limits. A user selects one of the options for setting the dosage limit.

The patient specific parameter region 2004 sets parameters related to the dosage limits coordinated to the options in the dosing limit region 2002. The patient specific parameter region 1804 includes a timed delivery limit region 2012, an hourly demand doses region 2014, and a reservoir region 2016.

The timed delivery limit region 2012 sets the delivery limit on a per assigned time period when the option for setting a limit on doses per hour is selected in the dosing limit region 2002. The timed delivery limit region 2012 includes a meter, shown as a slider bar 2018 and indicator 2019. The timed delivery limit region 2012 also includes an initial value gauge 2020, hard limit gauges 2022, soft limit gauges 2024, and control options 2026a-2026c. Operation of the slider bar 2018, indicator 2019, gauges 2020-2024, and control options 2026a-2026c is analogous to operation of the slider bar features as discussed in conjunction with FIG. 18, above.

The hourly demand doses region 2014 sets the delivery limit on a per hour basis when the doses per hour limit is selected in the dosing limit region 2002. The maximum demand doses region 2014 includes a slider bar 2028, indicator 2029, gauges 2030-2034, and control options 2036a-2036c, operation of which is likewise analogous to operation of the slider bar features discussed in FIG. 18.

The timed delivery limit region 2012 and hourly demand doses region 2014 are operated in the alternative, in that only one of the two regions is active at one time. The region that is active depends upon the option selected in the dosing limit region 2002. Selection of a timed delivery limit in the dosing limit region 2002 activates the timed delivery limit region 2012 and deactivates the hourly demand doses region 2014. Selection of an hourly delivery limit activates the hourly demand doses region 2014 and deactivates the timed delivery limit region 2012.

The reservoir region 2016 sets the initial volume settings and display settings for tracking the volume of fluid in the reservoir attached to the medical infusion pump. The reservoir region 2016 includes a meter, shown as a slider bar 2040 and indicator 2041, operation of which is analogous to the slider bar and indicator discussed in conjunction with FIG. 18. The reservoir region further includes an initial value gauge 2042, a disable option 2044, and control options 2046a-2046b. The initial value gauge 2042 provides an alternate method for setting the initial value of the reservoir volume to the slider bar 2040 and indicator 2041. The disable option 2044 disables the reservoir volume monitor. The control options 2046a-2046b provide display and edit capabilities to a user of the pump.

The remaining regions, i.e. the titration region 2006, the maximum deliver rate gauge 2008, and the maximum clinician bolus gauge 2010, set pump specific settings related to drug delivery limits. The titration region 2006 enables or disables titration in the medical infusion pump, and sets an optional titration limit in the pump. The maximum delivery rate gauge 2008 sets a maximum delivery rate for the infusion pump. The maximum delivery rate is measured in milliliters per hour, and includes both the basal delivery rate and bolus delivery. The maximum clinician bolus gauge 2010 sets the maximum bolus which can be delivered by a caregiver. The maximum clinician bolus may be a larger bolus than the standard patient-controlled bolus, but must be administered under the supervision of a caregiver. Other regions can be included in the tab 1820 as well.

Figure 21:
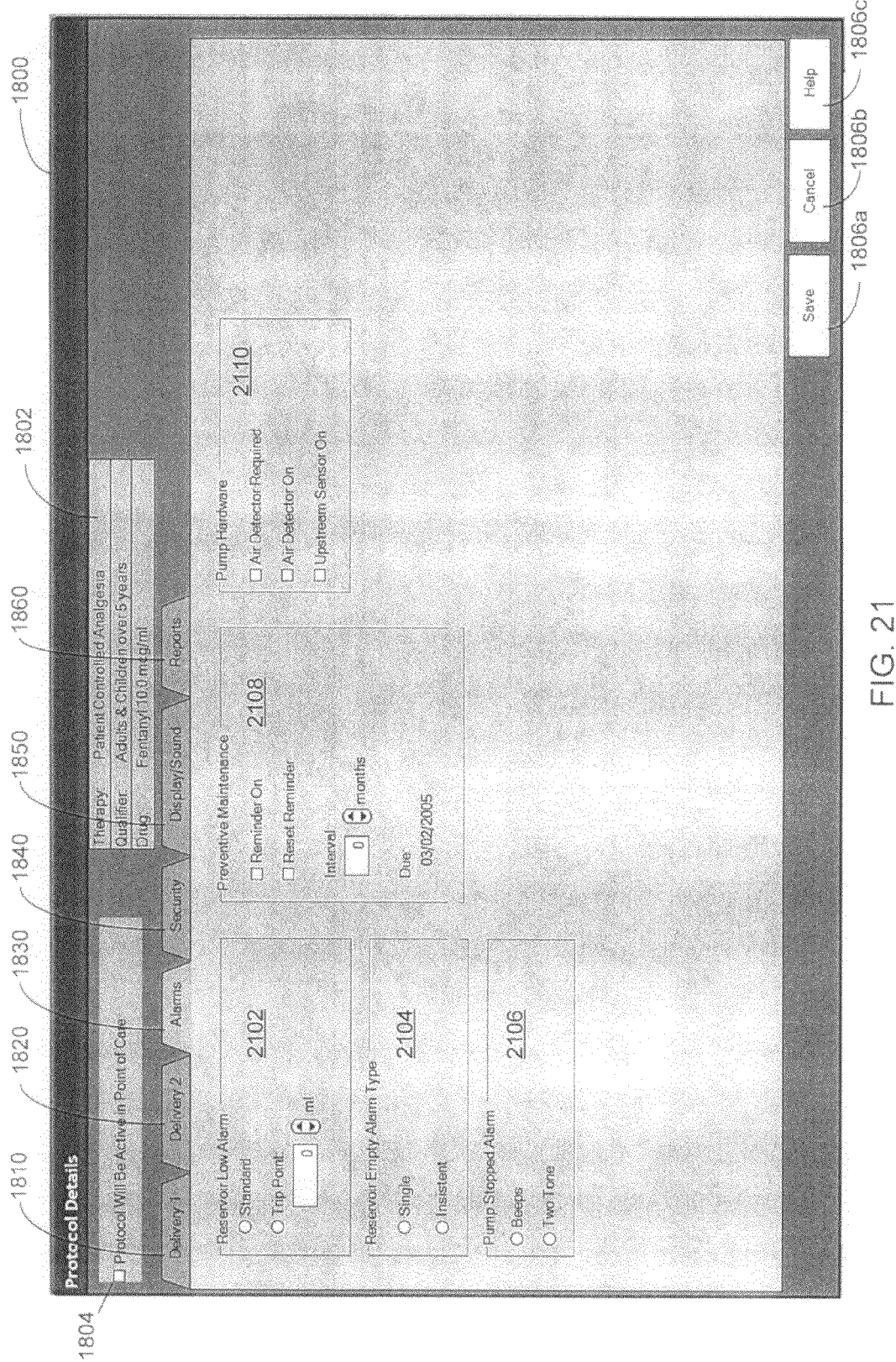
FIG. 21 is one example of a computer user interface alarm tab in accordance with the present disclosure.

FIG. 21 shows the parameter user interface 1800 with the alarm tab 1830 selected. The alarm tab includes a number of regions used for maintenance and hardware-related alarms, as opposed to the drug delivery threshold alarms discussed above in conjunction with the slider bars. The alarm tab 1830 allows the user to enable and disable alarms in the medical infusion pump. The alarm tab 1830 includes a reservoir low alarm region 2102, a reservoir empty alarm region 2104, a pump stop alarm 2106, a maintenance alarm 2108, and a hardware alarm 2110. The reservoir low alarm region 2102 provides an alarm indicator when a drug supply volume falls below a threshold level. The threshold level can be a standard level or an administrative user-set volume level. The reservoir empty alarm region 2104 sets a single occurrence or repeating alarm when a drug supply volume falls below a threshold level. The pump stop alarm 2106 sets an alarm which occurs when the medical infusion pump stops operating. The maintenance alarm 2108 enables a maintenance alarm, which alerts a user when maintenance is needed. The hardware alarm 2110 provides options for detection of optional components used with the infusion pump. For example, the hardware alarm 2110 can trigger upon detection of an air detector or other component. The pump hardware detector region 2110 can provide the option of enabling an alarm sent to a caregiver.

Figure 22:
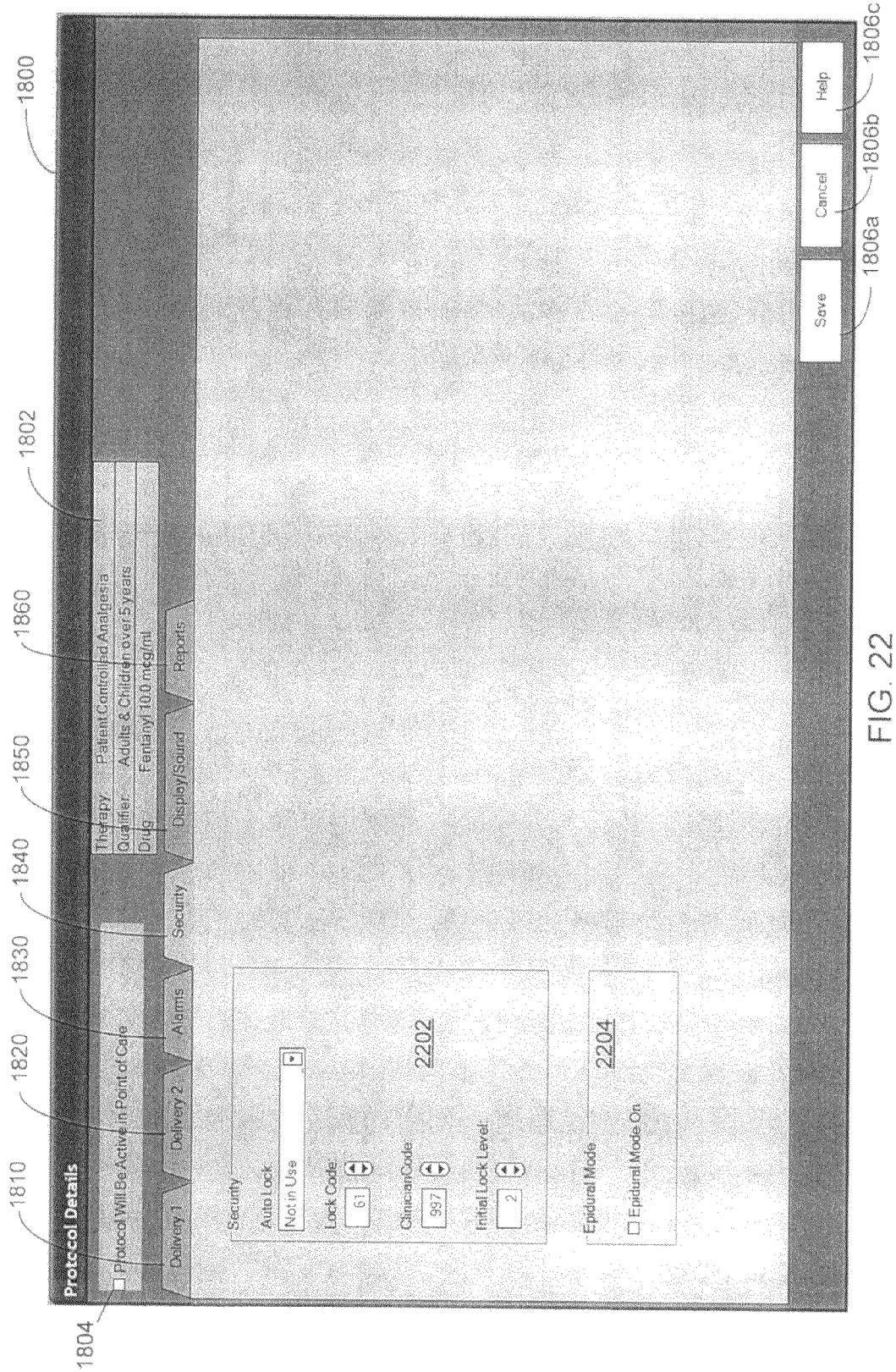
FIG. 22 is one example of a computer user interface security tab in accordance with the present disclosure.

FIG. 22 shows the parameter user interface 1800 with the security tab 1840 selected. The security tab 1840 includes options related to security of the medical infusion pumps. The security tab 1840 includes a security region 2202 and an epidural region 2204. The security region 2202 presents a number of security options for controlling access to each medical infusion pump. Security options can include an automatic lock, a lock code, clinician code, and an initial lock level. The epidural region 2204 selectably places the pump into a mode configured for epidural therapy.

Figure 23:
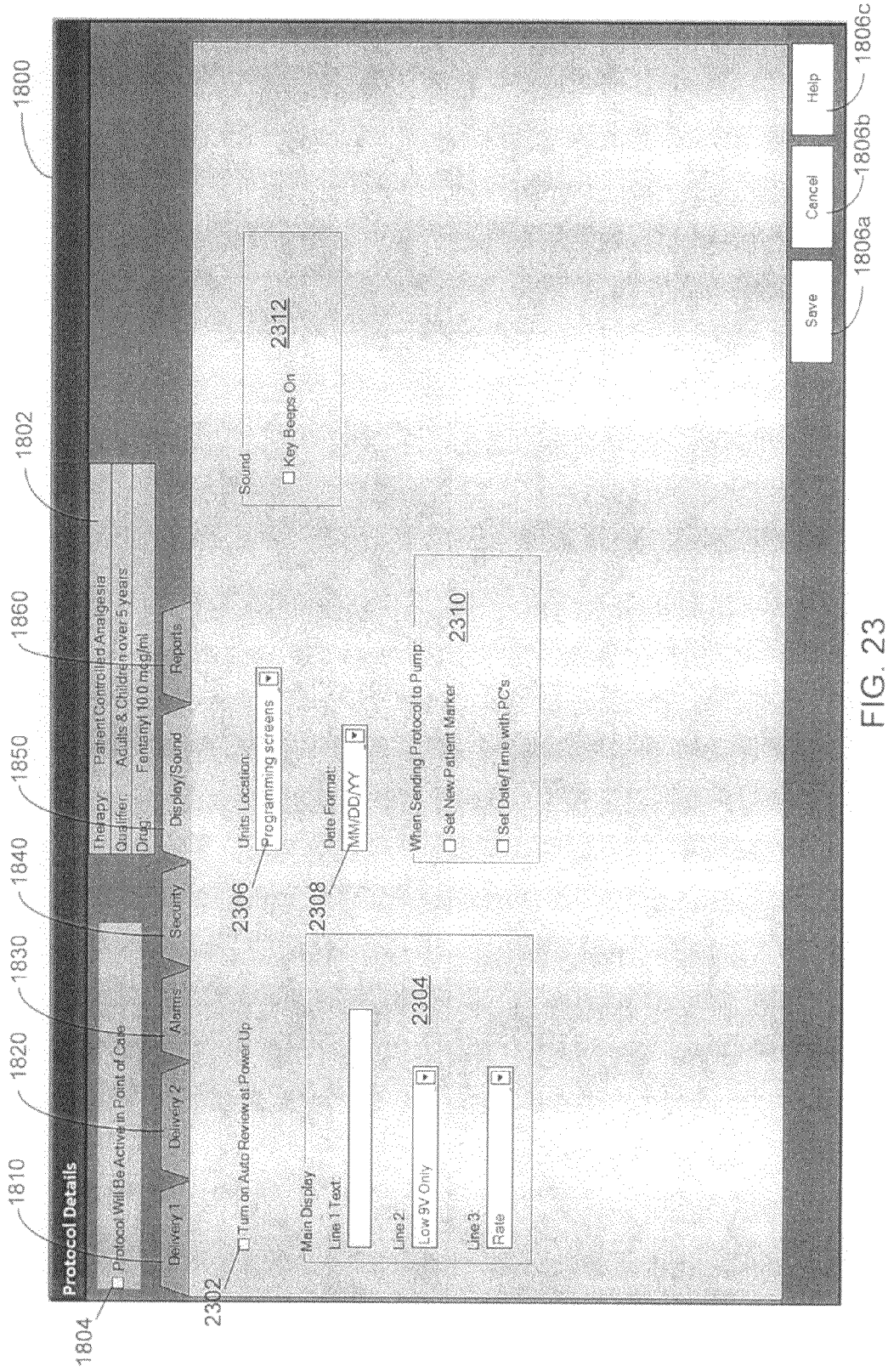
FIG. 23 is one example of a computer user interface appearance tab in accordance with the present disclosure.

FIG. 23 shows the parameter user interface 1800 with the display/sound tab 1850 selected. The display/sound tab 1850 includes options related to the display and sound settings for each medical infusion pump. The display/sound tab 1850 includes an auto-review option 2302, a main display region 2304, a units option 2306, a date format option 2308, a send protocol region 2310, and a sound region 2312. The auto-review option 2302 enables a power-up display of options in the medical infusion pump. The main display region 2304 presents a number of programmable fields that will, by default, be displayed on the medical infusion pump. For example, the main display region 2304 includes programmable text display entry, power source information, and drug delivery rate. Other display options related to properties of the medical infusion pump are available as well. The units option 2306 selectably assigns a units location for display on the medical infusion pump. The date format option 2308 assigns date formats for displaying on the medical infusion pump. The send protocol region 2310 sets one or more patient markers or date/time stamps in the infusion pump network upon distribution of programming instructions to the medical infusion pump. The sound region 2312 enables sound in the medical infusion pump, such as beeping sounds when one or more keys/key sequences are depressed.

Figure 24:
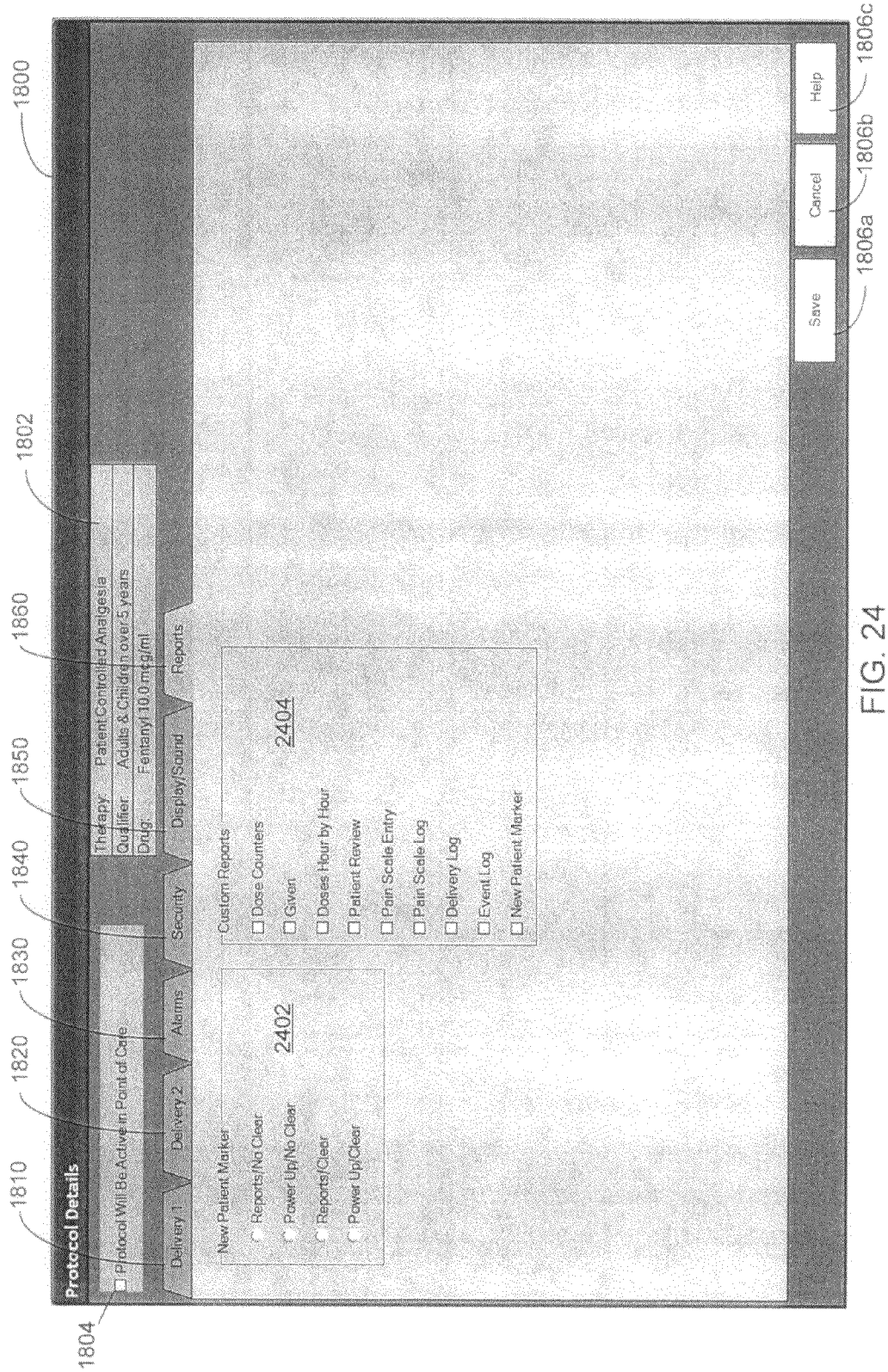
FIG. 24 is one example of a computer user interface report tab in accordance with the present disclosure.

FIG. 24 shows the parameter user interface 1800 with the report tab 1860 selected. The report tab 1860 presents options for displaying reports by a medical infusion pump related to events occurring in the pump. The report tab 1860 includes a new patient marker region 2402 and a custom report region 2404. The new patient marker region 2402 includes a list of options to perform related to report generation upon association of a medical infusion pump with a new patient. For example, the new patient marker region 2402 includes a number of report-clearing options and power-on options to be performed when a medical infusion pump is assigned to a new patient. The custom report region 2404 provides a number of selectable options for display in a custom report regarding events tracked in the medical infusion pump network. The custom report region 2404 provides all of the options tracked in the infusion pump network 500, which can be stored in the log files 516. A user selects one or more of the options to generate a report. For example, the custom report region 2404 can include dose counters, doses per hour, pain scale information, drug delivery information, an event log, and a patient marker. The report generated by the custom report region 2404 options displays on the screen of the medical infusion pump 102 or computing system, 104. Both the new patient marker region 2402 and the custom report region 2404 can include additional options as well.

Figure 25:
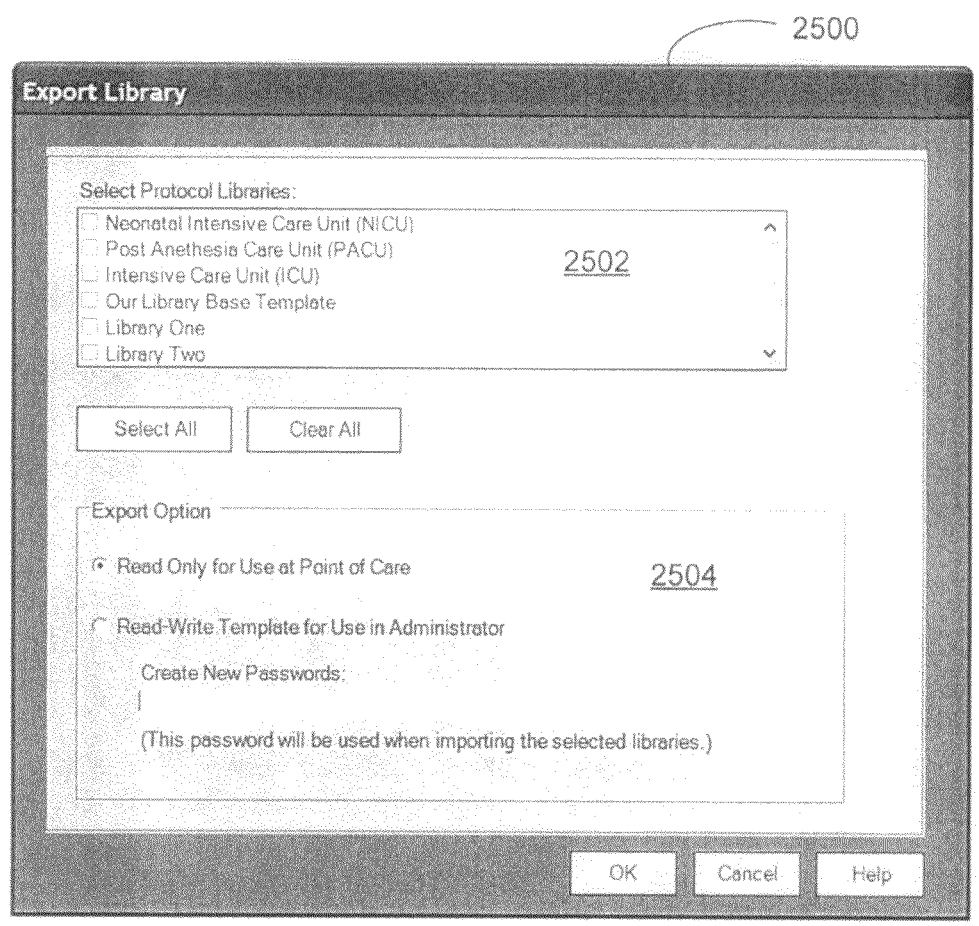
FIG. 25 is one example of a computer user interface library export screen in accordance with the present disclosure.

Referring now to FIG. 25, a library export screen 2500 is optionally used to save the pump parameters and protocols for exporting from the database 504 of FIG. 5. One or more libraries are exported using the library export screen 2500, including all of the pump protocols, and containing all of the defined therapies, qualifiers, drugs, and combinations thereof. The library export screen 2500 corresponds to the export library module 724 of FIG. 7, and provides file extraction, in that one or more protocol libraries built using the administrative software 700 are exported to a data file or database. The export library screen 2500 includes a library field 2502 and an export option region 2504. The library field 2502 displays a number of libraries available to the system that can be exported to a portable file. The export option region 2504 provides export options to the administrative user seeking to export the library data to a file. For example, export options can include creating a read-only file, or a read-write template for use in another instantiation of the software system disclosed herein. The read-only file might be selected in the case that the library is to be loaded onto a medical infusion pump that is disconnected from the database 504 of FIG. 5. The read-write file might be selected if the library is to be transferred to a separate infusion pump network 500 altogether, in which administrative software on that subsequent infusion pump network may be used to subsequently edit that library. Additionally, the export option region 2504 includes an assignable password to add security to the library file exported such that a user attempting to access the protocols contained in the library file must know and enter the correct password.

The above description and figures corresponding to the administrative software 700 provides a therapy-centric programming schema for a medical infusion pump. For example, a certain drug used in conjunction with a medical infusion pump may be appropriate for use with a specific therapy for an adult, but may not be appropriate for the same therapy for a child. Certain drugs may only be appropriate in certain therapies, and under certain qualifying conditions. Pump parameters are initially set according to the protocols defined in the administrative software 700, but are customizable on a pump-by-pump basis using user software associated with a specific pump and/or patient.

Figure 26:
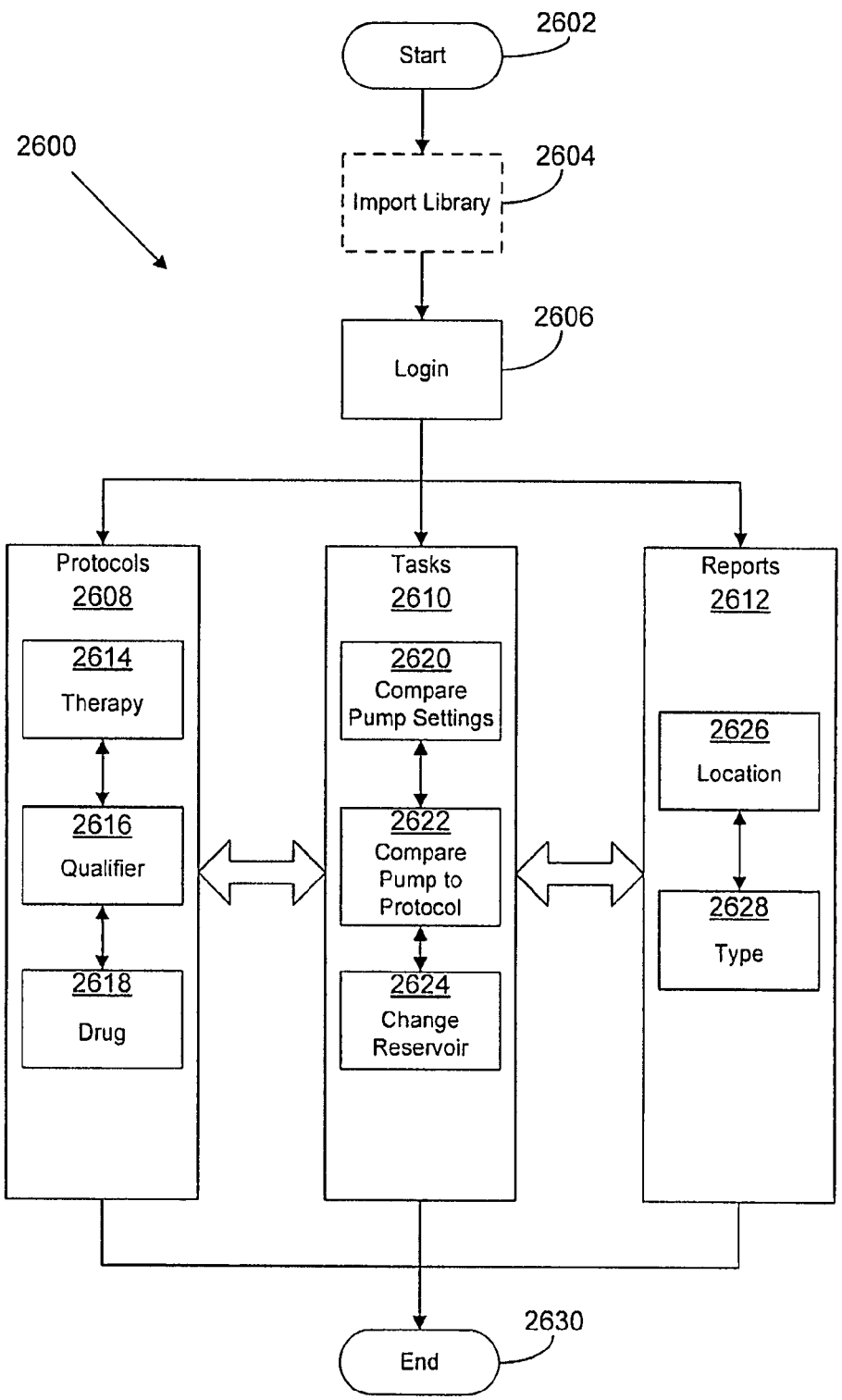
FIG. 26 is a flow diagram of methods and systems for custom programming of a medical infusion pump according to a possible embodiment of the present disclosure.

FIG. 26 illustrates exemplary architecture of user software 2600 for accessing a pump application program and programming a medical infusion pump. The software 2600 can operate within the pump 102, computing system 104, or a combination thereof. The user software 2600 allows a user, for example a doctor, nurse, pharmacist, or other caregiver, to select and customize pump application protocols, and parameters for execution in and control of a medical infusion pump 102. Depending upon the pump configuration, the user may select a protocol or a library for loading into a medical infusion pump. Additional data structures could be loaded into the medical infusion pump as well. Although the user software 2600 is discussed in conjunction with the administrative software 700 previously described in FIGS. 7-25, it is understood that the user software systems described herein are operable in conjunction with additional hardware/software embodiments.

The medical infusion pumps as described store pump data in memory, such as the memory shown above in FIG. 3. The pump data can include pump parameters, parameter values, programs, and other functional and data systems configured to operate the medical infusion pump. As referred to herein, a set of pump parameters can include the entire memory contents of the pump, or can include a subset of the memory contents, such as selected data values, that can be altered to change operation of the pump.

The user software 2600 is instantiated by a start module 2602. The start module 2602 corresponds to initial execution of the user software 2600 by clicking on an icon on the computer or by some other mechanism for executing software. Upon execution of the start module 2602, the user software 2600 connects to a library on a server 206 containing one or more pump protocols.

Following the start module 2602, operational flow optionally proceeds to a library import module 2604. The library import module 2606 provides the ability to import one or more libraries into the software 2600. This feature can be used by a computing system 104 or medical infusion pump 102 that is not connected to the same medical infusion pump network 500 as the database storing the library 504. If the computing system 104 or medical infusion pump 102 is connected to the medical infusion pump network 500, each component is by default connected to the server 206 and database 504.

The libraries available to be imported include pump protocols and parameters, and may have been created using the administrative software of FIGS. 7-25. The collection of pump protocols can be accessed from the server 206 or in one or more individual computing systems 102. The library import module 2604 allows the user to select one or more pump application programs for downloading to a medical infusion pump 102.

Once connected to the desired library either by default or via the library import module 2604, operational flow proceeds to a login module 2606. The login module 2606 regulates user rights in the software 2600 by controlling access to the libraries 508 in the database 504 of FIG. 5. User rights define access levels in the software for users such as doctors, nurses, other caregivers, or patients. A user will have a set access level allowing the user to view or edit pump application protocols and parameters within the user software 2600. Access levels are set using the user rights module 716 of the administrative software 700, described above in conjunction with FIG. 7. Access levels can be set by a user of the administrative software 700 according to a variety of criteria, such as the type of caregiver (e.g., physician, nurse, or pharmacist).

Different access levels also can provide different rights with respect to pump operational parameters. For example, one access level might give a user a right to edit patient specific pump parameters. One access level might permit a user the right to only view and download the patient specific pump operational parameters. Different embodiments can include the ability to provide an access level for a user any combination of rights to edit, view, and/or download pump operational parameters, protocols, or libraries.

Once the user is logged in, the user selectively executes three different modules, a protocol selection module 2608, a task module 2610, and a report module 2612.

The protocol selection module 2608 selects a protocol for use with a medical infusion pump from the protocols loaded in the user software 2600. The protocol selection module 2608 guides the user through selection of a therapy, qualifier, and drug combination defined to be a protocol by the administrative software. The protocol selection module 2608 includes a therapy selection module 2614, a qualifier selection module 2616, and a drug selection module 2618 for this purpose. The therapy selection module 2416 selects a therapy to be administered by the drug infusion pump 102. The therapy is one of the therapies included in the library selected in the library import module 2606. The qualifier selection module 2616 selects a qualifier from those associated with the therapy in the library. The drug selection module 2618 selects a drug associated with the therapy and drug. The protocol selection module 2608 further allows customization of the protocol by allowing a user to modify pump parameters, such as the drug delivery rate, the demand dose, the demand dose lockout, drug delivery limits, and reservoir volume.

The task module 2610 guides a user through maintenance and monitoring tasks that are required for each medical infusion pump 102. These maintenance and monitoring tasks can include pump settings comparison and testing, as well as changing the reservoir holding the drug delivered by the medical infusion pump 102. The task module 2610 includes a pump settings module 2620, a comparison module 2622, and a reservoir module 2624. The pump settings module 2620 compares the local pump settings to a standing order set for the pump, for example by a caregiver who programmed or customized the medical infusion pump. During operation of the pump settings module 2620, the user software 2600 receives a GUID specific to a protocol and generated by the server 206, and stores the GUID on the pump or computing system. The GUID generated by the server and stored on the pump or computing system is made available to the server when the pump or computing system accesses the library to look up and verify the future access of the correct protocol and/or library. This ensures that the pump settings are compared to the correct protocol stored on the server. The comparison module 2622 compares the local pump settings to a protocol, such as the protocols defined using the administrative software 700. The reservoir module 2624 determines if a drug reservoir is nearly empty and guides a patient or caregiver through the drug cartridge changing process occasionally required during use of a medical infusion pump.

The report module 2612 generates a report from preexisting logged information for a selected medical infusion pump 102. The report module includes a location module 2626 and a type module 2628. The location module 2626 requests the location of the pump from which a report is generated, such as a specific pump or a previously saved report stored on the pump or computing system. The type module 2628 presents a number of types of reports which can be generated from the logged information, such as a drug delivery report or event log, and can display the report responsive to a user request.

Operation of the software terminates at an end module 2630. The end module 2630 corresponds to termination of the administrative software 2600 by clicking on a close window button on the computer or by some other mechanism for terminating execution of software.

Figure 27:
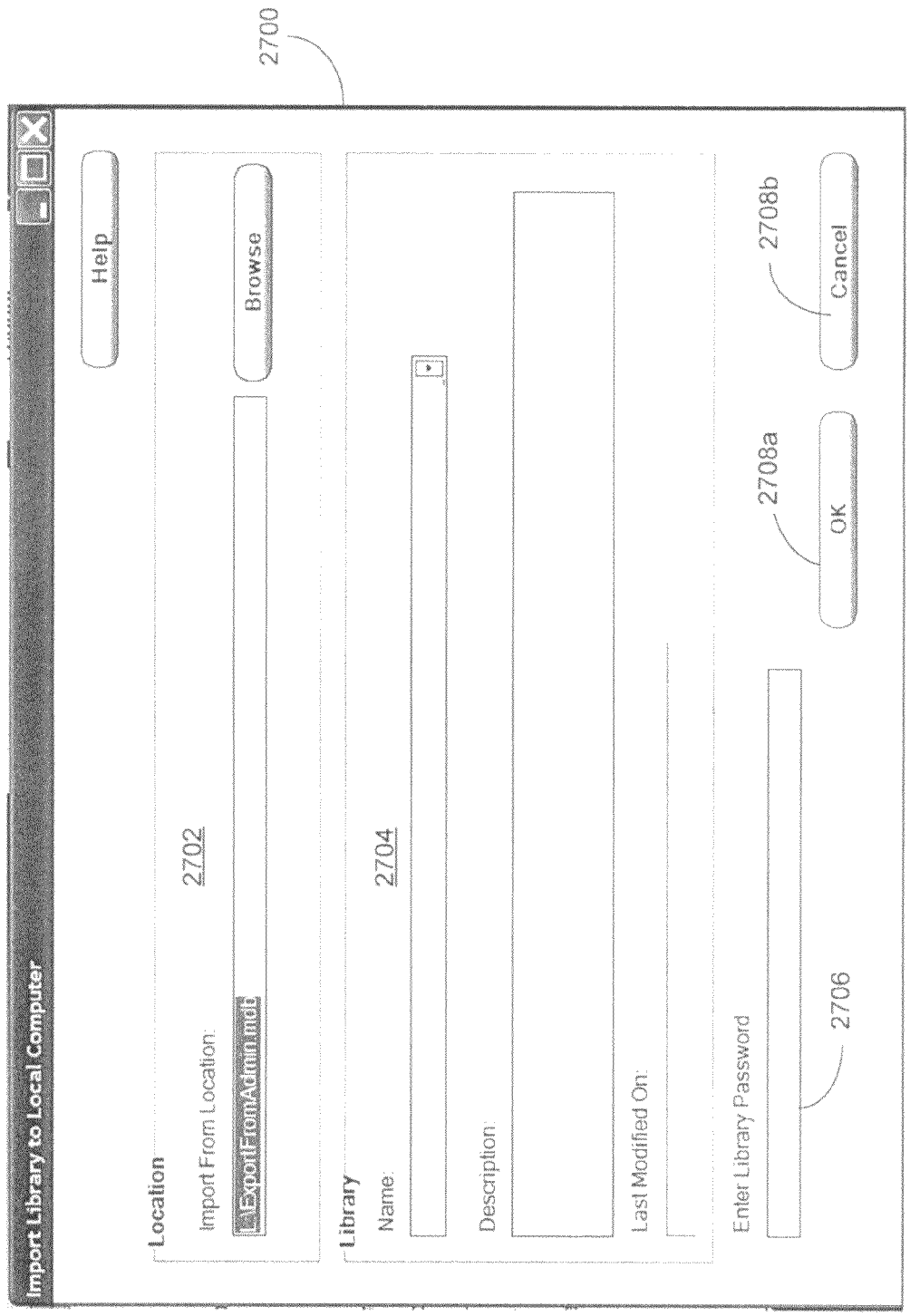
FIG. 27 is one example of a computer user interface library import screen in accordance with the present disclosure.

FIG. 27 shows a library import screen 2700 used to optionally load a library of pump protocols into the user software 2600. The library import screen 2700 corresponds to the login module 2604, and presents a location field 2702 and a library field 2704 used to browse to and select a library from a library database or file. An optional password field 2706 accepts user input to allow the user to enter a password for accessing a password protected library file, such as one created using the export library screen shown in FIG. 25. Control buttons 2708a-2708b provide confirmation and cancellation options to the user, allowing the user to complete the library access process.

FIGS. 28-32 illustrate an exemplary process and user interface through which the protocol selection module 2608 leads a user to select a protocol for use with a medical infusion pump. The methods, systems and user interfaces described in conjunction with FIGS. 28-32 can be performed either on a computing system, such as a computing system 104 associated with a medical infusion pump 102, or on a medical fusion pump 102 configured to accept a library of pump protocols directly. Medical infusion pumps 102 accepting a single pump protocol use a corresponding computing system 104.

Figure 28:
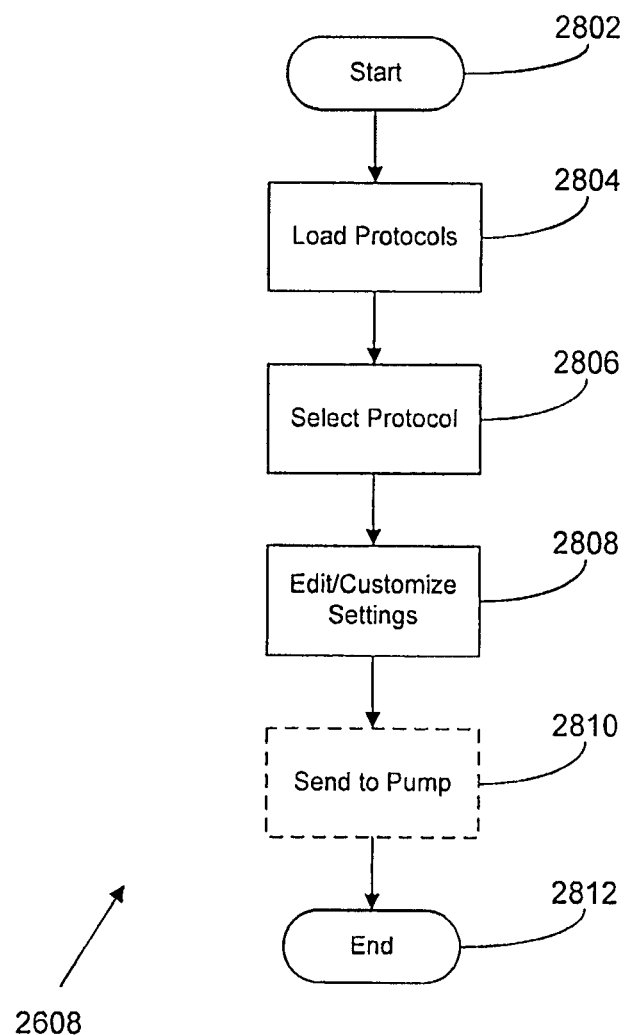
FIG. 28 is a flow diagram of methods and systems for editing and loading a protocol for a medical infusion pump according to a possible embodiment of the present disclosure.

Referring to FIG. 28, operation of the protocol selection module 2608 is instantiated by a start module 2802. The start module 2802 corresponds to initial execution of the user software 2600, or initial selection of the protocol selection module 2608 by clicking on an icon or tab on the computer or by some other mechanism for executing software.

Following the start module 2802, operational flow proceeds to a load protocols module 2804. The load protocols module 2804 populates the user software 2600 with the protocols from the loaded library. For example, the load protocols module 2804 can populate a listing of protocols for selection using the user software 2600.

Following the load protocols module 2804, operational flow proceeds to a select protocol module 2806. The select protocol module 2806 selects a protocol from among the protocols loaded into the user software 2600 by guiding a user through selection of a therapy, qualifier, and drug defining one of the protocols loaded in the software 2600. The select protocol module 2806 corresponds to the therapy selection module 2614, qualifier selection module 2616, and drug selection module 2618 shown in FIG. 26.

Following the select protocol module 2806, operational flow proceeds to a settings module 2808. The settings module 2808 provides editing and customization of the pump parameters assigned to a medical infusion pump as dictated by the protocol selected by the user. The parameters include, for example, the drug delivery rate, demand dose rate, or demand dose lockout.

Following the settings module 2808, operational flow proceeds to an optional pump programming module 2810. The pump programming module 2810 programs a medical infusion pump with the settings both as defined by the protocol and selected by the select protocol module 2806, and as customized by the settings module 2808. The pump programming module 2810 executes if the user software 2600 resides on a computing system 104 connected to a medical infusion pump 102. The pump programming module may not execute if the software 2600 resides on the medical infusion pump 102 itself, because the protocols are already loaded into the pump alongside the library accessed by the user software 2600.

After the pump programming module 2810 completes, operation of the protocol selection module 2608 terminates at an end module 2812. The end module 2812 corresponds to successful programming of the medical infusion pump.

FIGS. 29-32 illustrate a user interface 2900 used to guide a caregiver through the pump programming process. The user interface 2900 operates on a computing system associated to a medical infusion pump. The user interface 2900 includes a login button 2902, a connection status indicator 2904, a library indicator 2906, and a protocol tab 2920, a tasks tab 2940, and a reports tab 2960.

The login button 2902, when selected, generates a login screen that checks whether a user has the right to access pump programs, protocols, or parameters. The connection status indicator 2904 displays the connection status of the user software. Connection status can include a connection to a medical infusion pump or connection to a networked server. The library indicator 2906 displays the current library loaded using the library import screen 2700 of FIG. 27.

Figure 29:
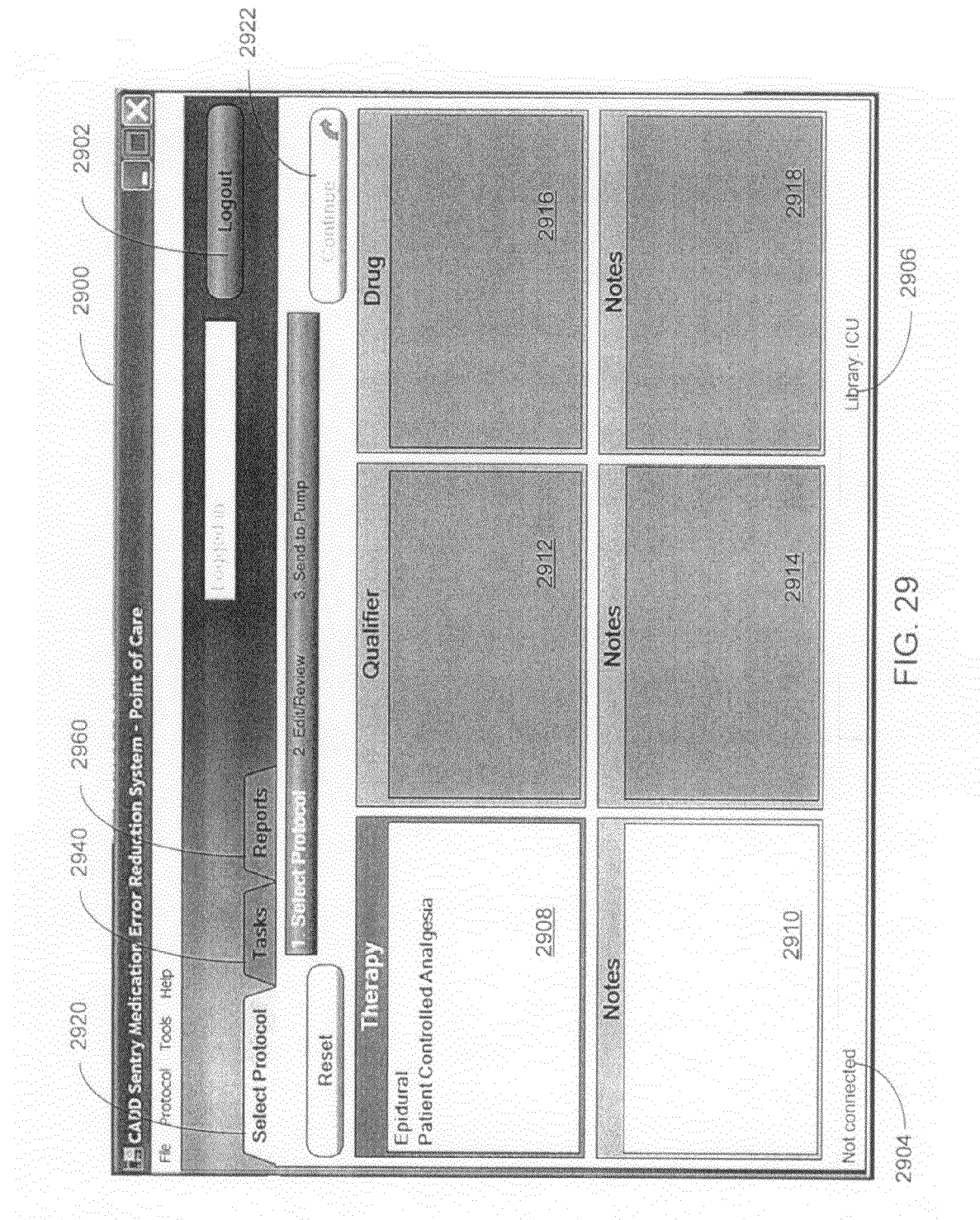
FIG. 29 is one example of a computer user interface protocol selection screen in accordance with the present disclosure.

Referring now to FIG. 29, the user interface 2900 is shown with the protocol tab 2920 selected. FIG. 29 corresponds to an initial state of the protocol selection module 2608 following the load protocols module 2804 of FIG. 28. The protocol tab 2920 guides a user through the process of selecting a protocol, customizing one or more parameters in the protocol, and programming a medical infusion pump with the customized pump program. The protocol tab includes a therapy selection field 2908, a therapy notes field 2910, a qualifier selection field 2912, a qualifier notes field 2914, a drug selection field, 2916, a drug notes field 2918, and a continue button 2922.

The therapy selection field 2908 lists the therapies included in the currently loaded library. For example, the two therapies shown are "Epidural" and "Patient Controlled Analgesia". The therapy notes field displays the notes associated with the selected therapy. In the initial state, the therapy selection field 2908 and therapy notes field 2910 are active, and the qualifier fields 2912, 2914, drug fields 2916, 2918, and continue button 2922 are inactive. No therapy is initially selected in the therapy listing field 2908, so the therapy notes field 2910 remains empty.

Figure 30:
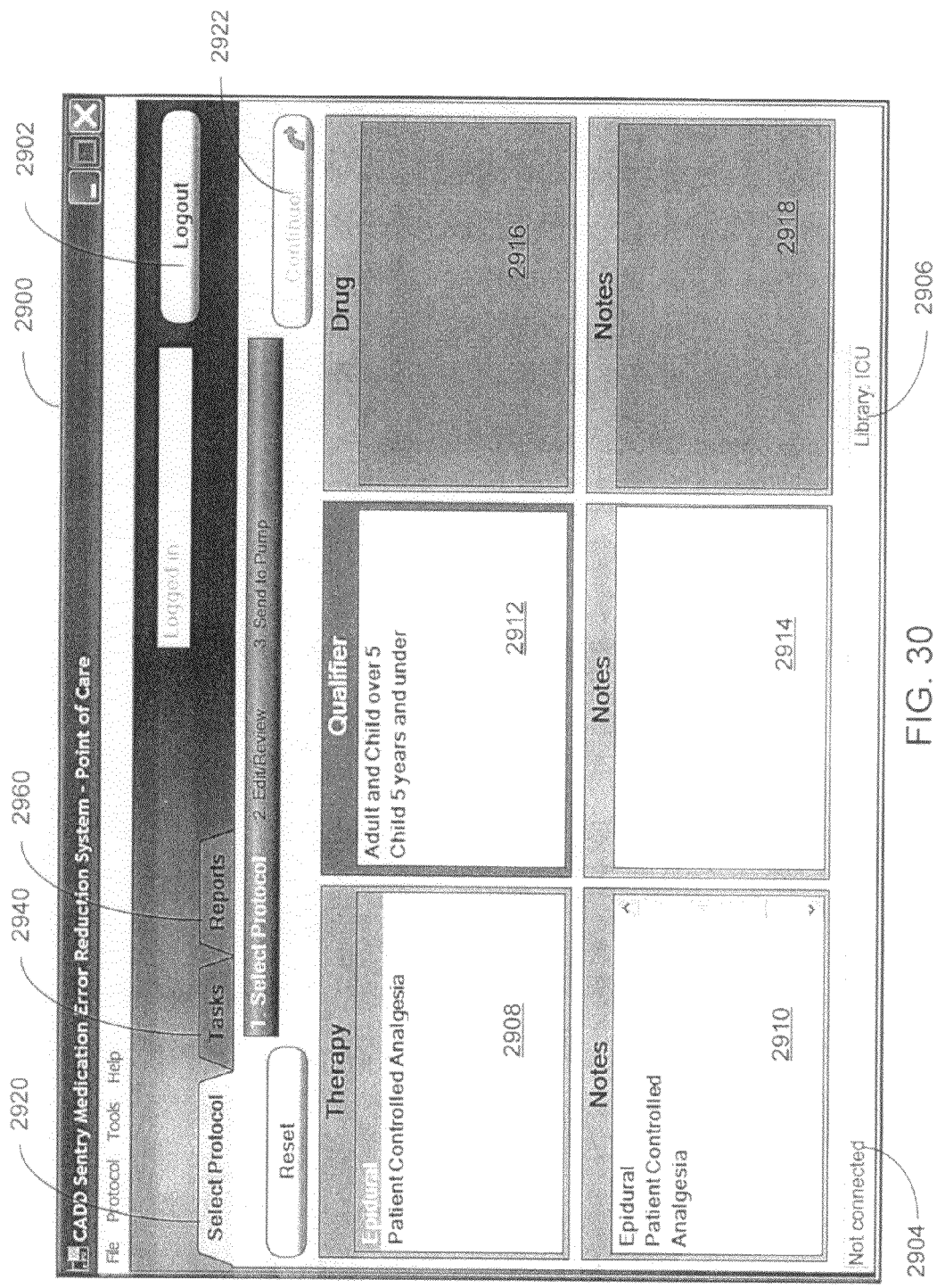
FIG. 30 is one example of a computer user interface therapy selection screen in accordance with the present disclosure.

FIG. 30 shows the user interface 2900 with the protocol tab 2920 selected and a therapy selected from the therapy selection field 2908. Notes related to the selected therapy appear in the therapy notes field 2910, and the qualifier selection field 2912 and qualifier notes field 2914 activate. A listing of qualifiers associated with the selected therapy appears in the qualifier selection field 2912. The therapy notes shown recite "Epidural Patient Controlled Analgesia" corresponding to the selected therapy, but could contain particular information related to the therapy, such as warnings, descriptions, or other information about application of the therapy. The qualifiers, which appear once the therapy is selected, are shown to include "Adult and Child over 5" and "Child 5 years and under". No qualifier is initially selected, so the qualifier notes field 2914 remains empty. The drug selection field 2916, drug notes field 2918, and the continue button 2922 remain inactive.

Figure 31:
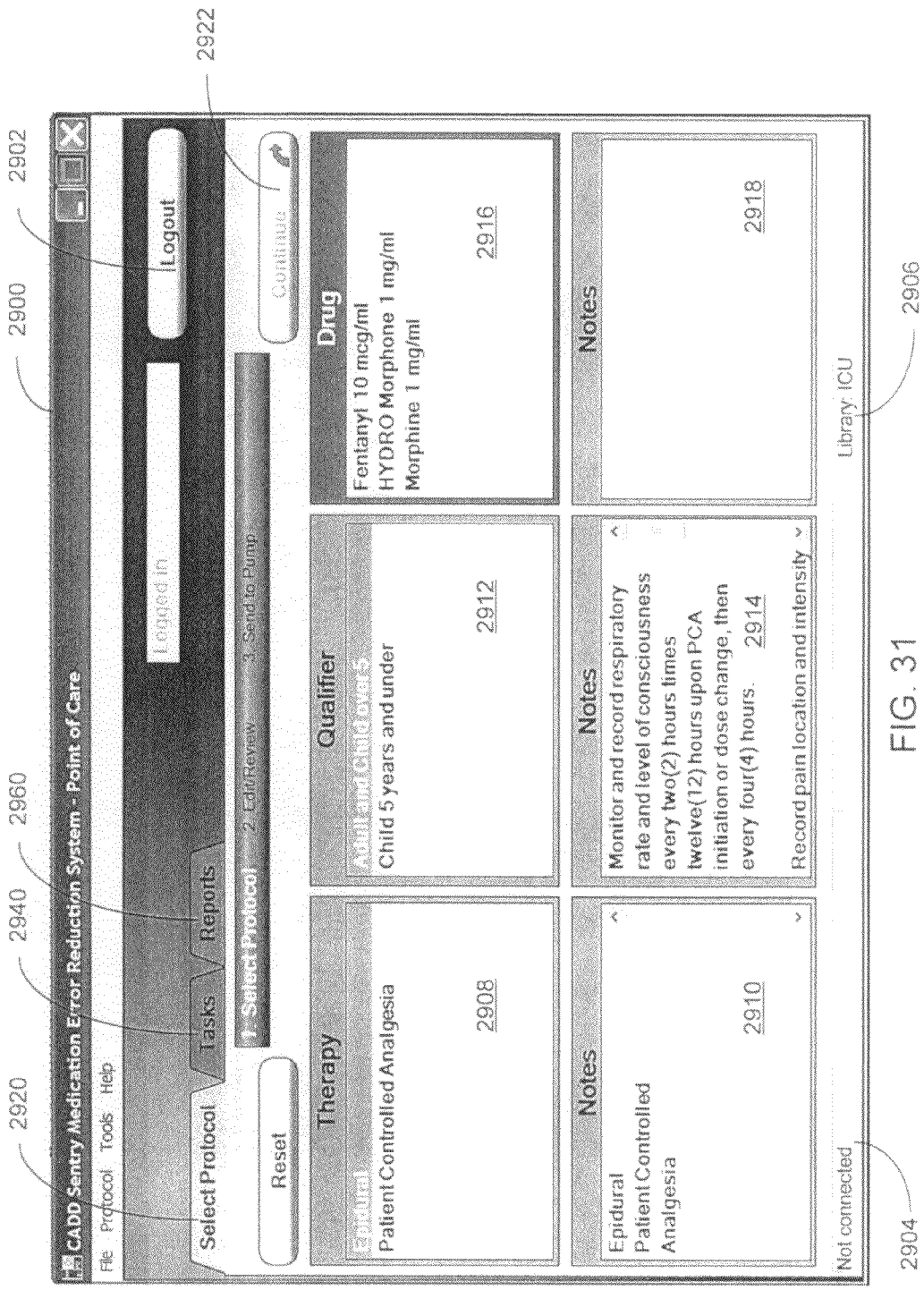
FIG. 31 is one example of a computer user interface qualifier selection screen in accordance with the present disclosure.

FIG. 31 shows the user interface 2900 with the protocol tab 2920 selected and both a therapy selected from the therapy selection field 2908 and a qualifier selected in the qualifier selection field 2912. Notes related to the qualifier appear in the qualifier notes field 2914, and the drug selection field 2916 and drug notes field 2918 are active. For example, "Adult and Child over 5" is shown to be, and the qualifier notes field 2914 displays specific notes applicable to those patients. A listing of drugs associated with the therapy and qualifier appears in the drug selection field 2916. Three exemplary drug menu listings including "Fentanyl 10 mcg/ml", "HYDRO Morphine 1 mg/ml" and "Morphine 1 mg/ml" are shown. No drug is initially selected, so the drug notes field 2918 remains empty. The continue button 2922 remains inactive.

Figure 32:
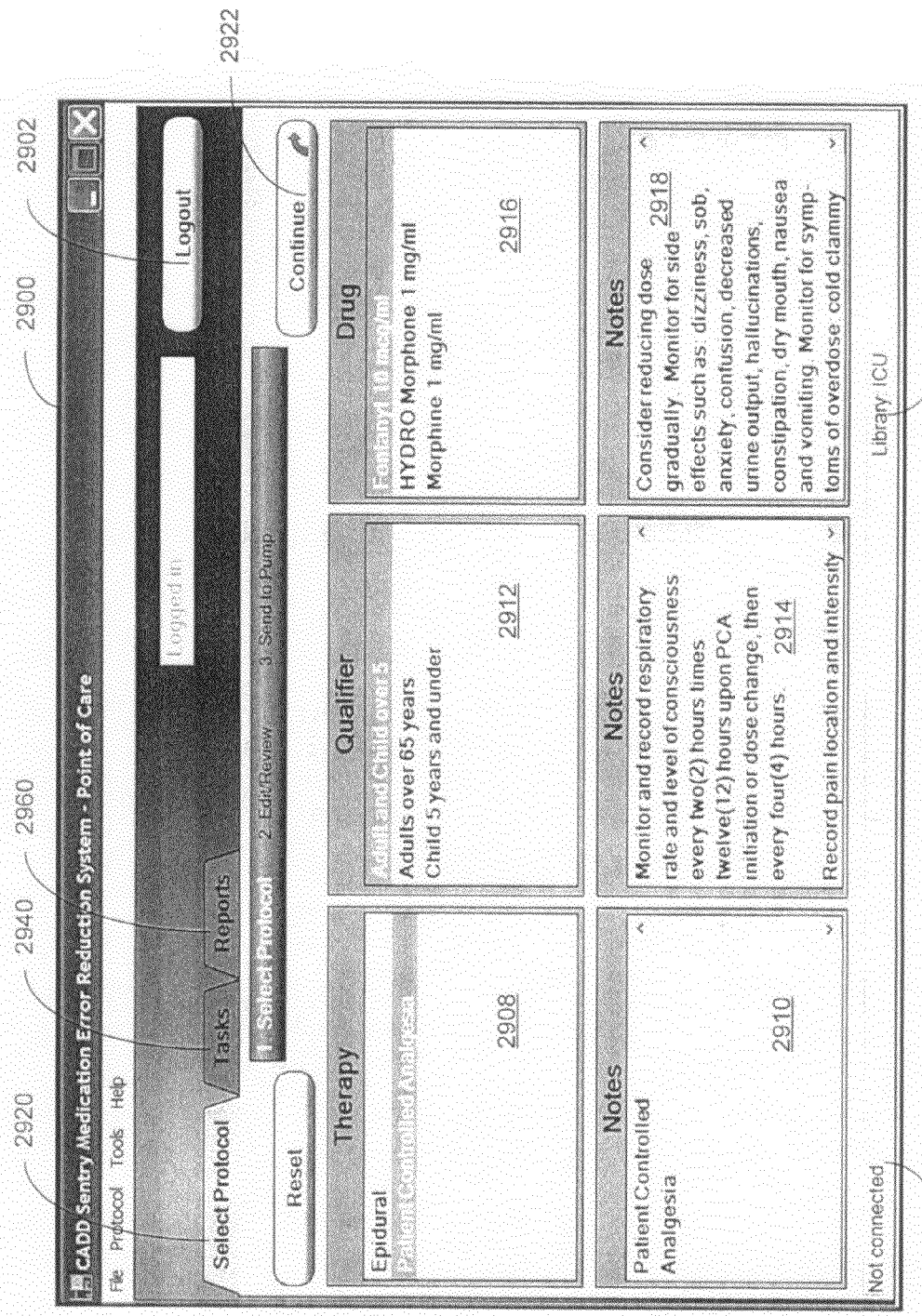
FIG. 32 is one example of a computer user interface drug selection screen in accordance with the present disclosure.

FIG. 32 shows the user interface 2900 with the protocol tab 2920 selected and a therapy, qualifier, and drug selected in each of the respective selection fields 2908, 2912, and 2916. Once a therapy, qualifier, and drug are selected a specific protocol is designated from among the protocols defined in the administrative software 700. Each notes field 2910, 2914, and 2918 displays information related to the selected therapy, qualifier, and drug, respectively. The continue button 2922 activates, allowing the user to continue with customization of the selected protocol by changing one or more pump parameters related to the therapy, qualifier, and drug.

Figure 33:
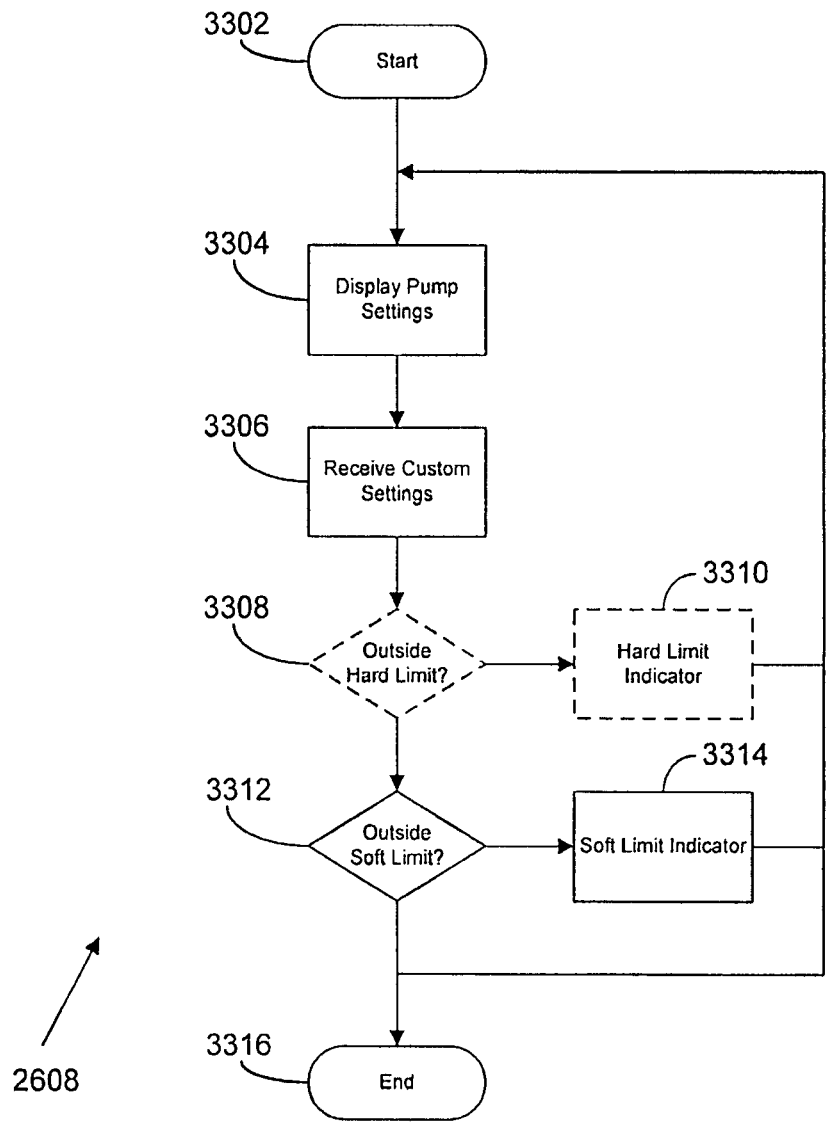
FIG. 33 is a flow diagram of methods and systems for custom programming of a medical infusion pump according to a possible embodiment of the present disclosure.

FIG. 33 illustrates an exemplary process by which the administrative software 2600 customizes one or more parameters of a selected pump protocol, and corresponds to the settings module 2608 of FIG. 26. The settings module 2608 allows customization of one or more pump parameters while monitoring whether the customized value is within an acceptably safe dosage or drug delivery range.

The settings module 2608 is instantiated by a start module 3302. The start module 3302 corresponds to selection of the confirmation button 2922 of FIGS. 29-32.

Following the start module 3302, operational flow proceeds to a display module 3304. The display module 3304 displays the default protocol settings of the protocol loaded onto a medical infusion pump screen or a computing system associated with the pump. The display module 3304 presents a number of meters to a user related to the drug delivery rates and other parameters controlled by the pump. The meters provide user controls for modifying one or more pump parameters.

In various embodiments, the display module 3304 can be configured to display a variety of coloring and image features. In one possible embodiment, the meters are slider bars that can include graphical thresholds set by the administrative software. A cautionary color change of the user interface (i.e. green or gray to yellow or red) can represent a warning to the user that the current setting is outside of the administratively set thresholds.

In another possible embodiment, the overall background color of the user interface is color-coded to correspond to hospital coding procedures, and can represent one or more location-specific warning or status conditions. Additionally, the color coding can be located behind an image displayed on the pump screen, and can be keyed to a location of the medical infusion pump, the drug administered, or a warning condition within the pump.

Following the display module 3304, operational flow proceeds to a custom settings module 3306. The custom settings module 3306 receives the current customized pump settings based on user-customization of one or more pump parameters. The custom settings module 3306 can provide a user customization interface for setting pump parameters to values other than the initial or default values set in the administrative software 700.

Following the custom settings module 3306, operational flow depends upon the implementation of the hard limits and soft limits in the administrative software 700. If the hard limit gauges in FIGS. 18-20 provide a warning but do not dictate an absolute maximum/minimum for the range of programmable values within the user software 2600, operational flow proceeds to a hard limit determination operation 3308. If the hard limit gauges dictate an absolute maximum/minimum for the range of programmable values within the user software 2600, the hard limit will likely not be exceeded, so operational flow proceeds directly to the soft limit determination operation 3312.

The optional hard limit determination operation 3308 determines if the pump settings are outside the "hard limits" set in the administrative software 700. If the pump settings exceed the hard limit (i.e. above the maximum or below the minimum value), operational flow branches "yes" to a hard limit indicator module 3310. If the pump settings do not exceed the hard limit, operational flow branches "no" to a soft limit determination operation 3312.

The optional hard limit indicator module 3310 executes in conjunction with the hard limit determination operation 3308, and generates an indicator to a user that the hard limit set in the administrative software is exceeded by the current settings of the medical infusion pump. If the hard limit determination operation 3308 is bypassed or otherwise absent from the user software 2600, the hard limit indicator module 3310 can be absent/bypassed as well. The hard limit indicator module 3310 creates an alert indicator on the display of the pump or associated computing system, or sends an alert to the server or other computing system to alert a caregiver that an alert condition has been reached by the pump due to exceeding the hard limit. Operational flow proceeds to the display module 3704 to update the display and to allow additional user modification of the pump settings.

The soft limit determination operation 3312 determines if the pump settings are outside the "soft limits" set in the administrative software 700. If the pump settings exceed the soft limit, operational flow branches "yes" to a soft limit indicator module 3314. If the pump settings do not exceed the soft limit, operational flow branches "no" to return to the display module 3304.

The soft limit indicator module 3314 generates an indicator to a user that the soft limit set in the administrative software is exceeded by the current parameter settings. The soft limit indicator module 3314 creates an alert indicator different from the hard limit indicator module 3310 if the hard limit indicator module 3310 exists or executes within the software 2600. For example, the soft limit alert indicator can be a different color, display a different message, or send a different alert to a remote medical care provider.

Following the soft limit indicator module 3314, operational flow proceeds to the display module 3304 to update the display and allow additional user modifications of the pump settings. Upon termination of operation of the medical infusion pump, operational flow terminates at the end module 3316.

Figure 34:
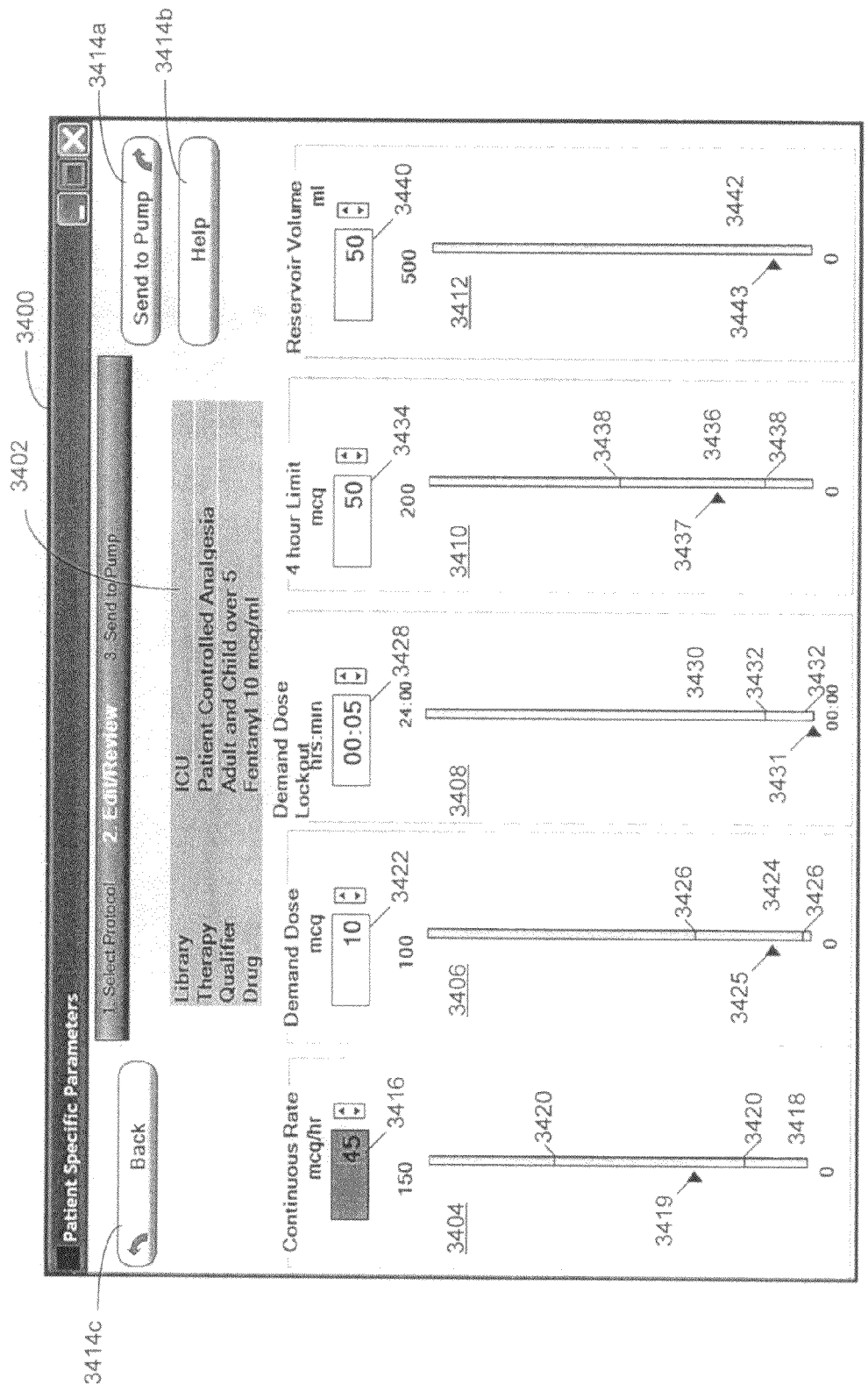
FIG. 34 is one example of a computer user interface drug delivery customization screen in accordance with the present disclosure.
Figure 35:
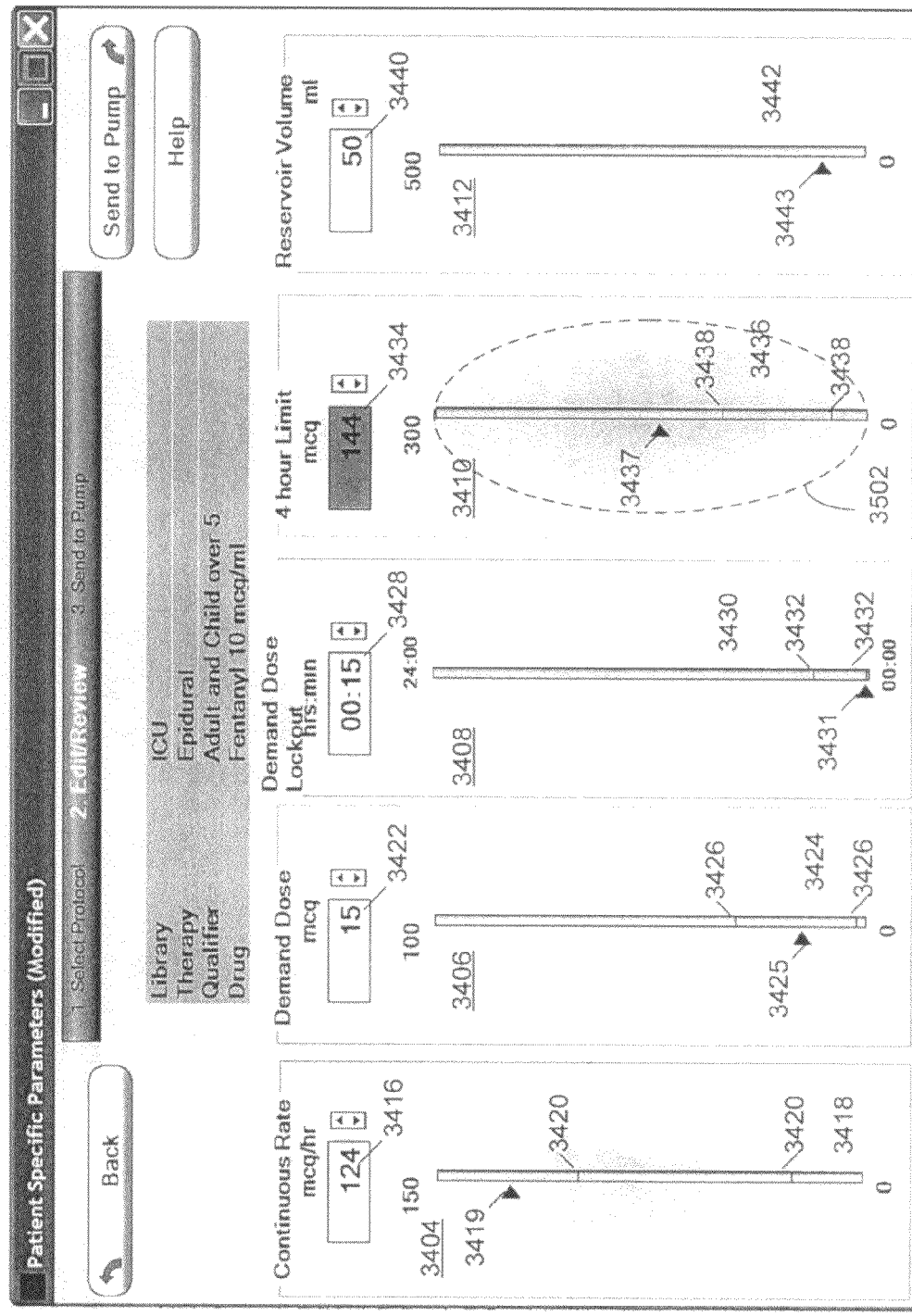
FIG. 35 is one example of a computer user interface drug delivery customization screen in accordance with the present disclosure.

Referring now to FIGS. 34-35, an exemplary user interface 3400 for customizing pump parameters is shown. The user interface 3400 corresponds to the settings module 2808 of FIG. 28, and operates generally as described in FIG. 33. The user interface 3400 includes a status indicator 3402, a continuous rate region, 3404, a demand dose region 3406, a demand dose lockout region 3408, a timed limit region 3410, and a reservoir region 3412. The user interface 3400 further includes control buttons 3414a-3414c.

The regions 3404-3412 correspond to the patient specific pump parameters 512a of FIG. 5, and can include one or more of continuous rate, demand dose, demand dose lockout, timed limits, reservoir volume, and other patient-specific parameters. Only those patient specific pump parameters that are associated with the selected index of therapy, qualifier, and drug appear in the user interface 3400, and can be as few as one parameter and can incorporate as many parameters as are programmable within a medical infusion pump.

The user interface 3400 presents a standardized interface to a patient or caregiver using the user software 2600, such as at the point of care of a patient or other location on the infusion pump network. The user interface 2600 corresponds to any of a number of types of user software 2600 and administrative software 700. The user interface 3400 also can be configured to be used with various types of medical infusion pumps 102. Most pumps require programming with both patient specific pump parameters and non-patient specific pump parameters, but vary as to the data structure in which this data is passed to the pump. The user interface 3400 reflects from the user software 2600 the number of regions to create corresponding to the number of patient specific pump parameters, which are generic to various types of pumps. Therefore, the user interface 3400 can be used with any of a number of pumps having various brands, interfaces, data structures, or other variances.

The status indicator 3402 displays the library, therapy, qualifier, and drug which define the protocol loaded by the user software 2600. In the exemplary user interface, the library is an "ICU" library, the therapy selected is "Patient Controlled Analgesia", the qualifier is "Adult and Child over 5", and the drug is "Fentanyl 10 mcg/ml".

The continuous rate region 3404 defines the continuous, or basal, rate of drug delivery in the specific medical infusion pump. The continuous rate region 3404 includes a numerical reading 3416 and a meter, shown as a slider bar 3418 and an indicator 3419. The meter generally has two or more locations, each corresponding to a parameter value that can be programmed in the medical infusion pump. Generally, the positional relationship of the meter indicates the setting of the meter. The numerical reading 3416 reflects the current value for the continuous drug delivery rate.

In the embodiment of the meter shown as the slider bar 3418, the indicator 3419 slides along the slider bar 3418, and the positional relationship between the slider bar 3418 and indicator 3419 dictates the continuous drug delivery rate. Threshold indicators 3420 determine the safe limits within which the continuous rate can be set, and can represent either the hard limits or the soft limits set for the parameter by the administrative software 700. In the embodiment of the user software 2600 whose absolute threshold levels are limited by the hard limits set in the administrative software 700, the ends of each bar 3418 represent the hard limits and the threshold indicators 3420 represent the soft limits for the continuous rate. The thresholds are tested using the method described in FIG. 33.

The demand dose region 3406 customizes the demand dose, or bolus, delivered by the medical infusion pump. The demand dose region includes a numerical reading 3422 and a meter, shown as a slider bar 3424 and indicator 3425. The slider bar 3424 includes threshold indicators 3426 displaying either the hard or soft limit defined in the administrative software. The numerical reading 3422, slider bar 3424, indicator 3425, and threshold indicators 3426 operate analogously to those in the continuous rate region 3404, but set the bolus level parameter rather than the continuous rate parameter.

The demand dose lockout region 3408 customizes the time period after a bolus is delivered in which no additional bolus can be provided. The demand dose lockout region 3408 includes a numerical reading 3428 and a meter, shown as a slider bar 3430 and indicator 3431. The slider bar 3430 includes threshold indicators 3432 displaying either the hard or soft limit defined in the administrative software. The numerical reading 3428, slider bar 3430, indicator 3431, and threshold indicators 3432 operate analogously to those in the continuous rate region 3404, but set the demand dose lockout period parameter rather than the continuous rate parameter.

The timed limit region 3410 customizes the amount of the selected drug deliverable by a medical infusion pump within a specified timeframe. The timed limit region 3410 also includes a numerical reading 3434 and a meter, shown as a slider bar 3436 and indicator 3437. The slider bar 3436 includes threshold indicators 3438 displaying either the hard or soft limit defined in the administrative software. The numerical reading 3434, slider bar 3436, indicator 3437, and threshold indicators 3438 operate analogously to those in the continuous rate region 3404, but set the timed drug delivery threshold parameter rather than the continuous rate parameter.

The reservoir region 3412 defines the size of the reservoir used in conjunction with the medical infusion pump. The size of the reservoir is relevant to computing drug delivery volumes for the purpose of setting alarms and other indicators for replacing or refilling the reservoir. The reservoir region 3412, like the other regions, includes a numerical reading 3440 and a meter, shown as a slider bar 3442 and indicator 3443. The slider bar 3442 includes threshold indicators 3444 displaying either the hard or soft limit defined in the administrative software. The numerical reading 3440, slider bar 3442, and indicator 3443 operate analogously to those in the continuous rate region 3404, but set the reservoir volume parameter rather than the continuous rate parameter. In the embodiment shown, no threshold indicators are included in the reservoir region. This is because the reservoir region 3412 is allowed to use the entire operational range of the reservoir, since no hard limits are set in the reservoir volume region 2016 of FIG. 20 in the administrative software. However, in additional embodiments, one or more threshold indicators can be incorporated into the reservoir region to trigger a warning when the drug reservoir associated with the medical infusion pump contains less than the volume of drugs set by the threshold volume.

The meters in each region 3404-3412 may be adjustable in that each of the patient specific pump parameters are adjustable using a meter. The administrative software 700 enables the adjustment of one or more of the meters by allowing adjustment of those patient specific pump parameters using the options displayed on the user interface 1800 of FIGS. 18-20.

The control buttons 3414a-3414c allow a user to send the currently set parameters to the associated medical infusion pump, cancel the parameter customization, or receive help in the process.

FIG. 35 shows the user interface 3400 wherein the indicator 3437 in the timed limit region 3410 resides along the slider bar 3436 at a location outside the range defined by the threshold indicators 3438. A colored region 3502 appears around the slider bar and indicator, providing a visual warning to the user of the user software 2600 that abnormal or unadvisable pump settings exist. The colored region 3502 can change color (i.e. green or gray to yellow or red) indicating that the value is outside a threshold level.

It is noted that additional screen coloration or textual messages can be used to graphically send messages to a user or programmer of the medical infusion pump or associated computing system. For example, a color code system can be used to reflect a variety of conditions of the medical infusion pump. For example, a color could represent the current coding of the hospital or other health care facility at which the pump may be located. Additionally, the color code can represent a warning condition, a location at which the pump is used, a drug being administered by the pump, or an alert condition. Of course, the color code could represent additional characteristics of the medical infusion pump as well.

The color code can display on the computing system associated with the medical infusion pump, or can be reflected on a monitor associated to the medical infusion pump itself. Text messages can be sent from the server to be displayed on the monitor of the pump or computing system, such as warnings regarding medication, usage tips for the medical infusion pump, or other medical advice. Additionally, the color code can be placed behind images displayed on the pump which can also represent a region of the hospital, an image of the drug being administered, or other background images. Additionally, the screen coloration described can be represented as a flashing screen, a color changing (cross-fading or otherwise) screen, or various other color patterns.

Figure 36:
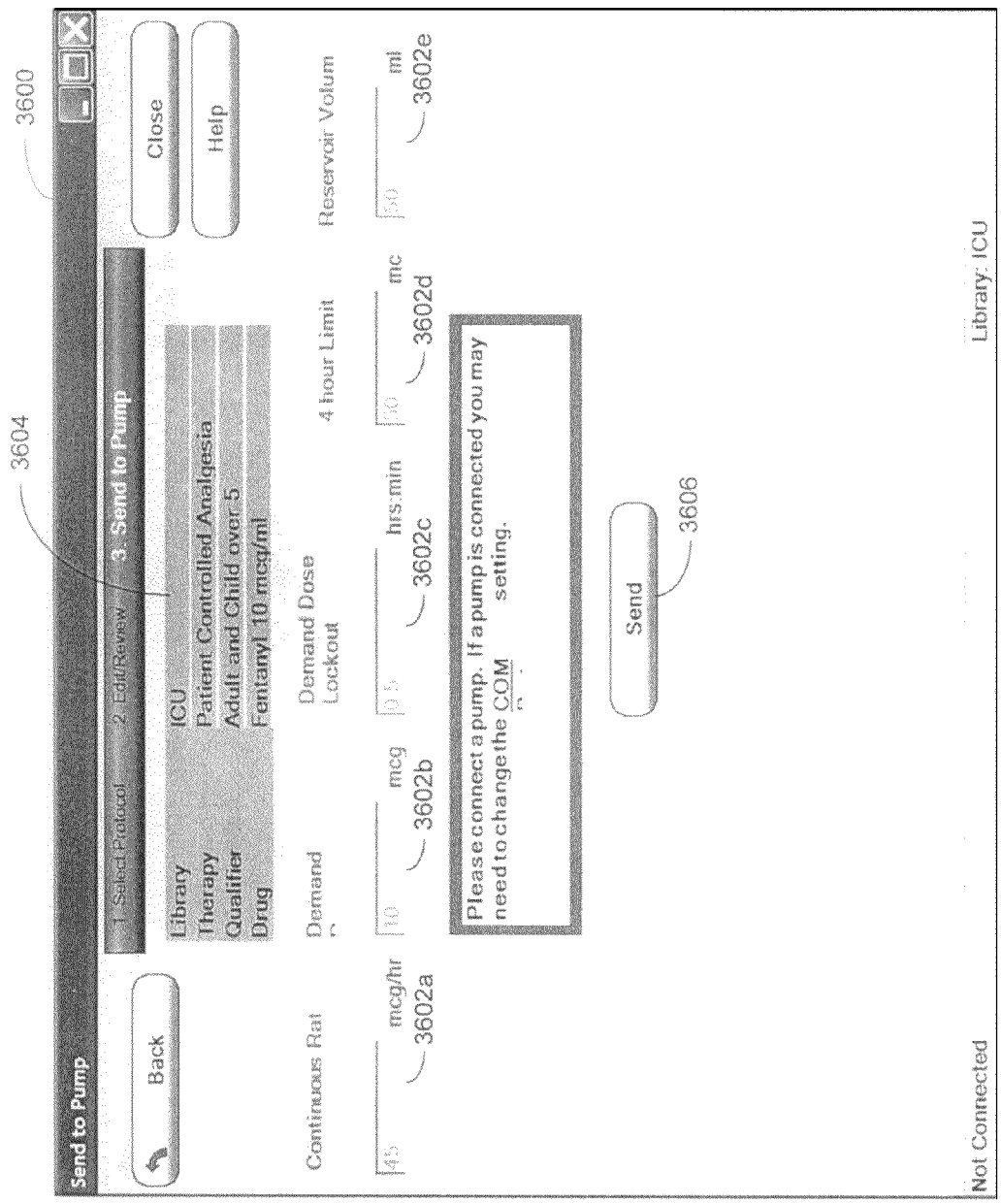
FIG. 36 is one example of a computer user interface medical infusion pump programming screen in accordance with the present disclosure.

FIG. 36 shows a pump programming user interface 3600 for guiding a user through the process of sending a pump program to a medical infusion pump. The programming screen can display properties of a pump to be programmed, and can include the settings 3602a-3602e that are to be sent to the pump, a protocol indicator field 3604, and a confirmation button 3606.

The settings 3602a-3602e reflect the customized pump parameters set using the user interface 3600 of FIGS. 34-35. The customized pump parameters correspond to the patient specific pump parameters 512a of FIG. 5, and can include one or more of continuous rate, demand dose, demand dose lockout, timed limits, reservoir volume, and other patient-specific parameters.

The protocol indicator field 3604 displays the current protocol selected, in this case shown as "Patient Controlled Analgesia", "Adult and Child over 5", and "Fentanyl 10 mcg/ml". The confirmation button 3606 sends the pump program, including the settings 3602a-3602e for the pump parameters, to the pump.

Figure 37:
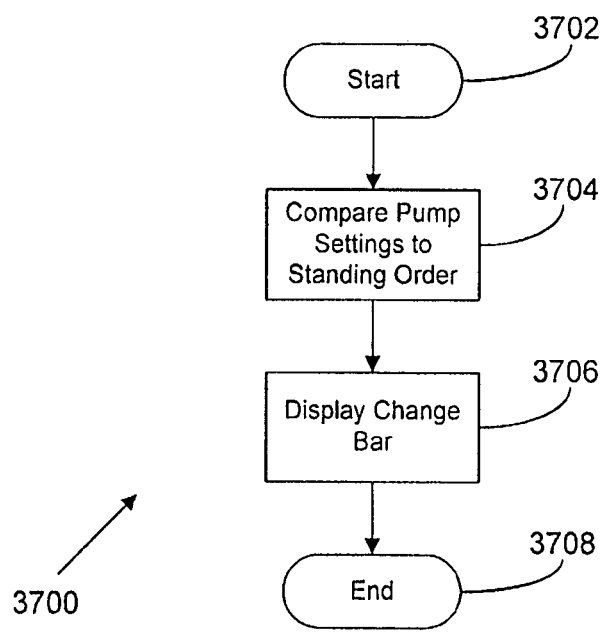
FIG. 37 is a flow diagram of methods and systems for displaying medical infusion pump customizations according to a possible embodiment of the present disclosure.

Once the pump is programmed, the pump program executes according to the protocol selected in conjunction with the customized parameters. Referring now to FIG. 37, an exemplary software process 3700 for displaying medical infusion pump customizations is shown. The process occurs within the pump 102, computing system 104, or a combination thereof, and can be part of a pump program sent to a medical infusion pump.

Customizations in protocol programming refer to differences between the actual pump operation and a standing order (i.e. settings programmed by an administrative user). The standing order can be an original pump parameter or initial value, and the pump operation for comparison can be either a current pump parameter or simply a non-original pump parameter.

A start module 3702 initiates the process 3700. Operational flow proceeds to a comparison module, shown as a compare pump settings to standing order module 3704. The pump settings stored on the pump or computing system as shown above in FIG. 5 can be compared against a standing order stored on a server as a pump protocol. To ensure that the correct standing order is accessed for comparison, a GUID assigned to the loaded pump settings corresponds to the protocol stored on the server. A display change bar module 3706 presents an indicator on either the medical infusion pump or associated computing system. In the display change bar module, the original pump parameter, or portion of a standing order, can be juxtaposed against the non-original pump parameter, such as in a table format. One or both of the original and non-original pump parameters can be a standard or customized pump parameter. Pump parameters that are displayed in the display change bar module 3706 include drug delivery rate, drug capacity, remaining capacity of the medical infusion pump, bolus levels or occurrences, alarm occurrences, threshold, and/or frequency, drug delivery periods, or other parameters.

In one possible embodiment, a legend can indicate the meaning of the pump parameters being displayed, and a time/date stamp can display the time at which the original and/or non-original pump parameter was measured. In additional embodiments, differences between the original and non-original pump parameters can be highlighted when displayed, such as by using a color change or other indicator.

Operational flow terminates at an end module 3708.

Figure 38:
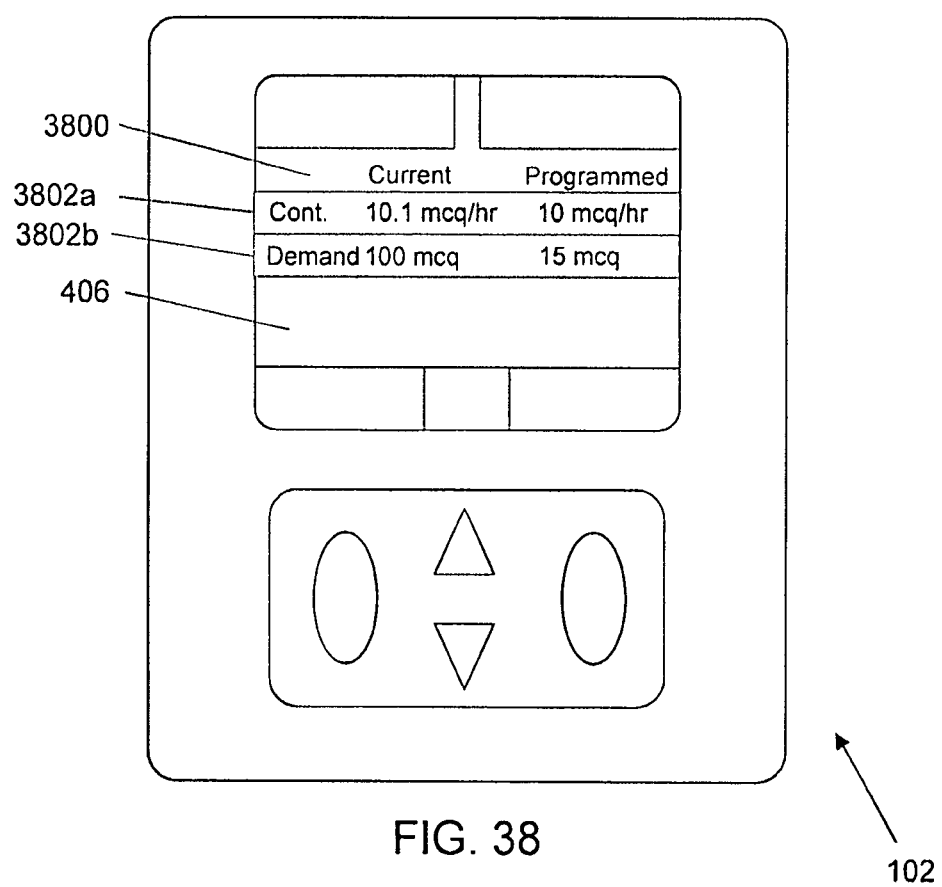
FIG. 38 is one example of a computer user interface pump comparison screen in accordance with the present disclosure.

FIG. 38 is an exemplary schematic illustration of a change bar 3800 displayed on a medical infusion pump 102. The change bar 3800 as shown is displayed on the screen 406 of the pump described above in FIG. 4. Alternately, the change bar 3800 can be displayed on a computing system 104 associated with the medical infusion pump 102.

The change bar 3800 includes a plurality of change bar entries 3802. The change bar entries correspond to pump parameters, and in the figure shown the entries 3802a-3802b correspond to patient specific pump parameters. The change bar can display non patient specific pump parameters as well.

The change bar 3800 can compare any of a number of original and non-original pump parameters. In one embodiment, the change bar 3800 compares the current operation of the pump to the originally programmed operation of the pump. In another embodiment, the change bar 3800 compares the operation of the pump as initially programmed to the suggested programming of the pump based on the original pump protocol. In a further embodiment, the change bar 3800 compares historical activity of the pump to the current pump protocol.

In one embodiment of the change bar 3800, the change bar entries 3802a-3802b change color when the difference between the original and the non-original pump parameters exceeds a threshold amount. The threshold amount can be, for example, the soft limits set in the administrative software 700. In a further embodiment, the text can change color when a difference greater than the threshold is detected. The change bar can incorporate additional graphics and images on the display.

Figure 39:
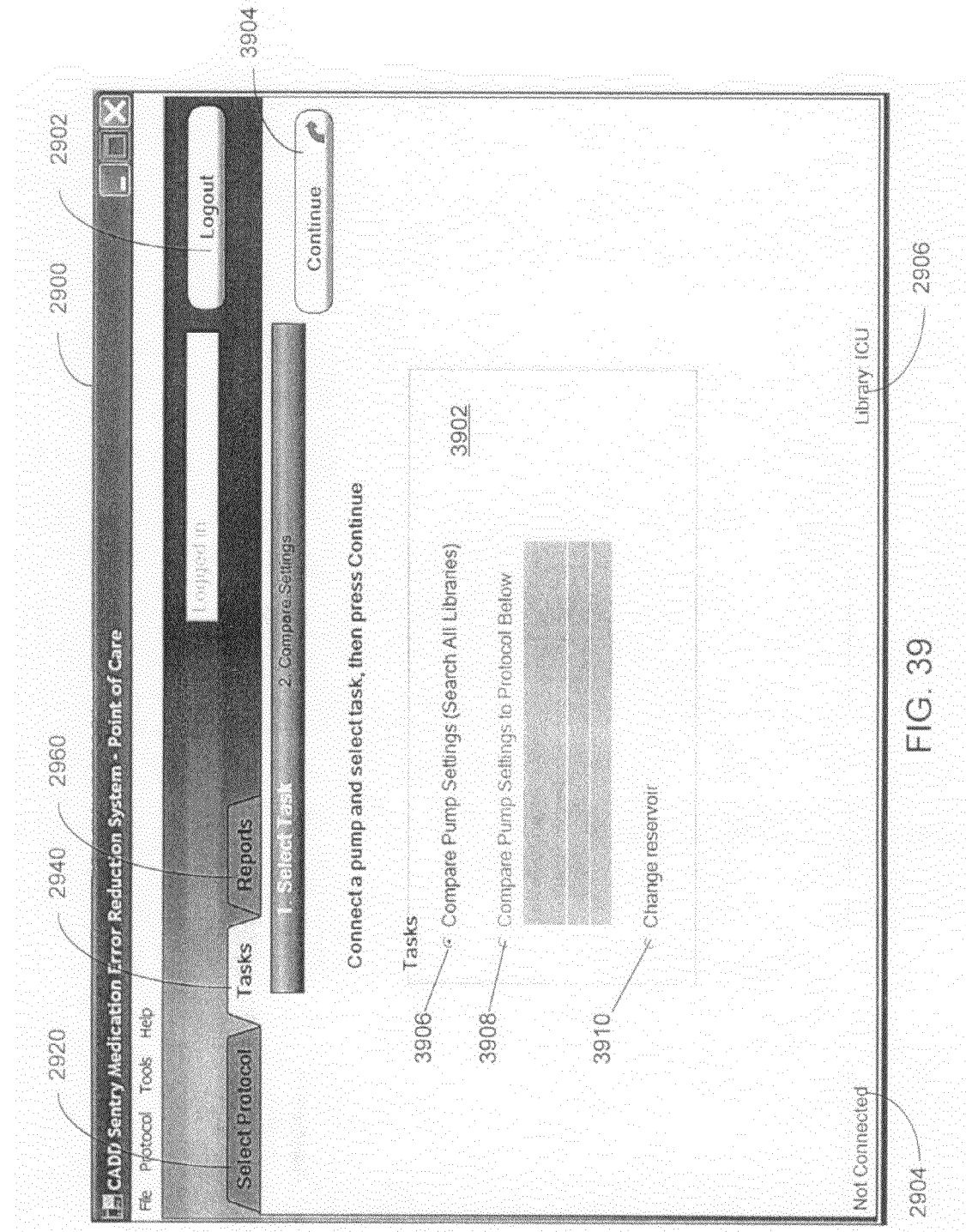
FIG. 39 is a schematic front view of a medical infusion pump displaying a change bar according to a possible embodiment of the present disclosure.

Referring now to FIG. 39, user software 2600 is again described in which the user interface 2900 of FIGS. 29-32 is shown with the tasks tab 2940 selected. The tasks tab 2940 includes a tasks region 3902 for selection of one or more task options, of which a comparison is displayed when the user selects the "continue" option 3904 shown. Tasks include operations related to maintenance of the pump once in operation. The tasks region 3902 includes a number of pump comparison options, such as a compare pump settings option 3906, a compare pump settings to protocol option 3908, and a change reservoir option 3910. The compare pump settings option 3906 compares the pump settings to the original protocol from which the pump parameters were based. The compare pump settings to protocol option 3908 compares all pump settings for the protocol selected.

The user software 2600 accesses the protocol loaded on the server 206 to compare the current pump settings to the original or current protocol using the options 3904, 3906. To accomplish this, it is necessary for the user software 2600 to clarify to the server 206 which protocol is being compared within the database 504 of FIG. 5. The user software 2600, in conjunction with the server 206 uses the globally unique identifier (GUID) described above in FIG. 5 to provide the identifier for corresponding the protocol on the pump 102 to the protocol as stored in the server 206. The GUID can be generated by the server 206 and transmitted alongside the protocol and/or library when transmitted to the computing system 104 or infusion pump 102, as described above.

The change reservoir option 3910 guides a user of the software 2600 through changing a drug reservoir used in conjunction with the medical infusion pump.

Figure 40:
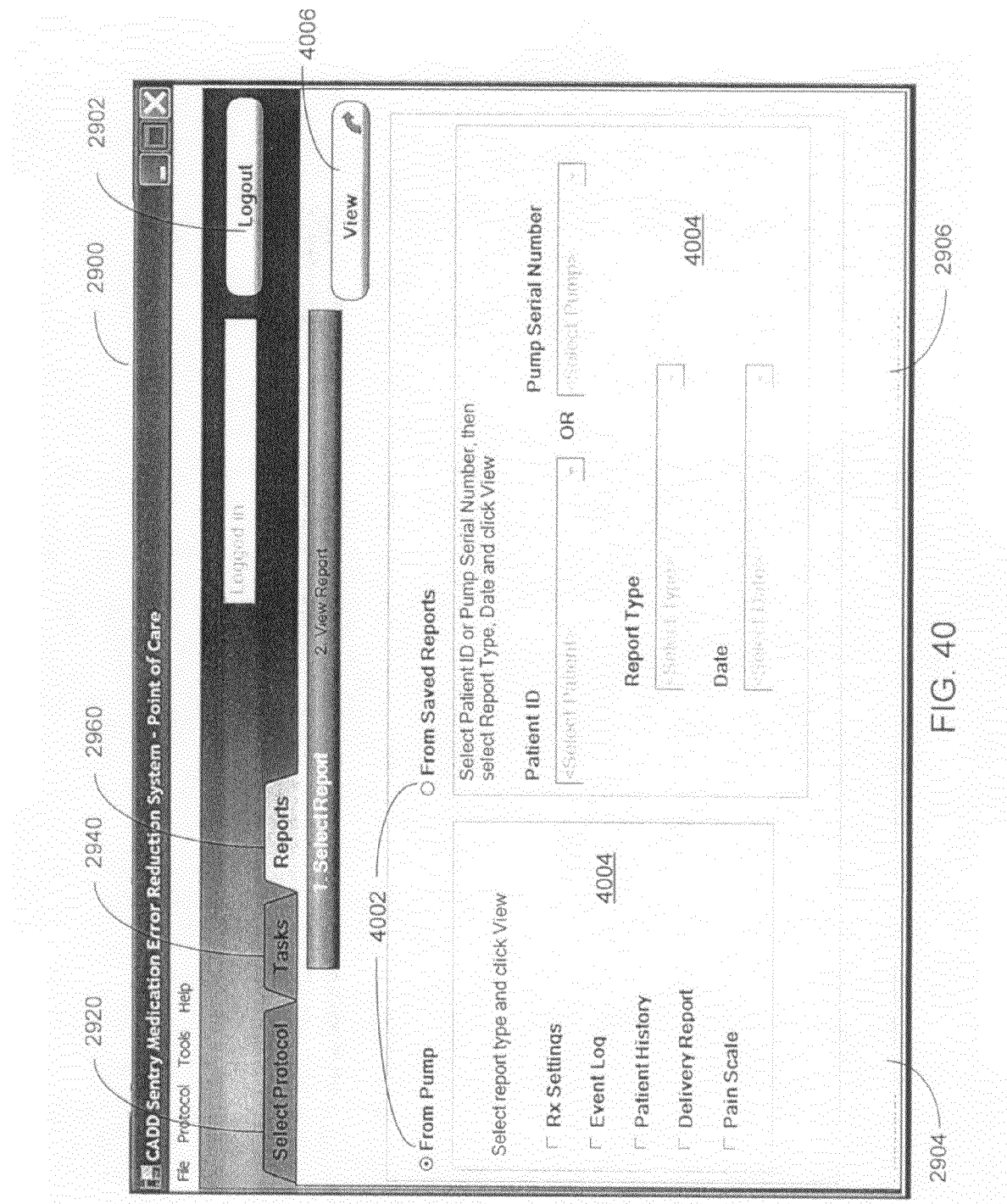
FIG. 40 is one example of a computer user interface report generation screen in accordance with the present disclosure.

FIG. 40 shows the user interface 2900 with the reports tab 2960 selected. During or after pump operation, reports including drug delivery or event logs are used to detect the condition of a patient or of the medical infusion pump. The events which can be tracked using reports tab 2960 are those which are available due to being automatically tracked by the medical infusion pump. The reports tab 2960 presents a number of selectable options for generating reports of pump activity, including time/date information, drug delivery information, and other event information. The reports tab 2960 includes source fields 4002 and option regions 4004. The source fields 4002 present a variety of sources from which reports can be drawn. The source fields 4002 can include the medical infusion pump and stored reports saved within the network. The option regions 4004 present a number of options related to the selected source. For example, a report generated directly from a medical infusion pump can be produced based on prescription settings, and event log, a patient history, drug delivery, or a reported pain scale. A report generated from a saved report can be produced by indicating the patient identification, the pump identification, or the report type and date. A view field 4006, upon selection by a user, generates the report based on the source and options selected.

Figure 41:
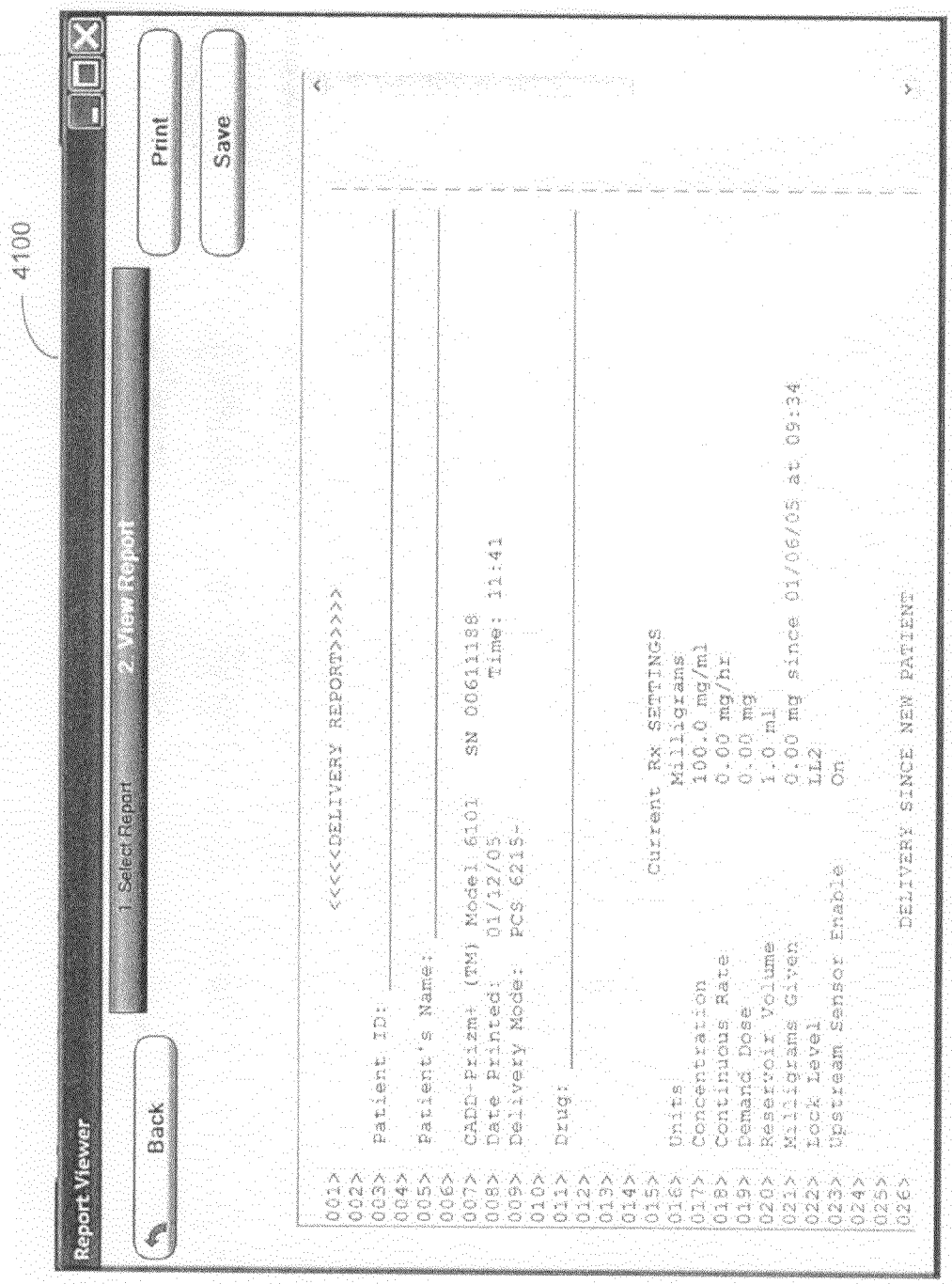
FIG. 41 is one example of a computer user interface report screen in accordance with the present disclosure.

FIG. 41 shows a report user interface 4100 for displaying operation of a medical infusion pump. The report user interface 4100 shows the report generated using the options selected in the report tab 2960. The report shown in the report screen is a drug delivery report, and can be printed, saved, or discarded by the user. The drug delivery report can include the volume of the drug delivered, as well as the timing of delivery of the drug. Additional attributes of the medical infusion pump can be reported in the drug delivery report as well.

Aspects of the invention described as being carried out by a computing system or otherwise described as a method of control or manipulation of data may be implemented in one or a combination of hardware, firmware, and software. Embodiments of the invention may also be implemented as instructions stored on a machine-readable medium, which may be read and executed by at least one processor to perform the operations described herein. A machine-readable medium may include any mechanism for storing or transmitting information in a form readable by a machine (e.g., a computer). For example, a machine-readable medium may include read-only memory (ROM), random-access memory (RAM), magnetic disc storage media, optical storage media, flash-memory devices, electrical, optical, acoustical or other form of propagated signals (e.g., carrier waves, infrared signals, digital signals, etc.), and others.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment. Therefore, the spirit and scope of the appended claims should not be limited to the description of the preferred versions contained herein.

The claimed invention is:

1. An apparatus for programming a medical infusion pump comprising:
   a memory configured to store at least two parameter values programmable into the medical infusion pump;
   a monitor;
   a programmable circuit in electrical communication with the memory and the monitor, the programmable circuit programmed to display on the monitor a meter and an indicator, a first location and a second location on the meter each representing a corresponding parameter value defining a first range of permissible programmable parameter values and one or more additional locations on the meter representing a second range defining soft limits within the first range, the indicator having a selectable positional relationship to the meter within the range, a selected position of the indicator with respect to the meter corresponding to a parameter value programmable into the medical infusion pump.

2. The apparatus of claim 1, wherein the programmable circuit is further programmed to download the parameter value to the medical infusion pump.

3. The apparatus of claim 1, wherein the programmable circuit is further programmed to display the parameter value.

4. The apparatus of claim 3, wherein the parameter value includes a numerical value.

5. The apparatus of claim 1, wherein the selectable positional relationship includes a continuous range of parameter values.

6. The apparatus of claim 5, wherein the meter is a slider bar.

7. The apparatus of claim 5, wherein the indicator is a pointer positionable along the slider bar.

8. The apparatus of claim 5, wherein the slider bar includes a warning region located along at least a portion of the slider bar.

9. The apparatus of claim 7, wherein the programmable circuit is further programmed to issue an alert when the pointer is located at a position in the warning region.

10. An apparatus for programming a medical infusion pump comprising:
    a memory configured to store at least two parameter values programmable into the medical infusion pump and one or more hard limits;
    a monitor;
    a programmable circuit in electrical communication with the memory and the monitor, the programmable circuit programmed to:
      set one or more hard limits to define a first range of permissible parameter values for programming a medical infusion pump;

set one or more soft limits to define a second range within the first range; and display on the monitor a meter and an indicator, the indicator having a positional relationship to the meter, a position of the indicator relative to the meter corresponding to a parameter value within the first range.

11. The apparatus of claim 10, wherein the programmable circuit is further programmed to allow selectable adjustment of the positional relationship between the indicator and the meter to define the parameter value to be programmed into the medical infusion pump.

12. The apparatus of claim 10, wherein the meter is a slider bar.

13. The apparatus of claim 12, wherein the memory is further configured to store the one or more soft limits defining the second range within the first range and the programmable circuit is further programmed to issue an alert if the parameter value is within the first range and not the second range.

14. The apparatus of claim 13, wherein the programmable circuit is further programmed to issue an alert when the pointer is located at a position in a warning region.

15. The apparatus of claim 13, wherein the programmable circuit is further programmed to display the meter using a graphical user interface associable with one or more types of medical infusion pumps.

* * * * *